(12) United States Patent
Ganley-Leal et al.

(10) Patent No.: US 9,617,325 B2
(45) Date of Patent: *Apr. 11, 2017

(54) TREATMENT OF IGE-MEDIATED DISEASE

(71) Applicants: BOSTON MEDICAL CENTER CORPORATION, Boston, MA (US); TRUSTEES OF BOSTON UNIVERSITY, Boston, MA (US)

(72) Inventors: Lisa Ganley-Leal, Newton, MA (US); John H. Connor, Newton, MA (US)

(73) Assignees: Boston Medical Center Corporation, Boston, MA (US); Trustees of Boston University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/584,524

(22) Filed: Dec. 29, 2014

(65) Prior Publication Data
US 2015/0183848 A1    Jul. 2, 2015

Related U.S. Application Data

(63) Continuation of application No. 13/512,949, filed as application No. PCT/US2010/058531 on Dec. 1, 2010, now Pat. No. 8,945,575.

(60) Provisional application No. 61/265,439, filed on Dec. 1, 2009.

(51) Int. Cl.
| | |
|---|---|
| *A61K 38/17* | (2006.01) |
| *C07K 14/435* | (2006.01) |
| *C07K 14/705* | (2006.01) |
| *A61K 31/56* | (2006.01) |
| *A61K 45/06* | (2006.01) |
| *C07K 14/195* | (2006.01) |
| *A61K 39/00* | (2006.01) |
| *C12N 15/09* | (2006.01) |
| *C12P 21/02* | (2006.01) |
| *A61K 38/00* | (2006.01) |

(52) U.S. Cl.
CPC .......... *C07K 14/7056* (2013.01); *A61K 31/56* (2013.01); *A61K 38/17* (2013.01); *A61K 39/0005* (2013.01); *A61K 45/06* (2013.01); *C07K 14/195* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,766,943 | A | 6/1998 | Lynch et al. |
| 6,410,714 | B1 | 6/2002 | Weber et al. |
| 7,074,896 | B1 | 7/2006 | Sondermann et al. |
| 7,504,482 | B2 | 3/2009 | Sondermann et al. |
| 2007/0207163 | A1 | 9/2007 | Sondermann et al. |
| 2009/0292113 | A1 | 11/2009 | Sondermann et al. |

FOREIGN PATENT DOCUMENTS

| | | |
|---|---|---|
| EP | 0254249 B1 | 1/1988 |
| EP | 0257114 A1 | 3/1988 |
| EP | 0324879 A1 | 7/1989 |
| EP | 1642974 A1 | 4/2006 |
| JP | S6368097 A | 3/1988 |
| WO | 9965524 A1 | 12/1999 |
| WO | 0040713 A1 | 7/2000 |
| WO | 2006067406 A1 | 6/2006 |
| WO | 2009103067 A2 | 8/2009 |

OTHER PUBLICATIONS

Amrol et al. , (2005) "Soluble CD23 and Interleukin-1 Receptor Antagonist in Human Asthmatics Following Antigen Challenge" (Journal of Asthma 1:73-76).
Barnes et al., The Journal of Clinical Investigation, 2001, vol. 107, No. 3, pp. 265-266.
Daniels et al., Daniels, B. et al., (2005) Cellular Immunity 234(2):146-153.
Griffith et al., "Schistosomes Target Human CD23-Mediated Immunity in Immuno-Evasive Tactics", American Journal of Tropical Medicine and Hygiene, V. 81, No. 5, pp. 99, 2009.
Hibbert et al., "The structure of human CD23 and its interactions with IgE and CD21", The Journal of Experimental Medicine, V. 202, No. 6, pp. 751-760, 2005.
Huggins et al., American Family Physician, 2004, vol. 70, pp. 689-696.
McCloskey et al., The Journal of Biological Chemistry, 2007, vol. 282, No. 33, pp. 24083-24091.
Schulz et al., "Cleavage of the Low-Affinity Receptor for Human IGE (CD23) by a Mite Cysteine Protease: Nature of the Cleaved Fragment in Relation to the Structure and Function of CD23", European J. of Immunology, vol. 27, No. 3, pp. 583-588, 1997.

*Primary Examiner* — Bridget E Bunner
*Assistant Examiner* — Fozia Hamud
(74) *Attorney, Agent, or Firm* — Nixon Peabody, LLP; Ronald I. Eisenstein; Leena H. Karttunen Contarino

(57) ABSTRACT

The methods and compositions described herein are based, in part, on the discovery of a polypeptide of soluble CD23 (sCD23) that binds and sequesters IgE. Thus, the sCD23 peptides, polypeptides and derivatives described herein are useful for treating conditions or disorders involving increased IgE levels such as e.g., allergy, anaphylaxis, inflammation, lymphoma, and certain cancers.

14 Claims, 13 Drawing Sheets

FIG. 1

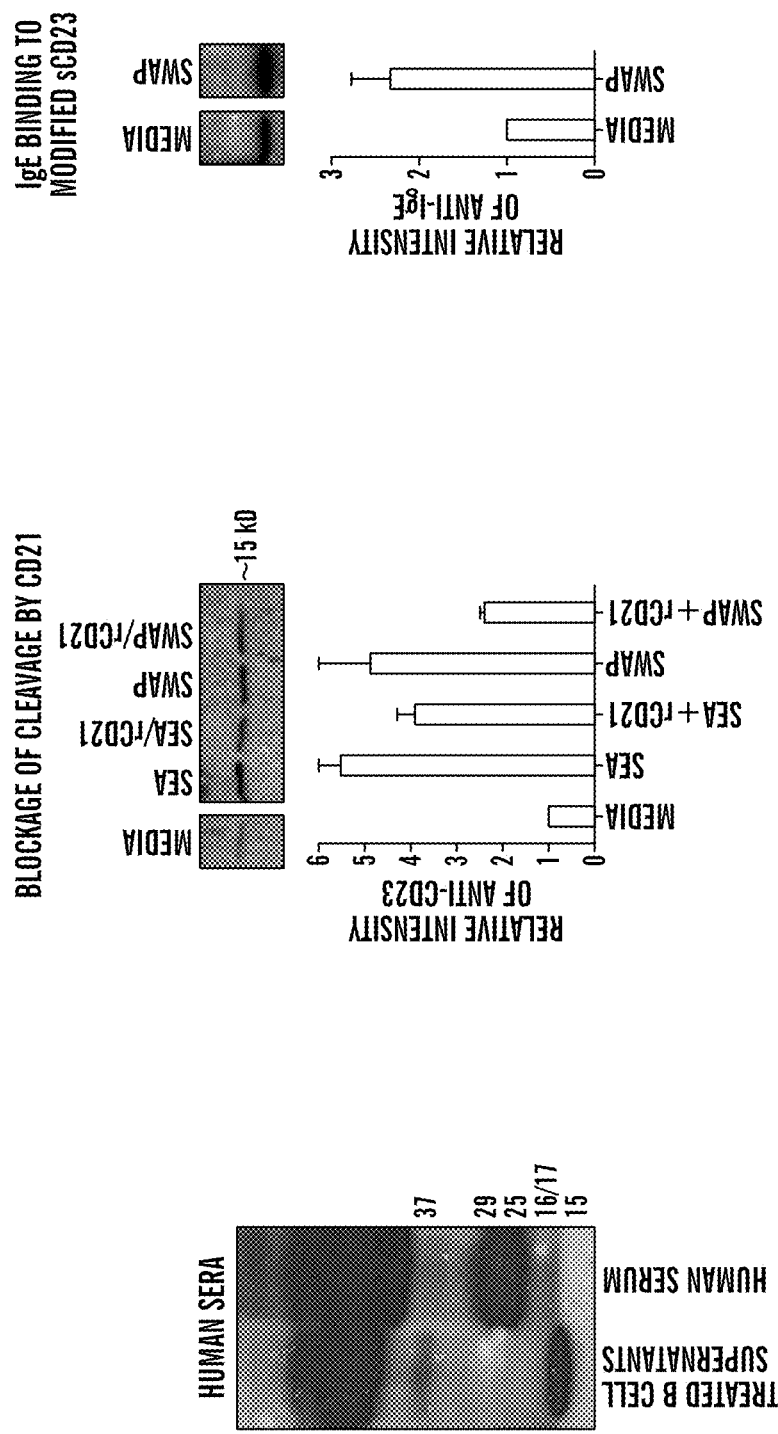

SCHISTOSOME-MODIFIED sCD23 IS MONOMERIC AND LACKS CD21 BINDING ABILITY

LECTIN HEAD: IgE BINDING SITE

"TAIL": CD21 BINDING SITE

Derp I

STALK

ADAM10

CELL MEMBRANE

TRIMERIC CD23 (HIGH AFFINITY FOR IgE)

*FIG. 3*

THE APPLICATION OF SCHISTOSOME-MODIFIED sCD23

LACKS ABILITY TO BIND CD21 REDUCING OTHER IMMUNOLOGIC EFFECTS

BINDS IgE WITH LOW AFFINITY. INCREASING THE SYSTEMIC CONCENTRATION WOULD ALLOW SEQUESTRATION OF IgE AND PREVENTION OF BINDING TO FcεRI + CELLS

*FIG. 4*

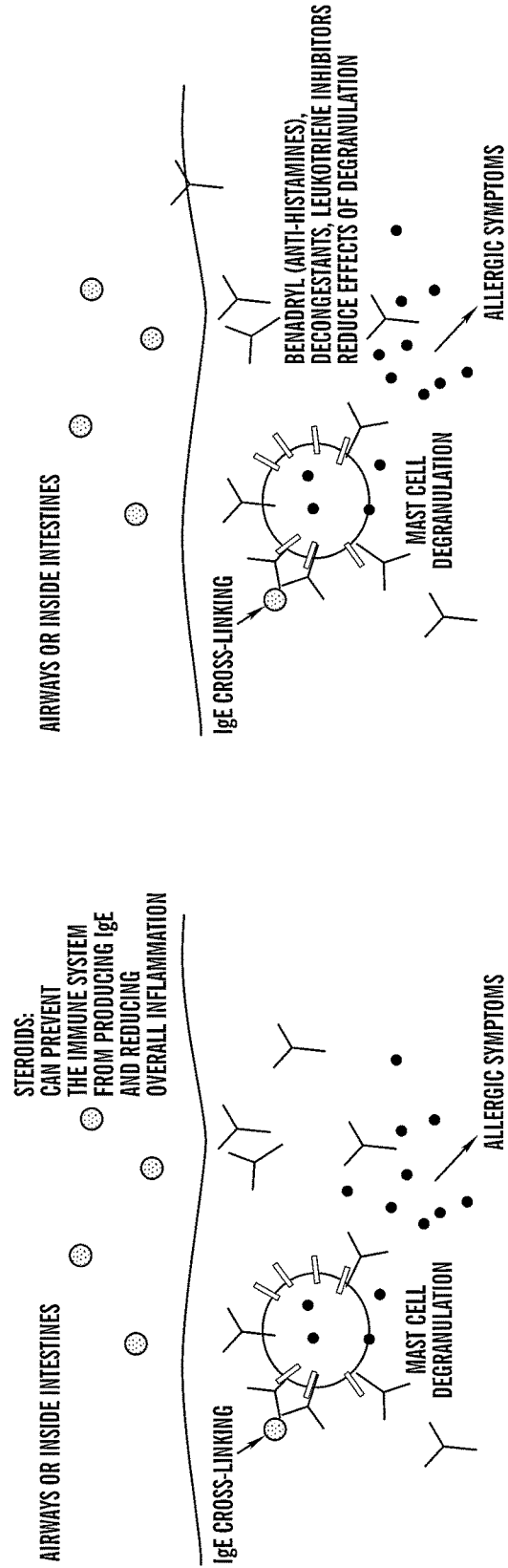

FIG. 5I

Figure 6
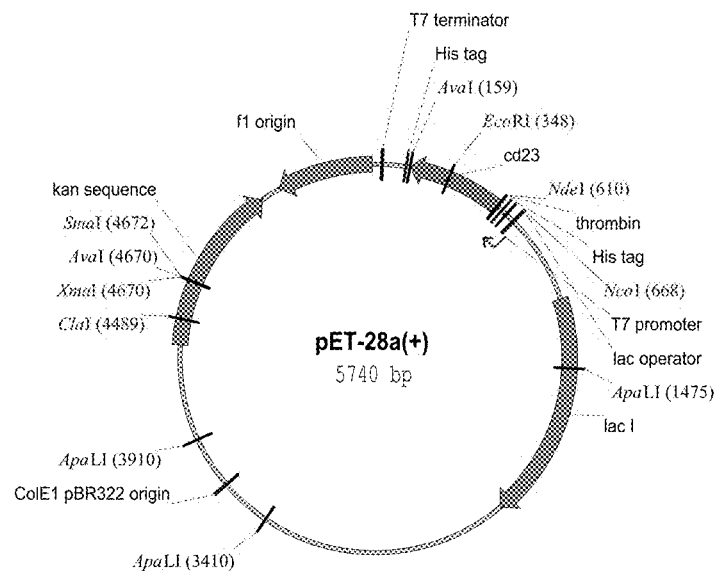
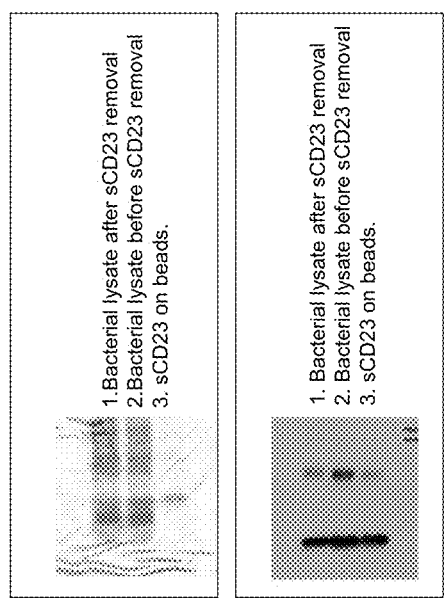
Figure 7A    Figure 7B

1. BACTERIAL LYSATE AFTER sCD23 REMOVAL
2. BACTERIAL LYSATE BEFORE sCD23 REMOVAL
3. sCD23 ON BEADS

1. BACTERIAL LYSATE AFTER sCD23 REMOVAL
2. BACTERIAL LYSATE BEFORE sCD23 REMOVAL
3. sCD23 ON BEADS

METAL BINDING ALTERATION

WILDTYPE CD23
— CALCIUM

CD23 BINDS $Ca^{++}$
USING 4 AMINO ACIDS
THAT MAKE 5 BONDS
TO CHELATE THE METAL.
OTHER SIMILAR PROTEINS
MAKE 6 BONDS FOR
LIGAND BINDING.

MUTATED CD23

AMINO ACID 258
TO A GLUTAMATE

THE MUTATED ITERATION
OF MODIFIED sCD23 IS CHANGED
SUCH THAT IT WILL NOW POSSESS
6 BONDS TO CHELATE $Ca^{++}$
THEREBY INCREASING THE ABILITY
OF sCD23 TO "HOLD ONTO" IgE.

*FIG. 8*

TREATMENT OF IGE-MEDIATED DISEASE

CROSS REFERENCE TO RELATED APPLICATIONS

This application is continuation application of U.S. Ser. No. 13/512,949, filed on Oct. 29, 2012, which is a 35 U.S.C. §371 National Phase Entry Application of International Application No. PCT/US2010/058531, filed Dec. 1, 2010, which designates the United States, and which claims benefit under 35 U.S.C. §119(e) of U.S. Provisional Application No. 61/265,439, filed Dec. 1, 2009 the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jun. 11, 2012, is named 066742US.txt and is 149,050 bytes in size.

GOVERNMENT SUPPORT

This invention was made with Government support under Contract No. AI074843 awarded by the National Institutes of Health. The Government has certain rights in the invention.

FIELD OF THE INVENTION

The field of the invention relates to the treatment of IgE mediated disease.

BACKGROUND

Allergy is a chronic inflammatory disease that encompasses a broad range of manifestations including allergic rhinitis (AR), eczema, and asthma. It has been approximated that up to 25% (75 million) of the US population suffers from some form of allergy. In fact, seasonal AR is estimated to affect 25% of the Caucasian race of which 40% are children. The prevalence of asthma is estimated to be 9% (27 million people) in the USA. Food allergies are on the rise and are particularly dangerous in young children as they have a propensity to develop into life threatening conditions, such as anaphylactic shock.

60 million Americans suffer from AR in the US. AR is characterized by nasal congestion, rhinorrhea (runny nose), sneezing, and nasal and eye itchiness. AR can be classified as a nuisance condition but it is associated with significant morbidity that often results in a reduced quality of life, emotional well-being and productivity. Most of the reduction in the quality of life can be attributed to sleep disturbances. The burden is heavy on children as 88% of pediatric patients with AR have difficulty sleeping.

In fact, AR in particular, places a considerable economic burden on the US health care system which includes direct costs to both patients and insurance providers and indirect costs such as absenteeism and presenteeism. Further, children with AR are more likely to have increased visits to their physicians further increasing the cost of health care.

SUMMARY OF THE INVENTION

The methods and compositions described herein are based, in part, on the discovery of a polypeptide of soluble CD23 (sCD23) that binds and sequesters IgE to induce an anti-inflammatory response. Thus, the sCD23 polypeptides, peptides and derivatives described herein are useful for treating conditions or disorders involving increased IgE levels such as e.g., allergy, anaphylaxis, inflammation, lymphoma, and certain cancers.

In one aspect, provided herein are compounds of the formula $X_1$—R, wherein R comprises SEQ ID No. 4 and $X_1$ comprises at least three contiguous amino acids of the sequence TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 7), and contiguous fragments thereof. In one embodiment, $X_1$ consists of the sequence TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 7). In one embodiment, $X_1$ comprises at least 5 contiguous nucleotides of the sequence TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 7). In other embodiments, $X_1$ comprises or consists of at least 7, at least 9, at least 10, at least 12, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105 contiguous amino acids of the sequence TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 7). In one embodiment, the fragment ends with the carboxy sequence LQVS (SEQ ID NO: 8). In one embodiment conservative amino acid substitutions as set forth herein can be made.

In one embodiment of this aspect, the compound binds IgE. In another embodiment of this aspect, the compound does not bind CD21.

In another embodiment of this aspect, the compound comprises a high affinity binding site for IgE. In another embodiment, the high affinity binding site is generated by amino acid substitution of R. In another embodiment, the amino acid substitution is D107E.

Also provided herein in another aspect are compounds of the formula R—$X_2$, wherein R comprises SEQ ID No. 4 and $X_2$ comprises SEGSAE (SEQ ID NO: 9), SEGSA (SEQ ID NO: 10), SEGS (SEQ ID NO: 11), SEG, SE, S, L, —COOH. In one embodiment, the compound is $R_0$. In one embodiment, the compound can have the formula $X_1$—$R_0$—$X_2$, wherein $X_1$ and $X_2$ are as defined herein. In one embodiment of this aspect, the compound binds IgE. In another embodiment of this aspect, the compound does not bind CD21.

In another embodiment of this aspect, the compound comprises a high affinity binding site for IgE. In another embodiment, the high affinity binding site is generated by amino acid substitution of R. In another embodiment, the amino acid substitution is D107E (e.g., SEQ ID No: 2).

In one embodiment the compound is PEGylated.

Another aspect described herein relates to compositions for sequestering IgE, the composition comprising: an effective amount of a compound as described above and a pharmaceutically acceptable carrier.

Also provided herein are methods for reducing a subject's immune response to an allergen, the method comprising: administering to a subject a pharmaceutical composition containing an effective amount of a compound of formula $X_1$—$R_0$—$X_2$, $R_0$—$X_2$, or $X_1$—$R_0$, and a pharmaceutically acceptable carrier.

In one embodiment, the pharmaceutical composition is administered prophylactically to a subject at risk of having an immune response to an allergen.

In another embodiment of this aspect, the pharmaceutical composition is administered to a subject following exposure to the allergen.

In another embodiment of this aspect, the method further comprises administering steroid therapy.

In another embodiment of this aspect, the method further comprises administering allergy shots to said individual.

In another embodiment of this aspect, the allergen is a food allergen, a pollen, a plant allergen, a dust mite, animal dander, insect stings, a fungus, a spore, a mold, latex, or a drug.

In another embodiment of this aspect, the method further comprises a step of selecting an individual having an immune response to an allergen.

Also provided herein are methods for treating an IgE-mediated disease in a subject, the method comprising administering to a subject a pharmaceutical composition containing an effective amount of a compound of formula $X_1$—$R_0$—$X_2$, $R_0$—$X_2$, or $X_1$—$R_0$, and a pharmaceutically acceptable carrier.

In one embodiment of this aspect, the IgE mediated disease is selected from the group consisting of: allergy, anaphylaxis, asthma, eczema, and rhinitis Also provided herein are methods for reducing the development of a chronic immune response to an allergen, the method comprising administering to a subject a pharmaceutical composition containing an effective amount of a compound of formula $X_1$—$R_0$—$X_2$, $R_0$—$X_2$, or $X_1$—$R_0$, and a pharmaceutically acceptable carrier.

Also provided herein are methods for reducing the dose of an allergy or anaphylaxis treatment, the method comprising administering to a subject being treated with an allergy or anaphylaxis treatment a pharmaceutical composition containing an effective amount of a compound of formula $X_1$—$R_0$—$X_2$, $R_0$—$X_2$, or $X_1$—$R_0$, and a pharmaceutically acceptable carrier.

Definitions

A "subject" in the context of the present invention is preferably a mammal. The mammal can be a human, non-human primate, mouse, rat, dog, cat, horse, or cow, but is not limited to these examples.

As used herein, the term "sCD23 peptide" or "sCD23 polypeptide" refers to a modified peptide or polypeptide of soluble CD23 comprising, at a minimum, amino acid residues 156-292 of sCD23. The term "sCD23 peptide" or "sCD23 polypeptide" also encompasses peptides or polypeptides having conservative substitution mutations, mutations to enhance IgE binding activity, and/or mutations to enhance calcium binding activity. In certain embodiments, the term sCD23 peptide or polypeptide refers to a polypeptide of SEQ ID NO: 1, 2, 3, 4, 5, or 6, or a derivative thereof. The terms peptide and polypeptide are used herein to denote protein fragments of different lengths, wherein the term "peptide" refers to short amino acid sequences and polypeptide refers to longer amino acid sequences. The use of sCD23 peptides and polypeptides are both contemplated for use with the methods and compositions described herein. One of skill in the art will understand the terms "peptide" and "polypeptide." One need not know the exact length of an sCD23 peptide or polypeptide since both are contemplated for use with the methods described herein.

The term "derivative" as used herein refers to peptides or polypeptides which have been chemically modified, for example by ubiquitination, labeling, pegylation (derivatization with polyethylene glycol) or addition of other molecules. A molecule is also a "derivative" of another molecule when it contains additional chemical moieties not normally a part of the molecule. Such moieties can improve the molecule's solubility, absorption, biological half life, etc. The moieties can alternatively decrease the toxicity of the molecule, or eliminate or attenuate an undesirable side effect of the molecule, etc. Moieties capable of mediating such effects are disclosed in Remington's Pharmaceutical Sciences, 18th edition, A. R. Gennaro, Ed., MackPubl., Easton, Pa. (1990). A derivative of an sCD23 peptide/polypeptide will substantially retain the IgE binding activity of the peptide/polypeptide, that is, the derivative will retain at least 20% of the IgE binding activity of the parent peptide/polypeptide as measured using e.g., an in vitro immunoprecipitation activity assay as described herein in the Example section. In one embodiment, the peptide or polypeptide is PEGylated.

As used herein, the term "PEGylated" refers to a polyethylene glycol derivative attached to a peptide or polypeptide as described herein.

As used herein, the term "substantially retains IgE binding activity" means that a derivative will retain at least 30% of the IgE binding activity (as assessed by an in vitro immunoprecipitation assay as provided herein in the Examples section) of the polypeptide or peptide from which it is derived. In other embodiments, the derivative will retain 3 at least 40%, at least 50%, at least 60%, at least 70%, at least 80%, at least 90%, at least 95%, at least 99% or even 100% of the IgE binding activity of the peptide/polypeptide from which it is derived. The term "substantially retains IgE binding activity" also encompasses an increase in the IgE binding activity of a derivative compared to that of the parent peptide/polypeptide, for example, the derivative can have at least a 2-fold increase, at least 5-fold, at least 10-fold, at least 20-fold, at least 50-fold, at least 100-fold, at least 1000-fold or more increase in IgE binding activity compared to the parent peptide/polypeptide from which it is derived. IgE binding assays for assessing IgE binding activity are well known in the art (see e.g., Chen et al. *J Immunological Methods* 58(1-2):59-71 (1983); Matsuo et al. *J Immunology* 175:8116-8122 (2005)).

As used herein, the term "lacks substantial CD21 binding" refers to the lack of detectable binding of an sCD23 polypeptide to CD21 using e.g., an in vitro binding assay. As used herein, the term "reduced CD21 binding" refers to a decrease in the level of CD21 binding to a modified sCD23 polypeptide of at least 10% (as measured using e.g., an in vitro CD21 binding assay) compared to native sCD23; preferably the level of CD21 binding is reduced at least 20%, at least 30%, at least 40%, at least 50%, at least 60%, at least 70%, at least 80%, at least 90%, at least 95%, at least 99% or even 100% (i.e., below detectable levels using a standard CD21 binding assay).

As used herein, the term "immune response to an allergen" is used to describe an increase in IgE levels in a subject and/or a subject's response to increased IgE levels, and can present with such symptoms as sneezing, coughing, sinus congestion, mucus production in the sinuses (rhinitis) or lungs (asthma).

As used herein, the term "increase in IgE levels" refers to an increase in the level of IgE in a subject of at least 10% following exposure to an allergen compared to the level of IgE prior to allergen exposure. In other embodiments, an "increase in IgE levels" refers to an increase in IgE in a subject exposed to an allergen of at least 20%, at least 30%, at least 40%, at least 50%, at least 60%, at least 70%, at least 80%, at least 90%, at least 95%, at least 1-fold, at least 5-fold, at least 10-fold, at least 100-fold, at least 500-fold, at least 1000-fold, at least 5000-fold, at least 10,000-fold or more compared to the level of IgE in the subject prior to allergen exposure. Allergen exposure can be spontaneous, in that the subject comes into contact with an allergen, for example, in a particular environment, by ingestion, or during a particular season. Alternatively, an allergen can be actively delivered in a clinical setting such as e.g., skin tests for allergy.

As used herein, the term "administered prophylactically" refers to administration of a peptide or polypeptide to a subject prior exposure to an allergen expected to promote an increase in IgE levels, for example prior to allergen exposure. Administration can occur e.g., minutes before an expected exposure, or on e.g., a daily, weekly, bi-weekly, or monthly basis. An appropriate treatment regime can be determined by one of skill in the art. Prophylactic administration also encompasses co-administration with other agents such as e.g., allergy shots, or steroid injections.

As used herein, the term "following exposure to the allergen" refers to administration following exposure to an allergen including within seconds, minutes, or hours following a subject's exposure to an allergen, or when at least one symptom of IgE mediated disease is present in a subject. Thus, the methods and compositions used herein are useful in the treatment of both an acute exposure to an allergen and chronic (e.g., seasonal) exposure to an allergen.

As used herein, the term "selecting an individual having an immune response to an allergen" refers to a step of first diagnosing a subject as having an IgE mediated response to an allergen prior to administration of a modified sCD23 peptide or polypeptide. Diagnosis of an allergic response can be performed using any number of techniques known to those of skill in the art, such as e.g., skin prick test, intradermal test, skin patch test, blood test (e.g., ELISA, immunoassay capture test, radioallergosorbent test), among others.

As used herein, the term "IgE mediated disease" refers to a disease that is mediated, at least in part, by an increase in the levels of IgE as that term is used herein.

As used herein, the term "chronic immune response to an allergen" refers to an IgE mediated response that develops into a chronic condition or disease, such as asthma, or eczema. The term "chronic immune response" is not intended to encompass a single, acute exposure to an allergen e.g., insect stings, poison oak, etc.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

BRIEF DESCRIPTION OF THE FIGURES

Figure 1:
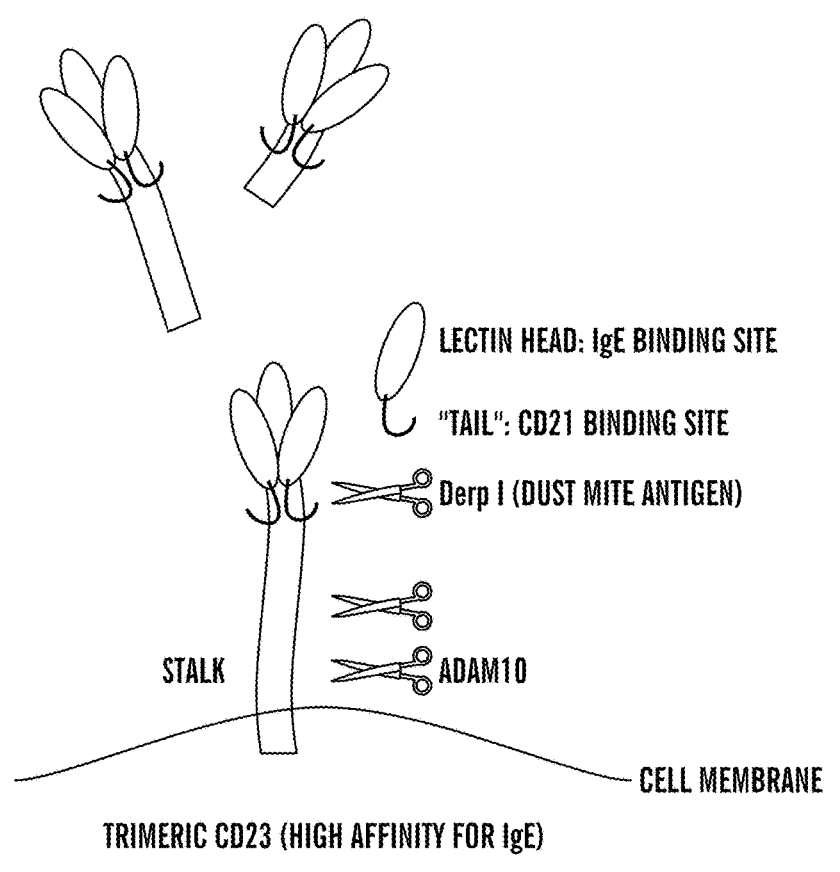

FIG. 1 shows depiction of cell bound CD23 cleavage to produce various polypeptides of soluble CD23.

FIGS. 2A-2C show characterization of sCD23 in supernatants of B cells treated with schistosome antigens. FIG. 2A shows that an ~15 kDa band accumulates in B cell culture supernatants in the presence of schistosomal egg protein (SEA). Human sera contains multiple sizes of CD23 but generally lack the 15 kDa protein. FIG. 2B shows the increase in the 15 kDa band by SEA or SWAP was decreased by the presence of sCD21 indicating that sCD21 blocks a cleavage site. FIG. 2C shows that SWAP-treatment enhances the binding of free IgE to low MW sCD23. SWAP: soluble worm antigen preparation from schistosomes.

FIG. 3 shows generation of a 15 kDa sCD23 protein in a parasitic disease in which the protein was discovered. Schistosomes modify sCD23 in a manner that retains the IgE binding but reduces the CD21-binding ability.

FIG. 4 shows application of schistosome-modified sCD23 for binding IgE.

FIGS. 5A-5I show depiction of the advantage of modified sCD23 in reducing allergic responses. FIG. 5A shows sensitized mast cells at a mucosal surface (lung or gut) poised to respond to allergens. In FIG. 5B circles demonstrate antigen-specific region of IgE antibody. FIG. 5C. Antigen-binding to the cell-bound IgE "cross-links" the IgE. FIG. 5D shows that cross-linked IgE induces cellular degranulation which causes allergic symptoms. FIG. 5E shows that cortico-steroids inhibit the production of IgE and other inflammatory events. FIG. 5F shows that anti-histamines, decongestants, and leukotriene inhibitors reduce the effects of degranulation following IgE cross-linking. FIG. 5G shows mechanism of Xolair which binds the non-specific Fc region of IgE and prevents IgE from binding to its cellular receptors. FIG. 5H shows that due to its binding properties, Xolair has the potential to globally cross-link cell-bound IgE. Because Xolair binds IgE in the non-specific region, it has the potential to globally induce a potent allergic response from the activated cells. FIG. 5I shows that mechanism of action of modified sCD23 which binds the Fc region of IgE (with lower affinity) and inhibits IgE binding to IgE receptors. Because of its structure, the modified sCD23 polypeptide has a very low potential to cross-link cell bound IgE non-specifically and thus presents a low risk of inducing anaphylaxis and other severe adverse effects.

FIG. 6 shows a schematic diagram relating to the production of modified sCD23. Image shows a schematic representation of the expression vector used to produce sCD23 peptides. Selection and expression control components are highlighted. The sCD23 sequences were cloned into the pET-28a(+) vector and propagated in Top10F media. For expression purposes, BLR DE3 bacteria were transformed and selected on Kan plates. Colonies were chosen for protein production using standard protocols.

FIG. 7A shows modified sCD23 was expressed as described in FIG. 6. Shown is a protein fragment represented in SEQ ID No. 1, containing a c-myc peptide tag and a 6-his (SEQ ID NO: 12) affinity purification tag. Following expression, protein was recovered using nickel chromatography. Proteins were then separated by SDS-PAGE and the resulting purified protein is shown in Lane 3. FIG. 7B shows Western blot analysis using an anti-myc antibody identifies a band of the same molecular weight as the coomassie-stained band in 7A, lane 3. Notable is that all fractions contain the protein as expected. Thus, the sequence used to generate the modified sCD23 protein generates a highly similar protein to the fragment generated by schistosomes. Further, this demonstrates that the sCD23 protein fragments are easily expressed thereby facilitating the required increase in scalability for clinical trials and patient treatment.

FIG. 8 is a schematic showing a high affinity modified sCD23, an exemplary modification of the sCD23 protein.

FIG. 10A shows recombinant full length CD23 exposed to schistosome antigens inhibits exogenous IgE from binding to IL-10-treated THP-1 cells (left panel). IL-10 increases FcαRIα chain expression, the high affinity IgE receptor, by THP-1 cells. No IgE: gray fill; 1 µg/ml IgE; IgE+modified sCD23 (1 µg/ml). THP-1 cells were exposed to IgE and sCD23 and rotated at 4° C. for 2 hours. Surface IgE was measured by flow cytometry. Modified sCD23 antigen prep contained both full length and 15 kDa protein fragments. FIG. 10B shows that unmodified rsCD23 does not inhibit IgE binding compared to IgE alone. No IgE shown as a gray fill.

DETAILED DESCRIPTION

Figure 5B:
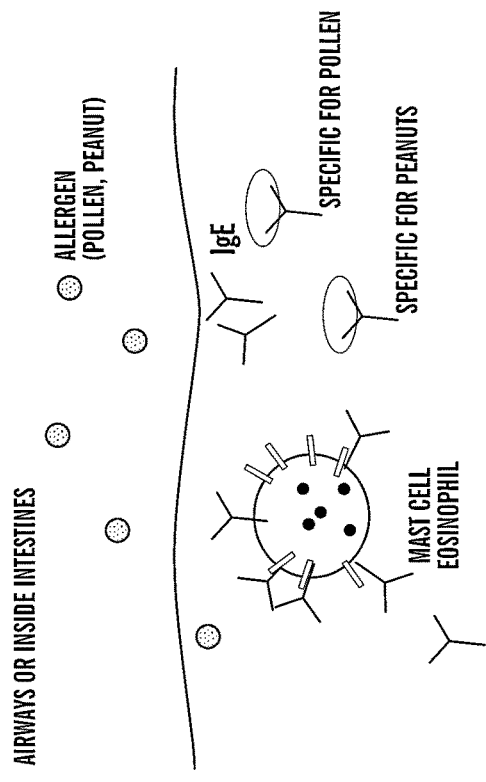

Described herein are methods and compositions useful for treating IgE mediated conditions or diseases comprising administering to a subject in need thereof, a modified peptide (or polypeptide) of soluble CD23 that binds IgE and in some embodiments lacks substantial CD21 binding. The invention is based, in part, on the discovery that soluble polypeptides of CD23 can bind and sequester IgE, prevent IgE binding to its receptor, thereby reducing an immune response initiated by IgE. The methods and compositions described herein are useful for treating IgE mediated conditions or diseases such as e.g., allergic diseases, lymphomas, inflammatory diseases and certain cancers.

IgE Mediated Disease

The methods and compositions described herein are useful for treating any IgE mediated disease, that is a condition or disorder characterized by increased levels of IgE. Such disorders include, for example, allergic diseases such as rhinitis, eczema, food allergy, asthma, and anaphylactic shock; lymphoma; pancreatic cancer; cystic fibrosis; celiac disease; and chronic uticaria.

One of skill in the art can easily determine if a subject has an IgE mediated disease by measuring the IgE levels in a biological sample (e.g., blood sample) from the subject or by assessing such symptoms as sneezing, coughing, mucus production, skin irritation, redness, swelling, difficulty breathing, itchiness, among others following exposure to an allergen.

In one embodiment, the IgE mediated disease comprises an allergic disease (e.g., an immune response to an allergen). Some common allergens that produce allergic disease in subjects include e.g., food allergens (e.g., nuts, soy, dairy, gluten, eggs, seafood), pollen (e.g., from grass, trees, weeds), plant product allergens (e.g., poison oak, poison ivy), dust mite excretions (e.g., feces, chitin), animal dander (e.g., cat, dog, rabbit hair), insect stings (e.g., bee, wasp, ant, mosquito), fungus, spores (e.g., mushroom spore), mold, latex, metal, or drugs (e.g., penicillin, sulfonamides).

The Role of IgE in Mediating Allergic Responses

Allergy results when a subject's immune system reacts inappropriately to harmless molecules, such as pollen, dust mite and nuts. In general, allergy is mediated primarily by certain components of the immune system including IgE, mast cells, basophils and eosinophils. IgE is produced by B cells, circulates in the blood and binds to IgE-specific receptors (FcεRI) on the surface of mast cells and basophils. Allergens can then bind to the IgE on the IgE-coated cells. Cross-linking of the IgE and Fc receptors activates the cells, which causes degranulation. Degranulation releases histamine and other inflammatory chemical mediators such as leukocytes and prostaglandins. These mediators cause several systemic effects, such as vasodilation, copious mucus production, and smooth muscle contraction. This results in the runny nose, itchiness, dyspnea, and potentially anaphylaxis associated with allergy. Depending on the individual, allergen, and mode of introduction, the symptoms can be system-wide (classical anaphylaxis), or localized to particular body systems. For example, asthma is localized to the respiratory system and eczema is localized to the skin.

Current Treatment and Management of Chronic Allergic Disease

The continued high burden of allergic disease and increased prevalence of food allergy and asthma indicates suboptimal control despite a variety of pharmacological and non-pharmacological treatments. In general, patients report low satisfaction with allergy treatments. Intranasal corticoid steroids (INCS) are considered the gold-standard for AR but this treatment is associated with bone mineral lost, growth retardation, and adrenal suppression which is troublesome for children. Over the counter (OTC) anti-histamine/decongestants also have adverse effects, such as drowsiness, epistaxis, and burning and have the tendency to stop working. The burden on health care and morbidity associated with allergy warrants the development of new strategies to alleviate chronic allergy.

Current Anti-IgE Therapy

Omalizumab (Xolair) is a humanized monoclonal antibody specific for the region of IgE that binds the high affinity IgE receptor on effector cells (mast cells and basophils). Subcutaneous administration reduces the ability to detect serum IgE within hours and reduces the number of high affinity receptors over 8-12 weeks. Several allergic diseases have been found to respond well to Xolair. Asthma attacks can be reduced 19-75% with Xolair added to corticosteroid therapy. Further, in some studies, patients treated with Xolair were able to reduce their daily corticosteroid dosage or stop use altogether. Xolair is more expensive than other current asthma treatments and health and reimbursement authorities are increasingly demanding evidence of economic benefit to support pricing and formulary listing. Thus, given its high cost, the requirement that it be administered in a physician's office, and side effects, it is appropriate for only a small percentage of patients with asthma. Further, because of the nature of the molecular interaction of this treatment, it can cause anaphylactic shock, a dangerous allergic reaction, in some patients. The methods and compositions described herein offer an effective, low-cost, safe alternative with little side effects, based on a similar mechanism to that of Xolair.

Role of CD23 in Immunity

CD23 has a broad cellular distribution and in addition to B cells, is expressed on monocytes, resting eosinophils, and follicular dendritic cells. CD23 also has multiple ligands other than IgE, including CD21 and Mac-1. CD23 is a type II integral membrane protein with a calcium-dependent lectin domain in the C-terminal end of the extracellular region that binds IgE. A leucine zipper in the N-terminal region allows the CD23 molecules at the cell surface to form homo-trimers which increase the affinity for IgE to the same level as the FcεRI. The C-terminal tail, which "hangs off" the globular lectin head has been shown to bind CD21. There are two isoforms of human CD23: CD23a and CD23b. Without wishing to be bound by theory, both isoforms are thought to be regulated in part by IL-4, but act on separate transcription initiation sites. CD23a and CD23b vary at the N-terminal cytoplasmic region only by a few residues, but possess identical C-terminal extracellular regions. CD23a is expressed primarily by B cells whereas CD23b is inducible by IL-4 and other stimuli on B cells, eosinophils, and monocytes.

Soluble (s)CD23:

sCD23 exists in multiple forms and has numerous effects on the immune system. sCD23 results when surface CD23 (a or b) is proteolytically cleaved thereby releasing the extracellular region into the microenvironment. Endogenous proteases cleave the cell-surface protein near the base of the stalk to release a 37 kDa molecule and at sites closer to the head resulting in several different sized sCD23 fragments. Human serum contains five different molecular weight fragments of monomeric CD23: 37, 33, 29, 25, and 16/17 kDa. The membrane-bound metalloproteinase, ADAM10, catalyzes the cleavage of fragments derived from two distinct sites in the CD23 backbone releasing the 37 and 33 kDa peptides. Neutrophils secrete human leukocyte elastase and cathepsin G, both which efficiently cleave CD23 on B cells. The neutrophil elastase was shown to cleave the 37 kDa fragment into the 25 kDa fragment though the fragment size(s) generated with cathepsin G was not described. The function of sCD23 on subsequent IgE synthesis and cellular activation depends upon whether sCD23 is an oligomer, large or small fragment, and to which ligands it binds (CD23-bound IgE, BCRε, CD21).

Differentially Cleaved Fragments of sCD23 Influence Immunity:

Cleavage of cell surface CD23 in the N-terminal "stalk" by ADAM10 and other proteases generates 29, 33 and 37 kDa fragments that retain the ability to homo-trimerize (or retain the cell surface homotrimer structure). The smaller fragments, 16/17 and 25 kDa, are thought to be generated from the cleavage of the larger molecules by other host cysteine proteases. The level of sCD23 is regulated in part by IL-4 and IgE. Thus, treatment of B cells with IL-4 increases the concentration of sCD23 in supernatants whereas the addition of IgE inhibits the release of sCD23. Even in its soluble form, CD23 has multiple ligands other than IgE, including CD21 (the complement 2 receptor) and Mac-1 and has pleitropic functions. sCD23-containing supernatants derived from B cell cultures induce IgE production in the absence of T cells and IL-4.

Furthermore, sCD23 may rescue B cells from apoptosis by interacting with CD21 and perhaps lower the threshold of B cell receptor-mediated activation through cross-linking CD21. The 25 kDa fragment of sCD23 has been shown to promote differentiation of germinal center B cells by binding to CD21.

sCD23 trimeric clusters have high affinity for BCRε as well and stimulate IgE expression. In a more recent study, three recombinant fragments of CD23 were compared for their ability to stimulate IgE synthesis from anti-CD40/IL-4 activated tonsillar B cells. Monomeric "derCD23" which contains the lectin head and a portion of the C-terminal tail (similar to that released by Derp 1) inhibited IgE synthesis. In contrast, the "lz CD23", which retained the leucine zipper to allow for trimerization, stimulated IgE synthesis. The monomeric "exCD23", which lacked the leucine zipper but retained the full c-terminal tail, could not trimerize, and did not affect IgE production. The authors hypothesized that the lzCD23 was able to induce large networks of cross-linked BCRε and CD21 on the cell surface (FIG. 1) thereby activating the cell.

sCD23 has effects on other cells as well. The 25 kDa protein appears to be pro-inflammatory and induces the secretion of IL-6, IL-1β and TNF-α from monocytes. Soluble fragments released by serine proteases of neutrophils also stimulated resting monocytes to produce oxidative burst and proinflammatory cytokine without any co-stimulatory signal. Several patents relate to the inhibition of production of sCD23 and TNF-α (see e.g., U.S. Pat. Nos. 6,673,965 and 6,235,753).

Further complicating the immunobiology of CD23, CD21 is also found in a soluble form and binds both surface CD23 and sCD23. Soluble CD21 is spontaneously released by B cells upon shedding of the extracellular domain of the molecule. CD23 recognizes two main epitopes on the CD21 molecule. One region consists of short consensus repeat sequences (SCRs) 1-2 and the other of SCRs 5-8 although the effect of CD23 binding to one or either sites on the immune response have not been defined.

Microbial Cleavage of Surface CD23:

Microbial proteases, such as dust mite allergen, Derp1, also cleave CD23. Derp1 is a cysteine protease that cleaves CD23 at two sites (Ser155-Ser156 and Glu298-Ser299) to produce a 16/17-kDa fragment containing the lectin domain and part of the C-terminal tail (amino acids 156-298). This 16/17-kDa fragment contains the minimum structural requirement for binding to both IgE and CD21 but lacks the leucine zipper portion and thus does not oligomerize.

Schistosomes appear to cleave CD23 similarly with the major difference apparent in the CD21 binding properties of the modified molecule. Whereas schistosome generated sCD23 appears to bind IgE, it lacks the ability to bind CD21. The resulting polypeptide is approximately 15 kD. This schistosome-modified CD23 binds to free IgE and likely sequesters it from binding to high affinity receptors on effector cells, such as mast cells. The methods and compositions described herein are based, in part, on these findings. Modified sCD23 represents a viable therapeutic to sequester IgE in a more natural and safe manner to prevent its binding to FcεRI and thus allergic responses.

sCD23 Polypeptide and Peptide Compounds

Peptides or polypeptides useful with the methods described herein comprise modified peptides (or polypeptides) of a soluble form of CD23, and particularly sCD23 polypeptides or peptides that comprise a lectin IgE binding domain but lack a CD21 complement-binding domain. IgE binds to the lectin-head region (including residues from (aa187 to 279), while CD21 appears to involve residues that are separated in both primary structure and tertiary structure (residues 294 and above). Thus, a fragment from 156-292 includes the lectin binding region that is important for binding to IgE but is devoid of the residues required for CD21 interaction.

The CD21-binding tail encompasses amino acids 290 to 321. In one embodiment, a modified sCD23 is a non-CD21 binding protein that lacks amino acids 293-321. CD21 complement binding requires at least amino acids 290-298. Variations of this protein include producing sCD23 lacking any amino acids from 290 to 321. The CD21 domain is a C-terminal domain and at a minimum consists of amino acids 290-298 of SEQ ID NO: 3. In one embodiment, the sCD23 polypeptide comprises SEQ ID NO. 1, 2, 3, 4, 5 or 6. In another embodiment, the sCD23 polypeptide consists essentially of SEQ ID NO. 1, 2, 3, 4, 5 or 6. In another embodiment, the sCD23 polypeptide consists of SEQ ID NO: 1, 2, 3, 4, 5 or 6.

SEQ ID No: 3 illustrated below depicts the lectin IgE binding domain the C-tail CD21 binding domain, and the start of the sCD23 polypeptide.

ments of the methods described herein, the preferred sCD23 fragment is 14-15 kDa and lacks the ability to trimerize and/or to bind CD21. In other embodiments described herein, a high affinity IgE binding sCD23 is preferred for use with the methods described herein (i.e., a D258E mutation of sCD23; SEQ ID No.: 3). Such high affinity binding of sCD23 to IgE enhances the half-life of CD23-IgE complexes by at least 10% compared to non-modified sCD23 fragments. It is contemplated that the preferred sCD23 peptides or polypeptides described herein do not cause inflammation (e.g., by binding CD21 or producing trimers or multimers) and/or can compete for binding sites of the more inflammatory fragments of sCD23, with an overall result of reducing inflammation.

In some embodiments, the level of CD21 binding to an sCD23 polypeptide is reduced. In other embodiments, an sCD23 polypeptide substantially lacks CD21 binding activity. CD21 binding activity can be reduced using any method known to those of skill in the art. For example, the entire

```
                                                      SEQ ID No: 3
MEEGQYSEIE ELPRRRCCRR GTQIVLLGLV TAALWAGLLT LLLLWHWDTT

QSLKQLEERA ARNVSQVSKN LESHHGDQMA QKSQSTQISQ ELEELRAEQQ

RLKSQDLELS WNLNGLQADL SSFKSQELNE RNEASDLLER LREEVTKLRM

ELQVSSGFVC NTCPEKWINF QRKCYYFGKG TKQWVHARYA CDDMEGQLVS

IHSPEEQDFL TKHASHTGSW IGLRNLDLKG EFIWVDGSHV DYSNWAPGEP

TSRSQGEDCV MMRGSGRWND AFCDRKLGAW VCDRLATCTP PASEGSAESM

GPDSRPDPDG RLPTPSAPLH S underlined text = lectin IgE binding domain
italicized text = C-tail CD21 binding domain
bold text = start of common sCD23 polypeptide (172 aa)
```

Human soluble CD34 is modified by schistosomes (a protease cleavage event), which produces a CD23 fragment that binds IgE, but not CD21. This novel CD23 fragment plays an important role in controlling inappropriate IgE mediated immunity in schistosomiasis and that it is the IgE-binding characteristic only that is important. Thus, it is contemplated herein in one embodiment that sCD23 peptides or polypeptides useful with the methods and compositions described herein will bind IgE while lacking substantial CD21 binding.

It is important to note that preferred sCD23 peptides or polypeptides lack a CD21 binding site, since this site likely contributes to the pro-inflammatory activity of some sCD23 polypeptides. For example, it has been previously reported by one group that sCD23 retains the pro-inflammatory properties of the full-length CD23 protein and increases TNF-alpha production (see e.g., Daniels, B. et al., (2005) *Cellular Immunity* 234(2):146-153). Daniels et al. conclude that the "production of proinflammatory cytokines [by sCD23], particularly tumor necrosis factor-α will enhance immune responses in cases of asthma, allergy, and hyper-IgE syndrome." However, Daniels et al. use a recombinant sCD23 150-321 fragment, which contains a CD21-binding domain. Binding of CD21, which is a complement receptor, is most likely the mediator of cytokine production and other inflammatory effects. Additionally, this fragment may trimerize (due to its longer stalk), which can cross-link large networks of CD21 and CD23-bound IgE on the cell surface, thereby activating cells. Further, the sCD23 described by Daniels et al. binds IgE with low affinity. In some embodi- CD21 binding site (e.g., residues 294 and above) can be omitted during synthesis of the polypeptide or cleaved from the sCD23 polypeptide. In other embodiments, one or more amino acid deletions, substitutions, or additions can be utilized to disrupt the binding of CD21 to the sCD23 polypeptide. One of skill in the art can easily test for a disruption of CD21 binding using e.g., an in vitro binding assay or an immunoprecipitation-based assay.

In one aspect, the peptide compound has a formula of $X_1$—$R_0$, wherein $R_0$ comprises SEQ ID No. 4 (or a derivative thereof such as e.g., SEQ ID No. 4 having a D107E mutation) and $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 7). In another embodiment of this aspect, $X_1$ comprises at least 8, at least 9, at least 10, at least 11, at least 12, at least 13, at least 14, at least 15, at least 16, at least 17, at least 18, at least 19, at least 20, at least 22, at least 24, at least 25, at least 27, at least 30, at least 35, at least 37, at least 40, at least 42, at least 45, at least 47, at least 50, at least 55, at least 60, at least 65, at least 70, at least 75, at least 80, at least 85, at least 90, at least 95, at least 100, at least 105, or at least 106 amino acids of SEQ ID NO. 4. For example, $X_1$ can comprise VTKLRM ELQVS (SEQ ID NO: 13). In another embodiment of this aspect, $X_1$ comprises EVTKLRM ELQVS (SEQ ID NO: 14). In another embodiment of this aspect, $X_1$ comprises EEVTKLRM ELQVS (SEQ ID NO: 15). In another embodiment of this aspect, $X_1$ comprises REEVTKLRM ELQVS (SEQ ID NO: 16). In another embodiment of this aspect, $X_1$ comprises LREEVTKLRM ELQVS (SEQ ID NO: 17). In another embodiment of this aspect, $X_1$ comprises R LREEVTKLRM ELQVS (SEQ ID NO: 18). In another embodiment of this aspect, $X_1$ comprises ER LREEVTKLRM ELQVS (SEQ ID NO: 19). In another embodiment of this aspect, $X_1$ comprises LER LREEVTKLRM ELQVS (SEQ ID NO: 20). In another embodiment of this aspect, $X_1$ comprises LLER LREEVTKLRM ELQVS (SEQ ID NO: 21). In another embodiment of this aspect, $X_1$ comprises DLLER LREEVTKLRM ELQVS (SEQ ID NO: 22). In another embodiment of this aspect, $X_1$ comprises SDLLER LREEVTKLRM ELQVS (SEQ ID NO: 23). In another embodiment of this aspect, $X_1$ comprises ASDLLER LREEVTKLRM ELQVS (SEQ ID NO: 24). In another embodiment of this aspect, $X_1$ comprises EASDLLER LREEVTKLRM ELQVS (SEQ ID NO: 25). In another embodiment of this aspect, $X_1$ comprises NEASDLLER LREEVTKLRM ELQVS (SEQ ID NO: 26). In another embodiment of this aspect, $X_1$ comprises RNEASDLLER LREEVTKLRM ELQVS (SEQ ID NO: 27). In another embodiment of this aspect, $X_1$ comprises E RNEASDLLER LREEVTKLRM ELQVS (SEQ ID NO: 28). In another embodiment of this aspect, $X_1$ comprises NE RNEASDLLER LREEVTKLRM ELQVS (SEQ ID NO: 29). In another embodiment of this aspect, $X_1$ comprises LNE RNEASDLLER LREEVTKLRM ELQVS (SEQ ID NO: 30). In another embodiment of this aspect, $X_1$ comprises ELNE RNEASDLLER LREEVTKLRM ELQVS (SEQ ID NO: 31). In another embodiment of this aspect, $X_1$ comprises QELNE RNEASDLLER LREEVTKLRM ELQVS (SEQ ID NO: 32). In another embodiment of this aspect, $X_1$ comprises SQELNE RNEASDLLER LREEVTKLRM ELQVS (SEQ ID NO: 33). In another embodiment of this aspect, $X_1$ comprises KSQELNE RNEASDLLER LREEVTKLRM ELQVS (SEQ ID NO: 34). In another embodiment of this aspect, $X_1$ comprises FKSQELNE RNEASDLLER EEVTKLRM ELQVS (SEQ ID NO: 35). In another embodiment of this aspect, $X_1$ comprises SFKSQELNE RNEASDLLER LREEVTKLRM ELQVS (SEQ ID NO: 36). In another embodiment of this aspect, $X_1$ comprises SSFKSQELNE RNEASDLLER LREEVTKLRM ELQVS (SEQ ID NO: 37). In another embodiment of this aspect, $X_1$ comprises L SSFKSQELNE RNEASDLLER LREEVTKLRM ELQVS (SEQ ID NO: 38). In another embodiment of this aspect, $X_1$ comprises DL SSFKSQELNE RNEASDLLER LREEVTKLRM ELQVS (SEQ ID NO: 39). In another embodiment of this aspect, $X_1$ comprises ADL SSFKSQELNE RNEASDLLER LREEVTKLRM ELQVS (SEQ ID NO: 40). In another embodiment of this aspect, $X_1$ comprises QADL SSFKSQELNE RNEASDLLER LREEVTKLRM ELQVS (SEQ ID NO: 41). In another embodiment of this aspect, $X_1$ comprises LQADL SSFKSQELNE RNEASDLLER LREEVTKLRM ELQVS (SEQ ID NO: 42). In another embodiment of this aspect, $X_1$ comprises GLQADL SSFKSQELNE RNEASDLLER LREEVTKLRM ELQVS (SEQ ID NO: 43). In another embodiment of this aspect, $X_1$ comprises NGLQADL SSFKSQELNE RNEASDLLER LREEVTKLRM ELQVS (SEQ ID NO: 44). In another embodiment of this aspect, $X_1$ comprises LNGLQADL SSFKSQELNE RNEASDLLER LREEVTKLRM ELQVS (SEQ ID NO: 45). In another embodiment of this aspect, $X_1$ comprises NLNGLQADL SSFKSQELNE RNEASDLLER LREEVTKLRM ELQVS (SEQ ID NO: 46). In another embodiment of this aspect, $X_1$ comprises WNLNGLQADL SSFKSQELNE RNEASDLLER LREEVTKLRM ELQVS (SEQ ID NO: 47). In another embodiment of this aspect, $X_1$ comprises S WNLNGLQADL SSFKSQELNE RNEASDLLER LREEVTKLRM ELQVS (SEQ ID NO: 48). In another embodiment of this aspect, $X_1$ comprises LS WNLNGLQADL SSFKSQELNE RNEASDLLER LREEVTKLRM ELQVS (SEQ ID NO: 49). In another embodiment of this aspect, $X_1$ comprises ELS WNLNGLQADL SSFKSQELNE RNEASDLLER LREEVTKLRM ELQVS (SEQ ID NO: 50). In another embodiment of this aspect, $X_1$ comprises LELS WNLNGLQADL SSFKSQELNE RNEASDLLER LREEVTKLRM ELQVS (SEQ ID NO: 51). In another embodiment of this aspect, $X_1$ comprises DLELS WNLNGLQADL SSFKSQELNE RNEASDLLER LREEVTKLRM ELQVS (SEQ ID NO: 52). In another embodiment of this aspect, $X_1$ comprises QDLELS WNLNGLQADL SSFKSQELNE RNEASDLLER LREEVTKLRM ELQVS (SEQ ID NO: 53). In another embodiment of this aspect, $X_1$ comprises SQDLELS WNLNGLQADL SSFKSQELNE RNEASDLLER LREEVTKLRM ELQVS (SEQ ID NO: 54). In another embodiment of this aspect, $X_1$ comprises KSQDLELS WNLNGLQADL SSFKSQELNE RNEASDLLER LREEVTKLRM ELQVS (SEQ ID NO: 55). In another embodiment of this aspect, $X_1$ comprises LKSQDLELS WNLNGLQADL SSFKSQELNE RNEASDLLER LREEVTKLRM ELQVS (SEQ ID NO: 56). In another embodiment of this aspect, $X_1$ comprises RLKSQDLELS WNLNGLQADL SSFKSQELNE RNEASDLLER LREEVTKLRM ELQVS (SEQ ID NO: 57). In another embodiment of this aspect, $X_1$ comprises Q RLKSQDLELS WNLNGLQADL SSFKSQELNE RNEASDLLER LREEVTKLRM ELQVS (SEQ ID NO: 58). In another embodiment of this aspect, $X_1$ comprises QQ RLKSQDLELS WNLNGLQADL SSFKSQELNE RNEASDLLER LREEVTKLRM ELQVS (SEQ ID NO: 59). In another embodiment of this aspect, $X_1$ comprises EQQ RLKSQDLELS WNLNGLQADL SSFKSQELNE RNEASDLLER LREEVTKLRM ELQVS (SEQ ID NO: 60). In another embodiment of this aspect, $X_1$ comprises AEQQ RLKSQDLELS WNLNGLQADL SSFKSQELNE RNEASDLLER LREEVTKLRM ELQVS (SEQ ID NO: 61). In another embodiment of this aspect, $X_1$ comprises RAEQQ RLKSQDLELS WNLNGLQADL SSFKSQELNE RNEASDLLER LREEVTKLRM ELQVS (SEQ ID NO: 62). In another embodiment of this aspect, $X_1$ comprises LRAEQQ RLKSQDLELS WNLNGLQADL SSFKSQELNE RNEASDLLER LREEVTKLRM ELQVS (SEQ ID NO: 63). In another embodiment of this aspect, $X_1$ comprises ELRAEQQ RLKSQDLELS WNLNGLQADL SSFKSQELNE RNEASDLLER LREEVTKLRM ELQVS (SEQ ID NO: 64). In another embodiment of this aspect, $X_1$ comprises EELRAEQQ RLKSQDLELS WNLNGLQADL SSFKSQELNE RNEASDLLER LREEVTKLRM ELQVS (SEQ ID NO: 65). In another embodiment of this aspect, $X_1$ comprises LEELRAEQQ RLKSQDLELS WNLNGLQADL SSFKSQELNE RNEASDLLER LREEVTKLRM ELQVS (SEQ ID NO: 66). In another embodiment of this aspect, $X_1$ comprises ELEELRAEQQ RLKSQDLELS WNLNGLQADL SSFKSQELNE RNEASDLLER LREEVTKLRM ELQVS (SEQ ID NO: 67). In another embodiment of this aspect, $X_1$ comprises Q ELEELRAEQQ RLKSQDLELS WNLNGLQADL SSFKSQELNE RNEASDLLER LREEVTKLRM ELQVS (SEQ ID NO: 68). In another embodiment of this aspect, $X_1$ comprises SQ ELEELRAEQQ RLKSQDLELS WNLNGLQADL SSFKSQELNE RNEASDLLER LREEVTKLRM ELQVS (SEQ ID NO: 69). In another embodiment of this aspect, $X_1$ comprises ISQ ELEELRAEQQ RLKSQDLELS WNLNGLQADL SSFKSQELNE RNEASDLLER LREEVTKLRM ELQVS (SEQ ID NO: 70). In another embodiment of this aspect, $X_1$ comprises QISQ ELEELRAEQQ RLKSQDLELS WNLNGLQADL SSFKSQELNE RNEASDLLER LREEVTKLRM ELQVS (SEQ ID NO: 71). In another embodiment of this aspect, $X_1$ comprises TQISQ ELEELRAEQQ RLKSQDLELS WNLNGLQADL SSFKSQELNE RNEASDLLER LREEVTKLRM ELQVS (SEQ ID NO: 72). In another embodiment of this aspect, $X_1$ comprises STQISQ ELEELRAEQQ RLKSQDLELS WNLNGLQADL SSFKSQELNE RNEASDLLER LREEVTKLRM ELQVS (SEQ ID NO: 73). In another embodiment of this aspect, $X_1$ comprises QSTQISQ ELEELRAEQQ RLKSQDLELS WNLNGLQADL SSFKSQELNE RNEASDLLER LREEVTKLRM ELQVS (SEQ ID NO: 74). In another embodiment of this aspect, $X_1$ comprises SQSTQISQ ELEELRAEQQ RLKSQDLELS WNLNGLQADL SSFKSQELNE RNEASDLLER LREEVTKLRM ELQVS (SEQ ID NO: 75). In another embodiment of this aspect, $X_1$ comprises KSQSTQISQ ELEELRAEQQ RLKSQDLELS WNLNGLQADL SSFKSQELNE RNEASDLLER LREEVTKLRM ELQVS (SEQ ID NO: 76). In another embodiment of this aspect, $X_1$ comprises QKSQSTQISQ ELEELRAEQQ RLKSQDLELS WNLNGLQADL SSFKSQELNE RNEASDLLER LREEVTKLRM ELQVS (SEQ ID NO: 77). In another embodiment of this aspect, $X_1$ comprises A QKSQSTQISQ ELEELRAEQQ RLKSQDLELS WNLNGLQADL SSFKSQELNE RNEASDLLER LREEVTKLRM ELQVS (SEQ ID NO: 78). In another embodiment of this aspect, $X_1$ comprises MA QKSQSTQISQ ELEELRAEQQ RLKSQDLELS WNLNGLQADL SSFKSQELNE RNEASDLLER LREEVTKLRM ELQVS (SEQ ID NO: 79). In another embodiment of this aspect, $X_1$ comprises QMA QKSQSTQISQ ELEELRAEQQ RLKSQDLELS WNLNGLQADL SSFKSQELNE RNEASDLLER LREEVTKLRM ELQVS (SEQ ID NO: 80). In another embodiment of this aspect, $X_1$ comprises DQMA QKSQSTQISQ ELEELRAEQQ RLKSQDLELS WNLNGLQADL SSFKSQELNE RNEASDLLER LREEVTKLRM ELQVS (SEQ ID NO: 81). In another embodiment of this aspect, $X_1$ comprises GDQMA QKSQSTQISQ ELEELRAEQQ RLKSQDLELS WNLNGLQADL SSFKSQELNE RNEASDLLER LREEVTKLRM ELQVS (SEQ ID NO: 82). In another embodiment of this aspect, $X_1$ comprises HGDQMA QKSQSTQISQ ELEELRAEQQ RLKSQDLELS WNLNGLQADL SSFKSQELNE RNEASDLLER LREEVTKLRM ELQVS (SEQ ID NO: 83). In another embodiment of this aspect, $X_1$ comprises HHGDQMA QKSQSTQISQ ELEELRAEQQ RLKSQDLELS WNLNGLQADL SSFKSQELNE RNEASDLLER LREEVTKLRM ELQVS (SEQ ID NO: 84). In another embodiment of this aspect, $X_1$ comprises SHHGDQMA QKSQSTQISQ ELEELRAEQQ RLKSQDLELS WNLNGLQADL SSFKSQELNE RNEASDLLER LREEVTKLRM ELQVS (SEQ ID NO: 85). In another embodiment of this aspect, $X_1$ comprises ESHHGDQMA QKSQSTQISQ ELEELRAEQQ RLKSQDLELS WNLNGLQADL SSFKSQELNE RNEASDLLER LREEVTKLRM ELQVS (SEQ ID NO: 86). In another embodiment of this aspect, $X_1$ comprises LESHHGDQMA QKSQSTQISQ ELEELRAEQQ RLKSQDLELS WNLNGLQADL SSFKSQELNE RNEASDLLER LREEVTKLRM ELQVS (SEQ ID NO: 87).

In another embodiment of this aspect, $X_1$ comprises N LESHHGDQMA QKSQSTQISQ ELEELRAEQQ RLKSQDLELS WNLNGLQADL SSFKSQELNE RNEASDLLER LREEVTKLRM ELQVS (SEQ ID NO: 88). In another embodiment of this aspect, $X_1$ comprises KN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 89). In another embodiment of this aspect, $X_1$ comprises SKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 90). In another embodiment of this aspect, $X_1$ comprises VSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 91). In another embodiment of this aspect, $X_1$ comprises QVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 92). In another embodiment of this aspect, $X_1$ comprises SQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 93). In another embodiment of this aspect, $X_1$ comprises VSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 94). In another embodiment of this aspect, $X_1$ comprises NVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 95). In another embodiment of this aspect, $X_1$ comprises RNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 96). In another embodiment of this aspect, $X_1$ comprises ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 97). In another embodiment of this aspect, $X_1$ comprises A ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 98). In another embodiment of this aspect, $X_1$ comprises RA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 99). In another embodiment of this aspect, $X_1$ comprises ERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 100). In another embodiment of this aspect, $X_1$ comprises EERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 101). In another embodiment of this aspect, $X_1$ comprises LEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 102). In another embodiment of this aspect, $X_1$ comprises QLEERA ARNVSQVSKN LESHHGDQMA QKSQSTQ- ISQ ELEELRAEQQ RLKSQDLELS WNLNGLQADL SSFKSQELNE RNEASDLLER LREEVTKLRM ELQVS (SEQ ID NO: 103). In another embodiment of this aspect, $X_1$ comprises KQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 104). In another embodiment of this aspect, $X_1$ comprises LKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 105). In another embodiment of this aspect, $X_1$ comprises SLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 106). In another embodiment of this aspect, $X_1$ comprises QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 107). In another embodiment of this aspect, $X_1$ comprises T QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 108). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQV (SEQ ID NO: 109). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQ (SEQ ID NO: 110).

In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM EL (SEQ ID NO: 111). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM E (SEQ ID NO: 112). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM (SEQ ID NO: 113). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLR (SEQ ID NO: 114). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKL (SEQ ID NO: 115). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTK (SEQ ID NO: 116). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LREEVT (SEQ ID NO: 117). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LREEV (SEQ ID NO: 118). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LREE (SEQ ID NO: 119). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LRE (SEQ ID NO: 120). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER LR (SEQ ID NO: 121). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER L (SEQ ID NO: 122). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLER (SEQ ID NO: 123). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLLE (SEQ ID NO: 124). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDLL (SEQ ID NO: 125). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASDL (SEQ ID NO: 126). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEASD (SEQ ID NO: 127). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEAS (SEQ ID NO: 128). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNEA (SEQ ID NO: 129). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RNE (SEQ ID NO: 130). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE RN (SEQ ID NO: 131). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE R (SEQ ID NO: 132). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELNE (SEQ ID NO: 133). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQELN (SEQ ID NO: 134). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQEL (SEQ ID NO: 135). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQE (SEQ ID NO: 136). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKSQ (SEQ ID NO: 137). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFKS (SEQ ID NO: 138). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSFK (SEQ ID NO: 139). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SSF (SEQ ID NO: 140). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL SS (SEQ ID NO: 141). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL S (SEQ ID NO: 142). In another embodiment of this aspect, $X_1$ comprises TT QSLKQLEERA ARNVSQVSKN LESHHGDQMA QKSQSTQISQ ELEELRAEQQ RLKSQDLELS WNLNGLQADL (SEQ ID NO: 143). In another embodiment of this aspect, $X_1$ comprises TT QSLKQLEERA ARNVSQVSKN LESHHGDQMA QKSQSTQISQ ELEELRAEQQ RLKSQDLELS WNLNGLQAD (SEQ ID NO: 144). In another embodiment of this aspect, $X_1$ comprises TT QSLKQLEERA ARNVSQVSKN LESHHGDQMA QKSQSTQISQ ELEELRAEQQ RLKSQDLELS WNLNGLQA (SEQ ID NO: 145). In another embodiment of this aspect, $X_1$ comprises TT QSLKQLEERA ARNVSQVSKN LESHHGDQMA QKSQSTQISQ ELEELRAEQQ RLKSQDLELS WNLNGLQ (SEQ ID NO: 146). In another embodiment of this aspect, $X_1$ comprises TT QSLKQLEERA ARNVSQVSKN LESHHGDQMA QKSQSTQISQ ELEELRAEQQ RLKSQDLELS WNLNGL (SEQ ID NO: 147). In another embodiment of this aspect, $X_1$ comprises TT QSLKQLEERA ARNVSQVSKN LESHHGDQMA QKSQSTQISQ ELEELRAEQQ RLKSQDLELS WNLNG (SEQ ID NO: 148). In another embodiment of this aspect, $X_1$ comprises TT QSLKQLEERA ARNVSQVSKN LESHHGDQMA QKSQSTQISQ ELEELRAEQQ RLKSQDLELS WNLN (SEQ ID NO: 149). In another embodiment of this aspect, $X_1$ comprises TT QSLKQLEERA ARNVSQVSKN LESHHGDQMA QKSQSTQISQ ELEELRAEQQ RLKSQDLELS WNL (SEQ ID NO: 150). In another embodiment of this aspect, $X_1$ comprises TT QSLKQLEERA ARNVSQVSKN LESHHGDQMA QKSQSTQISQ ELEELRAEQQ RLKSQDLELS WN (SEQ ID NO: 151). In another embodiment of this aspect, $X_1$ comprises TT QSLKQLEERA ARNVSQVSKN LESHHGDQMA QKSQSTQISQ ELEELRAEQQ RLKSQDLELS W (SEQ ID NO: 152). In another embodiment of this aspect, $X_1$ comprises TT QSLKQLEERA ARNVSQVSKN LESHHGDQMA QKSQSTQISQ ELEELRAEQQ RLKSQDLELS (SEQ ID NO: 153). In another embodiment of this aspect, $X_1$ comprises TT QSLKQLEERA ARNVSQVSKN LESHHGDQMA QKSQSTQISQ ELEELRAEQQ RLKSQDLEL (SEQ ID NO: 154). In another embodiment of this aspect, $X_1$ comprises TT QSLKQLEERA ARNVSQVSKN LESHHGDQMA QKSQSTQISQ ELEELRAEQQ RLKSQDLE (SEQ ID NO: 155). In another embodiment of this aspect, $X_1$ comprises TT QSLKQLEERA ARNVSQVSKN LESHHGDQMA QKSQSTQISQ ELEELRAEQQ RLKSQDL (SEQ ID NO: 156). In another embodiment of this aspect, $X_1$ comprises TT QSLKQLEERA ARNVSQVSKN LESHHGDQMA QKSQSTQISQ ELEELRAEQQ RLKSQD (SEQ ID NO: 157). In another embodiment of this aspect, $X_1$ comprises TT QSLKQLEERA ARNVSQVSKN LESHHGDQMA QKSQSTQISQ ELEELRAEQQ RLKSQ (SEQ ID NO: 158). In another embodiment of this aspect, $X_1$ comprises TT QSLKQLEERA ARNVSQVSKN LESHHGDQMA QKSQSTQISQ ELEELRAEQQ RLKS (SEQ ID NO: 159). In another embodiment of this aspect, $X_1$ comprises TT QSLKQLEERA ARNVSQVSKN LESHHGDQMA QKSQSTQISQ ELEELRAEQQ RLK (SEQ ID NO: 160). In another embodiment of this aspect, $X_1$ comprises TT QSLKQLEERA ARNVSQVSKN LESHHGDQMA QKSQSTQISQ ELEELRAEQQ RL (SEQ ID NO: 161). In another embodiment of this aspect, $X_1$ comprises TT QSLKQLEERA ARNVSQVSKN LESHHGDQMA QKSQSTQISQ ELEELRAEQQ R (SEQ ID NO: 162). In another embodiment of this aspect, $X_1$ comprises TT QSLKQLEERA ARNVSQVSKN LESHHGDQMA QKSQSTQISQ ELEELRAEQQ (SEQ ID NO: 163). In another embodiment of this aspect, $X_1$ comprises TT QSLKQLEERA ARNVSQVSKN LESHHGDQMA QKSQSTQISQ ELEELRAEQ (SEQ ID NO: 164). In another embodiment of this aspect, $X_1$ comprises TT QSLKQLEERA ARNVSQVSKN LESHHGDQMA QKSQSTQISQ ELEELRAE (SEQ ID NO: 165). In another embodiment of this aspect, $X_1$ comprises TT QSLKQLEERA ARNVSQVSKN LESHHGDQMA QKSQSTQISQ ELEELRA (SEQ ID NO: 166). In another embodiment of this aspect, $X_1$ comprises TT QSLKQLEERA ARNVSQVSKN LESHHGDQMA QKSQSTQISQ ELEELR (SEQ ID NO: 167). In another embodiment of this aspect, $X_1$ comprises TT QSLKQLEERA ARNVSQVSKN LESHHGDQMA QKSQSTQISQ ELEEL (SEQ ID NO: 168). In another embodiment of this aspect, $X_1$ comprises TT QSLKQLEERA ARNVSQVSKN LESHHGDQMA QKSQSTQISQ ELEE (SEQ ID NO: 169). In another embodiment of this aspect, $X_1$ comprises TT QSLKQLEERA ARNVSQVSKN LESHHGDQMA QKSQSTQISQ ELE (SEQ ID NO: 170). In another embodiment of this aspect, $X_1$ comprises TT QSLKQLEERA ARNVSQVSKN LESHHGDQMA QKSQSTQISQ EL (SEQ ID NO: 171). In another embodiment of this aspect, $X_1$ comprises TT QSLKQLEERA ARNVSQVSKN LESHHGDQMA QKSQSTQISQ E (SEQ ID NO: 172). In another embodiment of this aspect, $X_1$ comprises TT QSLKQLEERA ARNVSQVSKN LESHHGDQMA QKSQSTQISQ (SEQ ID NO: 173). In another embodiment of this aspect, $X_1$ comprises TT QSLKQLEERA ARNVSQVSKN LESHHGDQMA QKSQSTQIS (SEQ ID NO: 174). In another embodiment of this aspect, $X_1$ comprises TT QSLKQLEERA ARNVSQVSKN LESHHGDQMA QKSQSTQI (SEQ ID NO: 175). In another embodiment of this aspect, $X_1$ comprises TT QSLKQLEERA ARNVSQVSKN LESHHGDQMA QKSQSTQ (SEQ ID NO: 176). In another embodiment of this aspect, $X_1$ comprises TT QSLKQLEERA ARNVSQVSKN LESHHGDQMA QKSQST (SEQ ID NO: 177). In another embodiment of this aspect, $X_1$ comprises TT QSLKQLEERA ARNVSQVSKN LESHHGDQMA QKSQS (SEQ ID NO: 178). In another embodiment of this aspect, $X_1$ comprises TT QSLKQLEERA ARNVSQVSKN LESHHGDQMA QKSQ (SEQ ID NO: 179). In another embodiment of this aspect, $X_1$ comprises TT QSLKQLEERA ARNVSQVSKN LESHHGDQMA QKS (SEQ ID NO: 180). In another embodiment of this aspect, $X_1$ comprises TT QSLKQLEERA ARNVSQVSKN LESHHGDQMA QK (SEQ ID NO: 181). In another embodiment of this aspect, $X_1$ comprises TT QSLKQLEERA ARNVSQVSKN LESHHGDQMA Q (SEQ ID NO: 182). In another embodiment of this aspect, $X_1$ comprises TT QSLKQLEERA ARNVSQVSKN LESHHGDQMA (SEQ ID NO: 183). In another embodiment of this aspect, $X_1$ comprises TT QSLKQLEERA ARNVSQVSKN LESHHGDQMA Q (SEQ ID NO: 184). In another embodiment of this aspect, $X_1$ comprises TT QSLKQLEERA ARNVSQVSKN LESHHGDQM (SEQ ID NO: 185). In another embodiment of this aspect, $X_1$ comprises TT QSLKQLEERA ARNVSQVSKN LESHHGDQMA Q (SEQ ID NO: 186). In another embodiment of this aspect, $X_1$ comprises TT QSLKQLEERA ARNVSQVSKN LESHHGDQM (SEQ ID NO: 187). In another embodiment of this aspect, $X_1$ comprises TT QSLKQLEERA ARNVSQVSKN LESHHGDQ (SEQ ID NO: 188). In another embodiment of this aspect, $X_1$ comprises TT QSLKQLEERA ARNVSQVSKN LESHHGD (SEQ ID NO: 189). In another embodiment of this aspect, $X_1$ comprises TT QSLKQLEERA ARNVSQVSKN LESHHGDQMA Q (SEQ ID NO: 190). In another embodiment of this aspect, $X_1$ comprises TT QSLKQLEERA ARNVSQVSKN LESHHG (SEQ ID NO: 191). In another embodiment of this aspect, $X_1$ comprises TT QSLKQLEERA ARNVSQVSKN LESHHGDQMA Q (SEQ ID NO: 192). In another embodiment of this aspect, $X_1$ comprises TT QSLKQLEERA ARNVSQVSKN LESHH (SEQ ID NO: 193). In another embodiment of this aspect, $X_1$ comprises TT QSLKQLEERA ARNVSQVSKN LESH (SEQ ID NO: 194). In another embodiment of this aspect, $X_1$ comprises TT QSLKQLEERA ARNVSQVSKN LES (SEQ ID NO: 195). In another embodiment of this aspect, $X_1$ comprises TT QSLKQLEERA ARNVSQVSKN LE (SEQ ID NO: 196). In another embodiment of this aspect, $X_1$ comprises TT QSLKQLEERA ARNVSQVSKN L (SEQ ID NO: 197). In another embodiment of this aspect, $X_1$ comprises TT QSLKQLEERA ARNVSQVSKN (SEQ ID NO: 198). In another embodiment of this aspect, $X_1$ comprises TT QSLKQLEERA ARNVSQVSK (SEQ ID NO: 199). In another embodiment of this aspect, $X_1$ comprises TT QSLKQLEERA ARNVSQVS (SEQ ID NO: 200). In another embodiment of this aspect, $X_1$ comprises TT QSLKQLEERA ARNVSQV (SEQ ID NO: 201). In another embodiment of this aspect, $X_1$ comprises TT QSLKQLEERA ARNVSQ (SEQ ID NO: 202). In another embodiment of this aspect, $X_1$ comprises TT QSLKQLEERA ARNVS (SEQ ID NO: 203). In another embodiment of this aspect, $X_1$ comprises TT QSLKQLEERA ARNV (SEQ ID NO: 204). In another embodiment of this aspect, $X_1$ comprises TT QSLKQLEERA ARN (SEQ ID NO: 205). In another embodiment of this aspect, $X_1$ comprises TT QSLKQLEERA AR (SEQ ID NO: 206). In another embodiment of this aspect, $X_1$ comprises TT QSLKQLEERA A (SEQ ID NO: 207). In another embodiment of this aspect, $X_1$ comprises TT QSLKQLEERA (SEQ ID NO: 208). In another embodiment of this aspect, $X_1$ comprises TT QSLKQLEER (SEQ ID NO: 209).

In some embodiments, conservative amino acid substitutions as set forth in Table 1 are permitted.

In another aspect, the compound has a formula of $R_0$—$X_2$, wherein $R_0$ comprises SEQ ID No. 4 (or a derivative thereof such as e.g., SEQ ID No. 4 having a D107E mutation) and $X_2$ comprises SEGSAE (SEQ ID NO: 9). In one embodiment of this aspect, $X_2$ comprises the amino acid sequence AE. In another embodiment of this aspect, $X_2$ comprises EGSAE (SEQ ID NO: 210). In another embodiment of this aspect, $X_2$ comprises GSAE (SEQ ID NO: 211). In another embodiment of this aspect, $X_2$ comprises SAE. In another embodiment of this aspect, $X_2$ comprises E. In other embodiments of this aspect, $X_2$ can be —$CONH_2$, —COOH, $NH_2$, $C_1$-$C_{10}$ alkylamino, di($C_1$-$C_{10}$ alkyl)amino, amino-$C_1$-$C_{10}$ alkylamino, or di(amino $C_1$-$C_{10}$ alkyl)amino, $NH(CH_2)$ NH wherein n is 1 to 8, or —OH. In another embodiment of this aspect.

In another embodiment of the aspects described above, the D at position 107 of $R_0$ (SEQ ID No. 4) is modified to an E. In other embodiments of the aspects described above, the compounds comprise at least one additional $R_n$ group (e.g., $R_1$, $R_2$, $R_3$, $R_4$, $R_5$, $R_6$ etc) between $X_1$ and $R_0$ or between $X_2$ and $R_0$, wherein $R_n$ comprises any natural L-amino acid, Pal, αNal, βNal, DpCl, CHx, where CHx is cyclohexyl, CHxAla or any of their respective D-isomers; a halogen, diisobutylamide, dipropylamide, butylamide, pentylamide, dipentylamide, DPro, DPro-DPro, DVal, or DTrp. In one embodiment, the compound has the formula $X_1$—$R_0$—$X_2$, wherein $X_1$, $R_0$, and $X_2$ are as described above. $X_1$ and $X_2$ can have conservative amino acid substitutions as set forth in Table 1. $R_0$ can also have the substitutions set forth in Table 1. The compound can also have the formula $R_0$. In one embodiment, the compound comprises the formula $R_0$ with an amino acid substitution at position 107 of SEQ ID No:4/position 258 of sCD23 (SEQ ID No:3), for example the polypeptide of formula SEQ ID No:2. The D residue can be substituted for any natural L-amino acid, a D-amino acid, or amino acid analogue as known in the art. In one embodiment, the D residue at position 258 of SEQ ID No.3 (highlighted residue) is substituted with an E residue. As disclosed, infra, these compounds can be PEGylated.

Also contemplated herein are conservative amino acid substitutions of the sCD23 peptide or polypeptide. The terminology "conservative amino acid substitutions" is well known in the art, which relates to substitution of a particular amino acid by one having a similar characteristic (e.g., similar charge or hydrophobicity, similar bulkiness). Examples include aspartic acid for glutamic acid, or isoleucine for leucine. A list of exemplary conservative amino acid substitutions is given in the table below. A conservative substitution mutant or variant will 1) have only conservative amino acid substitutions relative to the parent sequence, 2) will have at least 90% sequence identity with respect to the parent sequence, preferably at least 95% identity, 96% identity, 97% identity, 98% identity or 99% or greater identity; and 3) will retain sCD23 activity (e.g., IgE binding activity) as that term is defined herein.

TABLE 1

CONSERVATIVE AMINO ACID SUBSTITUTIONS

| For Amino Acid | Code | Replace With |
|---|---|---|
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. (4,511,390) |
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

An sCD23 peptide, polypeptide, or variant or derivative thereof can be produced chemically by e.g., solution or solid-phase peptide synthesis, or semi-synthesis in solution beginning with protein fragments coupled through conventional solution methods, as described by Dugas et al (1981). Alternatively, an sCD23 peptide or polypeptide can be synthesized using e.g., recombinant methods.

A sCD23 peptide or polypeptide can be chemically synthesized, for example, by the solid phase peptide synthesis of Merrifield et al (1964). Alternatively, a peptide or polypeptide can be synthesized using standard solution methods (see, for example, Bodanszky, 1984). Newly synthesized peptides can be purified, for example, by high performance liquid chromatography (HPLC), and can be characterized using, for example, mass spectrometry or amino acid sequence analysis.

In one embodiment, the sCD23 peptide or polypeptide is produced recombinantly. Systems for cloning and expressing polypeptides useful with the methods and compositions described herein include various microorganisms and cells that are well known in recombinant technology. These include, for example, various strains of E. coli, Bacillus, Streptomyces, and Saccharomyces, as well as mammalian, yeast and insect cells. An sCD23 peptide or polypeptide can be produced as a peptide or fusion protein. Suitable vectors for producing peptides and polypeptides are known and available from private and public laboratories and depositories and from commercial vendors. See Sambrook et al, (1989). Recipient cells capable of expressing the gene product are then transfected. The transfected recipient cells are cultured under conditions that permit expression of the recombinant gene products, which are recovered from the culture. Host mammalian cells, such as Chinese Hamster ovary cells (CHO) or COS-1 cells, can be used. These hosts can be used in connection with poxvirus vectors, such as vaccinia or swinepox. Suitable non-pathogenic viruses that can be engineered to carry the synthetic gene into the cells of the host include poxviruses, such as vaccinia, adenovirus, retroviruses and the like. A number of such non-pathogenic viruses are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques (see, e.g., Gething et al, 1981).

Native CD23 is a homotrimer, which permits high affinity binding of IgE. In some embodiments it is contemplated herein that a sCD23 compound used herein is a homodimer, homotrimer, homo-multimer, a hetero-dimer, a heterotrimer, or a hetero-multimer.

In other embodiments, the sCD23 compound used herein is a monomer.

In one embodiment a sCD23 peptide or polypeptide is isolated and/or purified. Protein purification techniques are well known to those of skill in the art. These techniques involve, at one level, the homogenization and crude fractionation of the cells, tissue or organ to polypeptide and non-polypeptide fractions. The sCD23 peptide or polypeptide of interest may be further purified using chromatographic and electrophoretic techniques to achieve partial or complete purification (or purification to homogeneity). Analytical methods particularly suited to the preparation of a pure peptide or polypeptide are ion-exchange chromatography, gel exclusion chromatography, polyacrylamide gel electrophoresis, affinity chromatography, immunoaffinity chromatography and isoelectric focusing. An example of receptor protein purification by affinity chromatography is disclosed in U.S. Pat. No. 5,206,347, the entire text of which is incorporated herein by reference. A particularly efficient method of purifying peptides/polypeptides is fast performance liquid chromatography (FPLC) or even high performance liquid chromatography (HPLC).

A purified sCD23 peptide/polypeptide is intended to refer to a composition, isolatable from other components, wherein the sCD23 peptide/polypeptide is purified to any degree relative to the organism producing recombinant protein or in its naturally-obtainable state. An isolated or purified peptide or polypeptide, therefore, also refers to a peptide/polypeptide free from the environment in which it may naturally occur. Generally, "purified" will refer to a sCD23 peptide/polypeptide composition that has been subjected to fractionation to remove various other components, and which composition substantially retains its expressed biological activity. Where the term "substantially purified" is used, this designation will refer to a composition in which the sCD23 peptide/polypeptide forms the major component of the composition, such as constituting about 50%, about 60%, about 70%, about 80%, about 90%, about 95%, or more of the proteins in the composition.

Various methods for quantifying the degree of purification of a sCD23 peptide/polypeptide are known to those of skill in the art and include, for example, determining the specific activity of an active fraction, or assessing the amount of polypeptides within a fraction by SDS/PAGE analysis Various techniques suitable for use in protein purification are known to those of skill in the art and include, for example, precipitation with ammonium sulfate, polyethylene glycol (PEG), antibodies and the like, or by heat denaturation, followed by: centrifugation; chromatography steps such as ion exchange, gel filtration, reverse phase, hydroxyapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the sCD23 peptide or polypeptide be provided in the most purified state. Indeed, it is contemplated that less purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind (e.g., a receptor-ligand interaction). The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding And it should be possible to elute the substance without destroying the sample or the ligand.

Peptides, Polypeptides and Modifications Thereof

A sCD23 peptide/polypeptide functional to sequester IgE can be administered directly to a subject in need thereof. In one approach, a sCD23 peptide or polypeptide, produced, for example, in cultured cells bearing a recombinant sCD23 expression vector can be administered to the subject. The sCD23 compound will generally be administered intravenously or directly into the site of excess IgE in a subject e.g., by inhalation. This approach rapidly delivers the protein to the lungs and maximizes the chance that the protein is intact when delivered. Further options for the delivery of sCD23 peptides/polypeptides as described herein are discussed in the section "Pharmaceutical Compositions" herein below.

In one embodiment, the protein or fragment thereof is linked to a carrier to enhance its bioavailability. Such carriers are known in the art and include poly(alkyl)glycol such as poly ethylene glycol (PEG). Fusion to serum albumin can also increase the serum half-life of therapeutic polypeptides.

Vectors for transduction of a sCD23-encoding sequence are well known in the art. While overexpression using a strong non-specific promoter, such as a CMV promoter, can be used, it can be helpful to include a tissue- or cell-type-specific promoter on the expression construct for example, the use of an immune cell-specific promoter (e.g., interleukin promoter or TNF-α promoter) or other cell-type-specific promoter can be advantageous, depending upon what cell type is used as a host. Further, treatment can include the administration of viral vectors that drive the expression of sCD23 peptides or polypeptides in infected host cells. Viral vectors are well known to those skilled in the art.

The vectors are readily adapted for use in the methods of the present invention. By the appropriate manipulation using recombinant DNA/molecular biology techniques to insert an operatively linked sCD23-encoding nucleic acid segment into the selected expression/delivery vector, many equivalent vectors for the practice of the methods described herein can be generated. It will be appreciated by those of skill in the art that cloned genes readily can be manipulated to alter the amino acid sequence of a protein.

The sCD23 peptide or polypeptide can also be a fusion peptide/polypeptide, fused, for example, to a polypeptide that targets the product to a desired location, or, for example, a tag that facilitates its purification, if so desired. Fusion to a polypeptide sequence that increases the stability of the sCD23 compound is also contemplated. For example, fusion to a serum protein, e.g., serum albumin, can increase the circulating half-life of a sCD23 peptide or polypeptide. Tags and fusion partners can be designed to be cleavable, if so desired. Another modification specifically contemplated is attachment, e.g., covalent attachment, to a polymer. In one aspect, polymers such as polyethylene glycol (PEG) or methoxypolyethylene glycol (mPEG) can increase the in vivo half-life of proteins to which they are conjugated. Methods of PEGylation of polypeptide agents are well known to those skilled in the art, as are considerations of, for example, how large a PEG polymer to use. In another aspect, biodegradable or absorbable polymers can provide extended, often localized, release of polypeptide agents. Such synthetic bioabsorbable, biocompatible polymers, which may release proteins over several weeks or months can include, for example, poly-α-hydroxy acids (e.g. polylactides, polyglycolides and their copolymers), polyanhydrides, polyorthoesters, segmented block copolymers of polyethylene glycol and polybutylene terephtalate (POLYACTIVE™), tyrosine derivative polymers or poly(ester-amides). Suitable bioabsorbable polymers to be used in manufacturing of drug delivery materials and implants are discussed e.g. in U.S. Pat. Nos. 4,968,317; 5,618,563, among others, and in "Biomedical Polymers" edited by S. W. Shalaby, Carl Hanser Verlag, Munich, Vienna, New York, 1994 and in many references cited in the above publications. The particular bioabsorbable polymer that should be selected will depend upon the particular subject that is being treated.

In one embodiment, the sCD23 peptide/polypeptide is modified to include salts and/or chemical derivatives. As used herein, the term "chemical derivative" refers to a sCD23 peptide or polypeptide having one or more residues chemically derivatized by reaction of a functional side group. Such derivatized molecules can include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. Also included as chemical derivatives are sCD23 peptides or polypeptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

In another embodiment, the sCD23 peptide or polypeptide is modified to increase the stability in solution and, therefore, serve to prolong the half-life of the peptide/polypeptide inhibitor in solutions, particularly biological fluids, such as blood, plasma or serum, by blocking proteolytic activity in the blood. A sCD23 peptide/polypeptide can have a stabilizing group at one or both termini including, for example, amido, acetyl, benzyl, phenyl, tosyl, alkoxycarbonyl, alkyl carbonyl, benzyloxycarbonyl and the like end group modifications. Additional modifications include using a "L" amino acid in place of a "D" amino acid at the termini, cyclization of the peptide inhibitor, and amide rather than amino or carboxy termini to inhibit exopeptidase activity.

A sCD23 peptide/polypeptide as used herein may or may not be glycosylated. sCD23 peptides/polypeptides are not glycosylated, for example, when produced directly by synthesis techniques or are produced in a prokaryotic cell transformed with a recombinant polynucleotide. Peptide or polypeptide molecules produced in eukaryotic expression systems (such as, for example, *Saccharomyces cerevisiae*-based expression systems, baculovirus-based expression systems utilizing for example, Sf9 insect cells, and mammalian expression systems) are typically glycosylated.

In one embodiment, the sCD23 peptide/polypeptide is maintained in a constrained secondary conformation. The terms "constrained secondary structure," "stabilized" and "conformationally stabilized" indicate that the bonds comprising the peptide or polypeptide are not able to rotate freely but instead are maintained in a relatively fixed structure. A method for constraining the secondary structure of a newly synthesized linear peptide is to cyclize the peptide using any of various methods well known in the art. For example, a cyclized sCD23 peptide can be prepared by forming a peptide bond between non-adjacent amino acid residues as described, for example, by Schiller et al (1985). Peptides can be synthesized on the Merrifield resin by assembling the linear peptide chain using Nα-Fmoc-amino acids and Boc and tertiary-butyl proteins. Following the release of the peptide from the resin, a peptide bond can be formed between the amino and carboxy termini.

A newly synthesized linear peptide or polypeptide can also be cyclized by the formation of a bond between reactive amino acid side chains. For example, a peptide containing a cysteine-pair can be synthesized, with a disulfide bridge, can be formed by oxidizing a dilute aqueous solution of the peptide with $K_3Fe(CN)_6$. Alternatively, a lactam such as an ε-(γ-glutamyl)-lysine bond can be formed between lysine and glutamic acid residues, a lysinonorleucine bond can be formed between lysine and leucine residues or a dityrosine bond can be formed between two tyrosine residues. Cyclic peptides can be constructed to contain, for example, four lysine residues, which can form the heterocyclic structure of desmosine (see, for example, Devlin, 1997). Methods for forming these and other bonds are well known in the art and are based on well-known rules of chemical reactivity (Morrison et al, 1992).

In one embodiment, the sCD23 peptide or polypeptide (e.g., isolated, synthetic, or recombinant peptide) is attached to, or enclosed or enveloped by, a macromolecular complex. The macromolecular complex can be, without limitation, a virus, a bacteriophage, a bacterium, a liposome, a microparticle, a targeting sequence, a nanoparticle (e.g., a gold nanoparticle), a magnetic bead, a yeast cell, a mammalian cell, a cell or a microdevice. These are representative examples only and macromolecular complexes within the scope of the methods and compositions described herein can include virtually any complex that can attach or enclose a peptide/polypeptide and be administered to a subject.

If desired, the isolated sCD23 peptide/polypeptide can be attached to a solid support, such as, for example, magnetic beads, Sepharose beads, agarose beads, a nitrocellulose membrane, a nylon membrane, a column chromatography matrix, a high performance liquid chromatography (HPLC) matrix or a fast performance liquid chromatography (FPLC) matrix for purification. In one embodiment, the isolated sCD23 peptide/polypeptide can be attached to a scaffold or other device for local and/or sustained delivery of the sCD23 peptide to a site of allergic response.

In one embodiment, the sCD23 peptide/polypeptide comprises a fusion protein. These molecules generally have all or a substantial portion of the sCD23 peptide, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as, for example, active sites from enzymes, glycosylation domains, cellular targeting signals or transmembrane regions.

The fusion proteins described herein can comprise a sCD23 peptide or polypeptide linked to a second therapeutic protein or peptide. Examples of proteins or peptides that may be incorporated into a fusion protein include, but are not limited to, cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated herein that virtually any protein or peptide known to one of skill in the art could be incorporated into a fusion protein comprising a targeting peptide. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

Protein PEGylation

Polyethylene glycol (PEG) can be conjugated to the peptide or polypeptide compounds as described herein. PEGylation can be achieved by incubation of a reactive derivative of PEG with the target macromolecule. The conjugation to PEG can be performed either enzymatically or chemically, the methods of which are well established in the art (Chapman, 2002; Veronese and Pasut, 2005). With PEGylation the total size of a peptide can be increased, which reduces the chance of renal filtration and can increase the circulating half-life of the peptide. PEGylation further protects peptides from proteolytic degradation and slows the clearance from the blood. In addition, PEGylation reduces immunogenicity and increases solubility of macromolecules (e.g., peptides). The improved pharmacokinetics by the addition of PEG is due to several different mechanisms: increase in size of the molecule, protection from proteolysis, reduced antigenicity, and the masking of specific sequences from cellular receptors. For example, in the case of antibody fragments (Fab), a 20-fold increase in plasma half-life has been achieved by PEGylation (Chapman, 2002).

PEG moieties useful with the compositions and methods described herein include PEG polymers, derivatives and PEG lipids. PEG polymers can be e.g., linear, branched or multi-armed, among others. The PEG conjugate according to the present invention may be of any molecular weight, for example, the molecular weight may be between 500 and 100,000 Da, between 500 and 60,000 Da, between 1000 and 40,000 Da, or between 5000 and 40,000 Da. PEGs having molecular weights of 10000 Da, 20000 Da, 30000 Da or 40000 Da may be used with the peptides or polypeptides described herein.

In addition, other polymers are also contemplated for use with the methods and compositions described herein and include, but are not limited to, poly(alkylene glycols) such as poly(propylene glycol) ("PPG"), copolymers of ethylene glycol and propylene glycol and the like, poly(oxyethylated polyol), poly(olefinic alcohol), poly(vinylpyrrolidone), poly (hydroxyalkylmethacrylamide), poly(hydroxyalkylmethacrylate), poly(saccharides), poly(.alpha.-hydroxy acid), poly(vinyl alcohol), polyphosphazene, polyoxazoline, poly (N-acryloylmorpholine), and combinations of any of the foregoing. Representative polymeric reagents and methods for conjugating these polymers to an active moiety are known in the art and further described in Zalipsky, S., et al., "Use of Functionalized Poly(Ethylene Glycols) for Modification of Polypeptides" in Polyethylene Glycol Chemistry: Biotechnical and Biomedical Applications, J. M. Harris, Plenus Press, New York (1992), and in Zalipsky (1995) Advanced Drug Reviews 6:157-182.

Dosage and Administration

In one aspect, the methods described herein provide a method for treating an IgE mediated disease in a subject. In one embodiment, the subject can be a mammal. In another embodiment, the mammal can be a human, although the approach is effective with respect to all mammals. The method comprises administering to the subject an effective amount of a pharmaceutical composition comprising a sCD23 peptide/polypeptide, in a pharmaceutically acceptable carrier.

The dosage range for the sCD23 compound depends upon the potency and route of administration, and include amounts large enough to produce the desired effect, e.g., a measurable decrease in at least one symptom of an IgE mediated disease such as e.g., an allergic response. The dosage should not be so large as to cause unacceptable adverse side effects. Generally, the dosage will vary with the particular compound used and with the age, condition, and sex of the patient. The dosage can be determined by one of skill in the art and can also be adjusted by the individual physician in the event of any complication. Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 m/kg body weight to 30 m/kg body weight. Alternatively, the dose range will be titrated to maintain serum levels between 5 µg/mL and 30 m/mL.

In one embodiment, a sCD23 peptide/polypeptide as described herein is administered directly to a site of an allergic response by e.g., injection, inhalation, polymer or scaffold-mediated delivery etc.

Administration of the doses recited above can be repeated, if necessary, for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

A therapeutically effective amount is an amount of an agent that is sufficient to produce a statistically significant, measurable change in at least one symptom of an inflammatory disease etc. (see "Efficacy Measurement" below). Such effective amounts can be gauged in clinical trials as well as animal studies for a given sCD23 peptide or polypeptide.

Agents useful in the methods and compositions described herein can be administered by e.g., inhalation, topically, direct injection, intravenously (by bolus or continuous infusion), orally, intraperitoneally, intracavity, and can be delivered by peristaltic means, if desired, or by other means known by those skilled in the art. In one embodiment, the compositions are delivered by means of a scaffold, polymer, gel etc. for local delivery of sCD23 peptide.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, a sCD23 peptide is targeted to a specific tissue by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to a sCD23 peptide or polypeptide permits the agent attached to accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

Pharmaceutical Compositions

The present invention involves therapeutic compositions useful for practicing the therapeutic methods described herein. Therapeutic compositions contain a physiologically tolerable carrier together with a sCD23 peptide or polypeptide as described herein, dissolved or dispersed therein as an active ingredient. In a preferred embodiment, the therapeutic composition is not immunogenic when administered to a mammal or human patient for therapeutic purposes, unless so desired. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein.

Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the invention that will be effective in the treatment of a particular disorder or condition will depend on the nature of the disorder or condition, and can be determined by standard clinical techniques.

Monitoring Efficacy of Treatment

The efficacy of a given treatment for an IgE mediated disease can be determined by the skilled clinician. However, a treatment is considered "effective treatment," as the term is used herein, if any one or more of the signs or symptoms of an IgE mediated disease, for example, allergic responses such as e.g., coughing, sneezing, mucus production, rhinitis, itchy eyes, anaphylactic response to allergen, skin irritation, redness, inflammation, breathing difficulties etc. are altered in a beneficial manner, other clinically accepted symptoms or markers of disease are improved, or ameliorated. In one embodiment, the improvement is seen as a need for fewer anti-allergy treatments (e.g., allergy shots, steroids, etc), fewer episodes of hospitalization, and/or longer intervals between hospitalizations, than the individual has experienced prior to treatment with the peptide/polypeptide. Efficacy can also be measured by a failure of an individual to worsen as assessed by hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progress of an IgE mediated disease or reaction; or (2) relieving the disease, e.g., causing regression of symptoms. The methods can also be used to prevent or reduce the likelihood of the development of a chronic condition (e.g., asthma, eczema) or complication relating to an IgE mediated disease.

An effective amount for the treatment of an IgE mediated disease means that amount which, when administered to a mammal in need thereof, is sufficient to result in effective treatment as that term is defined herein. Efficacy of a peptide/polypeptide compound can be determined by assessing physical indicators of an IgE mediated disease, for example, congestion, coughing, sneezing, redness, itchiness, anaphylaxis, wheezing, swelling, etc.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

The inventors have identified an important molecule present in worm infected-people that is involved in modulating the immune system in a manner that prevents allergic symptoms. These findings indicate that this molecule works by interfering with IgE, a component of the immune system that initiates most allergic reactions including sneezing, coughing, sinus congestion, mucus production in the sinuses (rhinitis) or lungs (asthma).

Example 1

Background

People Infected with Parasitic Worms Lack Bona Fide Allergic Responses

Parasitic worm infection is classically associated with high levels of circulating eosinophils, activated mast cells and IgE, the major components that mediate allergic responses. Paradoxically, people infected with parasitic worms, do not demonstrate clinical allergic symptoms. A portion of this has been attributed to the "hygiene hypothesis" that states a lack of exposure to parasites increases susceptibility to allergic and other chronic inflammatory diseases. Thus, the basis of the hypothesis stems from the idea that worms immuno-modulate the immune system in a manner that prevents exaggerated or inappropriate immune responses to innocuous antigens, such as pollen or nut proteins. For example, inflammatory bowel disease is believed to stem from an unregulated immune response to normally non-pathogenic commensal microbes in the gut. In fact, ulcerative colitis patients can be cured of their disease through the treatment of parasitic worms.

Inflammatory bowel disease and other diseases are thought to be mediated by the opposite arm of the immune system that causes allergy. However, allergy is mediated by the very same mediators that respond to worm infection Animal models have demonstrated that certain cytokines might be upregulated in response to certain worm antigens that might attenuate the allergic response or development of the response to innocuous antigens.

The methods and compositions described herein offer a compelling link between the prevention of allergic responses and worm infection. The preliminary data demonstrate that schistosomes, a parasitic flat worm that infects over 207 million people worldwide, modifies a host protein in a specific manner that leads to the prevention of classic allergic responses. Thus the data described herein indicate that schistosomes produce a protease that cleaves CD23, the low affinity IgE receptor, in a specific manner. The resulting cleaved soluble (sCD23) product is different than that naturally produced by the host and has not been previously described.

Human CD23 is a cell bound IgE receptor that can be differentially cleaved by host- and microbial-proteases. Cleaved proteins exist as active soluble receptors and their effect depends upon their size and self-conjugation forms. sCD23 has multiple ligands including IgE, CD21 and perhaps Mac-1. Thus the effect of the different sCD23 isoforms depends upon the cell for which it binds to as well (FIG. 1). The methods and compositions described herein are based, in part, on observations in clinical samples and experimental data demonstrating that a small ~15 kDa sCD23 protein that binds IgE (FIG. 2) but not CD21 reduces allergy and other IgE-mediated diseases.

The protein sequence of Modified sCD23 includes residues 156-292:

```
Modified sCD23 for the treatment of IgE-mediated
disease
                                        (SEQ ID NO: 1)
156 -SGFVC NTCPEKWINF QRKCYYFGKG TKQWVHARYA

CDDMEGQLVS IHSPEEQDFL TKHASHTGSW IGLRNLDLKG

EFIWVDGSHV DYSNWAPGEP TSRSQGEDCV MMRGSGRWND

AFCDRKLGAW VCDRLATCTP PA -192 C TERMINUS
```

Example 2

Increasing IgE Binding by Changing a Heptavalent Ca++ Chelation Site in CD23 to an Octavalent Chelation Site CD23 is a Calcium Binding Protein.

Calcium is important for the binding of CD23 to IgE and the mechanism of calcium binding has been described. CD23 bears significant sequence similarity to other calcium binding lectins such as the human asialoglycoprotein receptor, mannose-binding protein (MBP), and DC-SIGN. The best characterized of these proteins, MBP is know to chelate calcium using 8 atoms to form a square pyramidal chelation structure. In contrast, CD23 appears to bind calcium using only 7 atoms. Because regions associated with calcium chelation are also associated with IgE binding it is desirable for this region to be as stable as possible. To promote the stability of Ca++ binding, the CD23 fragment is mutated such that it carries an additional carboxyl group capable of donating electron density. Without wishing to be bound by theory, the hypothesis is that this will stabilize the L1 loop that is important for the binding of IgE, increasing its affinity for the ligand and decreasing any requirement for high calcium concentrations.

Residue 258 (an Aspartic Acid) is Mutated to a Glutamic Acid.

This mutation will lead to the formation of an octavalent chelation site that will stabilize calcium binding and increase IgE binding affinity.

Modified sCD23 with higher IgE binding capacity (High Affinity) (underlined: D258 to E)

```
                                                    SEQ ID NO: 2
SGFVC NTCPEKWINF QRKCYYFGKG TKQWVHARYA CDDMEGQLVS

IHSPEEQDFL TKHASHTGSW IGLRNLDLKG EFIWVDGSHV

DYSNWAPGEP TSRSQGEECV MMRGSGRWND AFCDRKLGAW

VCDRLATCTP PA
```

This ~15 kD protein is an advantageous treatment for allergic diseases because it is found naturally in human blood and causes few side effects. Furthermore, mice express a similar protein that lacks the CD21 binding site, which has been shown to negatively regulate IgE production.

Example 3

Polypeptide Variations

Modified sCD23 contains the lectin head which binds IgE but lacks the CD21 tail. The CD21-binding tail encompasses amino acids 290 to 321. Sm-sCD23 is a non-CD21 binding protein that lacks amino acids 293-321. CD21 complement binding requires at least amino acids 290-298. Variations of this protein include producing sCD23 lacking any amino acids from 290 to 321.

```
                                                      SEQ ID No: 3
MEEGQYSEIE ELPRRRCCRR GTQIVLLGLV TAALWAGLLT LLLLWHWDTT

QSLKQLEERA ARNVSQVSKN LESHHGDQMA QKSQSTQISQ ELEELRAEQQ

RLKSQDLELS WNLNGLQADL SSFKSQELNE RNEASDLLER LREEVTKLRM

ELQVSSGFVC NTCPEKWINF QRKCYYFGKG TKQWVHARYA CDDMEGQLVS

IHSPEEQDFL TKHASHTGSW IGLRNLDLKG EFIWVDGSHV DYSNWAPGEP

TSRSQGEDCV MMRGSGRWND AFCDRKLGAW VCDRLATCTP PASEGSAESM

GPDSRPDPDG RLPTPSAPLH S
``` underlined text = lectin IgE binding domain
italicized text = C-tail CD21 binding domain
bold text = start of common sCD23 polypeptide (172 aa)

```
        Sequence of Modified sCD23
                                       (SEQ ID No: 4)
SGFVC NTCPEKWINF QRKCYYFGKG TKQWVHARYA

CDDMEGQLVS IHSPEEQDFL TKHASHTGSW IGLRNLDLKG

EFIWVDGSHV DYSNWAPGEP TSRSQGEDCV MMRGSGRWND

AFCDRKLGAW VCDRLATCTP PA

Polypeptide Variation A
                                       (SEQ ID NO: 5)
A monomeric protein that retains IgE-binding
properties but not CD21-binding ability
TT QSLKQLEERA ARNVSQVSKN LESHHGDQMA QKSQSTQISQ

ELEELRAEQQ RLKSQDLELS WNLNGLQADL SSFKSQELNE

RNEASDLLER LREEVTKLRM ELQVS SGFVC NTCPEKWINF

QRKCYYFGKG TKQWVHARYA CDDMEGQLVS IHSPEEQDFL

TKHASHTGSW IGLRNLDLKG EFIWVDGSHV DYSNWAPGEP

TSRSQGEDCV MMRGSGRWND AFCDRKLGAW VCDRLATCTP PA

SEGSAE

Polypeptide Variation B High Affinity Modified
sCD23
                                       (SEQ ID NO: 6)
TT QSLKQLEERA ARNVSQVSKN LESHHGDQMA QKSQSTQISQ

ELEELRAEQQ RLKSQDLELS WNLNGLQADL SSFKSQELNE

RNEASDLLER LREEVTKLRM ELQVS SGFVC NTCPEKWINF

QRKCYYFGKG TKQWVHARYA CDDMEGQLVS IHSPEEQDFL

TKHASHTGSW IGLRNLDLKG EFIWVDGSHV DYSNWAPGEP

TSRSQGEECV MMRGSGRWND AFCDRKLGAW VCDRLATCTP PA

SEGSAE
```

Example 4

Advantages Over Current Treatments

Avoid Anaphylactic Shock and Other Severe Side Effects

Figure 5A:
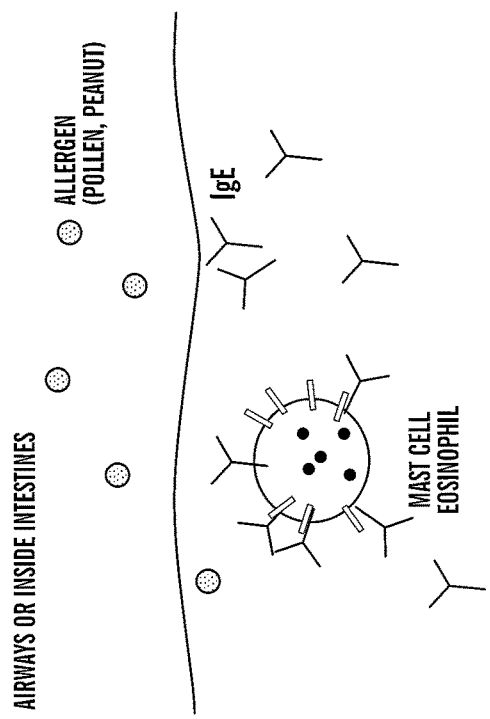
Figure 5D:
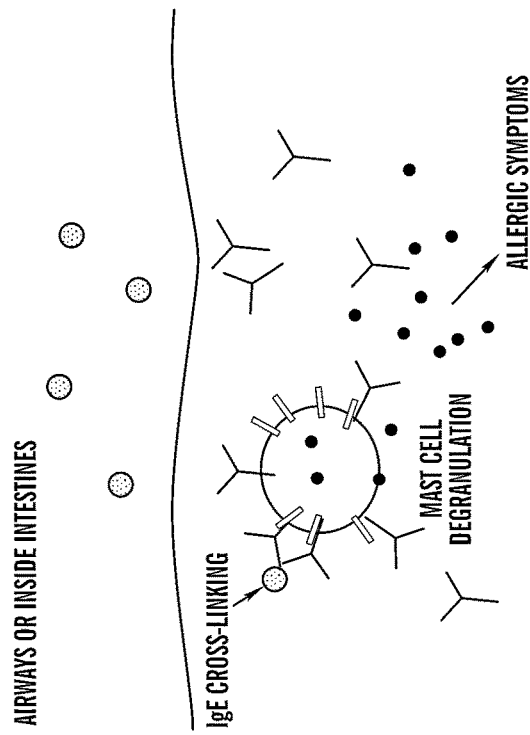
Figure 5C:
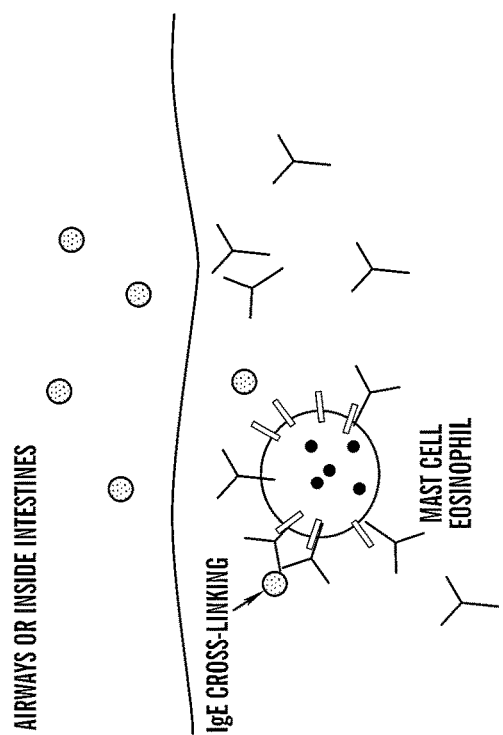
Figure 5H:
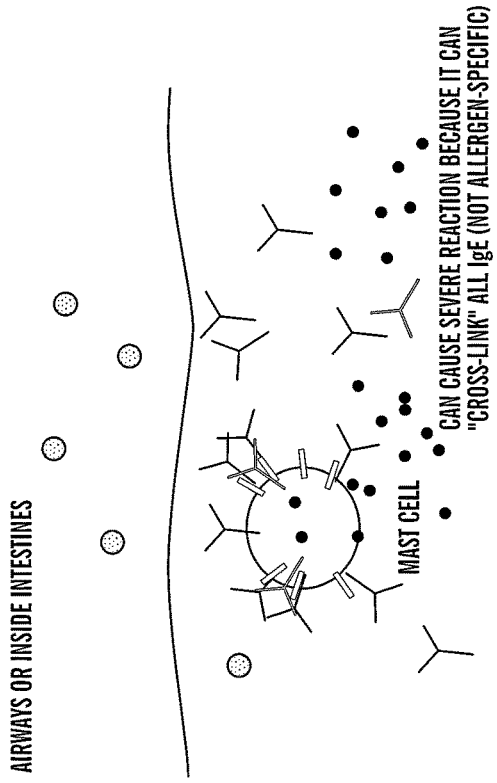
Figure 5G:
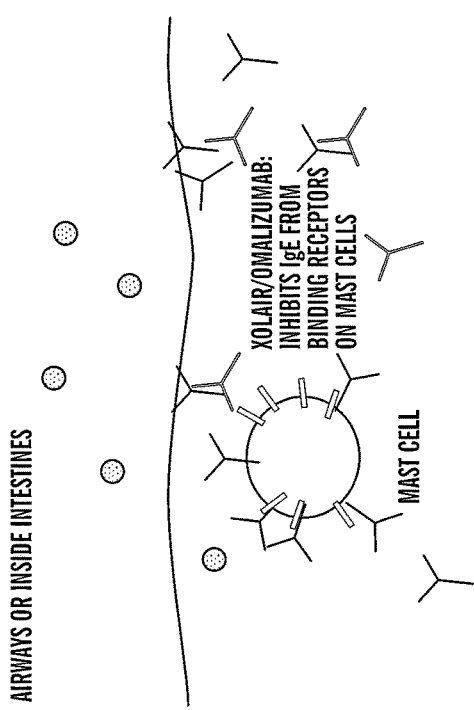
Figure 5I:
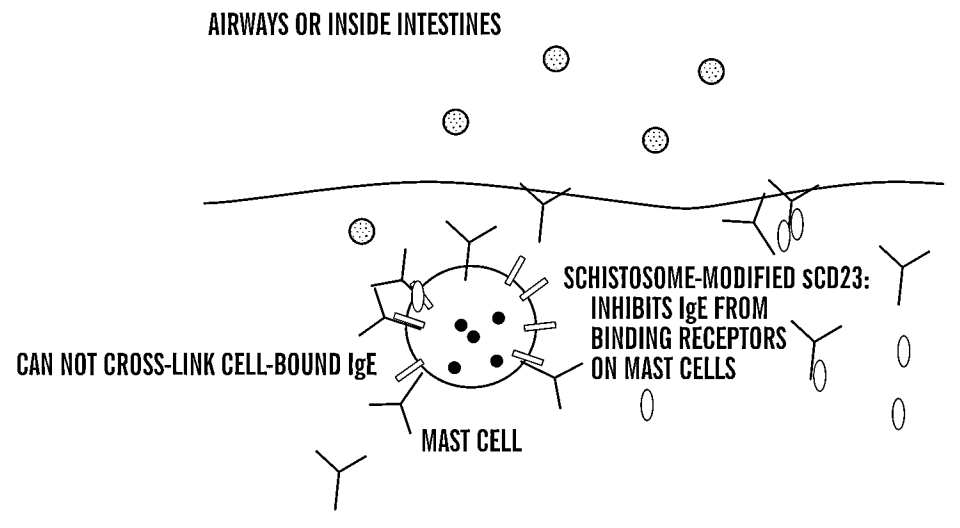
Figure 7A:
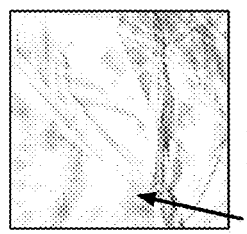
FIGS. 7A and 7B show data indicating that the expressed protein is at the correct predicted molecular weight.
Figure 7B:
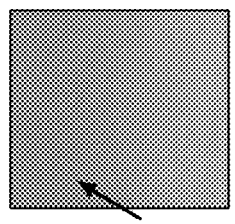
Figure 9:
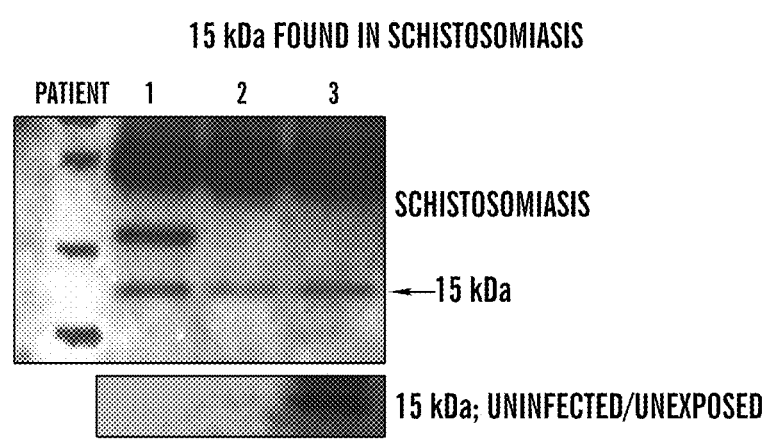
FIG. 9 is a micrograph indicating that modified sCD23 is found in serum of patients with schistosomiasis. The 15 kDa sCD23 fragment is apparent in patients hyper-exposed to infectious schistosomes in Western Kenya (top panel). In contrast, subjects unexposed/uninfected rarely demonstrate the fragment (lower panel).
Figures 10A, 10B:
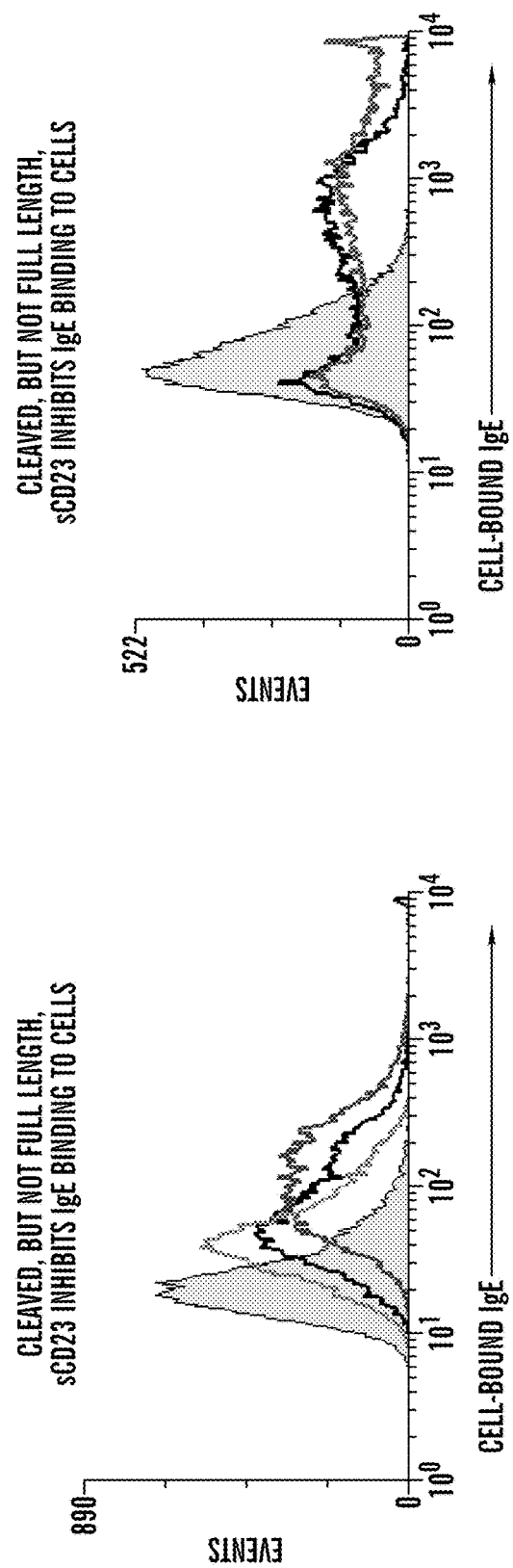
FIGS. 10A and 10B are graphs showing in vitro data demonstrating mechanistically that schistosome modified sCD23 acts as a decoy receptor for IgE and prevents IgE from binding to its cell surface receptor FcεRIα.

Modified sCD23 is a low-affinity IgE receptor and can only bind one IgE Fc molecule. In contrast, Xolair is a monoclonal antibody which has 2 binding sites and has the potential to cross-link IgE on the cell surface (FIG. 5; ~2% reported incidence). Therefore, it is unlikely that modified sCD23 will have the ability to induce anaphylactic shock that is seen with the use of Xolair. Further, due to its potency, Xolair has also been associated with malignancy and Churg-Strauss syndrome, which is an autoimmune vasculitis, as well.

Xolair® has already been shown to be effective in reducing allergic disease, but is prohibitively expensive and potentially dangerous. However, modified sCD23, which has a similar mechanism of action as Xolair, represents an ideal, low cost allergic treatment. In addition, anti-IgE mediated therapy has proven effective in other diseases such as corticosteroid induced diabetes in bronchopulmonary aspergillosis and cystic fibrosis highlighting other potential uses for modified sCD23.

Reduce Health Care Costs Associated with Allergy

Modified sCD23 has a similar mechanism of action as Xolair (except for the ability to induce anaphylaxis.) Xolair is prohibitively costly due to its mechanism of action and may cause anaphylactic shock. Therefore this treatment must be administered in a physician's office. It is unlikely that modified sCD23 will induce anaphylactic shock and thus the requirement for administration in a physician's office will be removed. Removal of this requirement opens the large market of the complex array of allergic treatments for a broad patient base. In general, patients report low satisfaction with allergy treatments. Intranasal corticoid steroids (INCS) are considered the gold-standard for AR but this treatment is associated with bone mineral lost, growth retardation, and adrenal suppression which is troublesome for children. Modified sCD23 will not produce these side effects thereby reducing the cost of care for patients with INCS-induced adverse effects.

Over the counter (OTC) anti-histamine/decongestants also have adverse effects, such as drowsiness, epistaxis, and burning and have the tendency to stop working. In contrast, modified sCD23 is not likely to induce these side-effects either. sCD23 is an effective treatment and patients will reduce their cost of attempting to provide relief with multiple over the counter drugs.

Treatment to a Broad Allergic Population

Currently, Xolair is only cost-effective for a small population of asthmatic patients. Because of the predicted low production costs and increased safety, modified sCD23 is an effective treatment for a broad range of IgE-mediated diseases, including allergy. Further, due to its natural chemical nature, modified sCD23 can be used in children and pregnancy.

Market the Product as Safe and Effective

Modified sCD23 appears to be found in human sera at low concentrations in people who are not infected with schistosomes. In contrast, modified sCD23 appears to be found in high concentrations in people who are infected with schistosomes, highlighting the potential safety of the treatment.

Example 5

Methods for Testing Binding Properties of a sCD23 Peptide or Polypeptide

The data provided herein indicate that incubation of CD23+ cells with schistosome antigens reduces surface CD23 levels. It has been shown that multiple host and microbe-derived proteases may differentially cleave CD23, therefore the cell supernatants of B cells treated with schistosome antigens were evaluated to determine the characteristics of the cleaved products by western blot. Supernatants from B cells treated with schistosome antigens were enriched with a 15 kDa product (FIG. 2). As certain cleaved sCD23 peptides can bind both IgE and CD21, the binding properties of the 15 kDa protein were tested. CD23 is known to interact with CD21 on two sites of CD21. The reagent used in this assay was rhuCD21 from XpressBio which is a 43 kDa protein aa: 130-280 (out of 1092) and spans 1-2 of the short consensus repeats (SCR). This region contains the necessary binding for CD23 but it is not known how this might affect the ability of CD23 to bind IgE. The intensity of the 15 kDa band was decreased in the presence of sCD21 indicating that sCD21 blocks cleavage of CD23 by schistosomes (FIG. 2B). Further, CD21 did not appear to co-precipitate with the 15 kDa sCD23. In contrast, FIG. 2 demonstrates that IgE can be immuno-precipitated with sCD23 indicating that schistosome-generated sCD23 binds IgE. Thus, the CD21 binding site on the tail is likely eliminated.

Without wishing to be bound by theory, sequestration of IgE by schistosome modified sCD23 may be an immuno-evasion tactic to promote parasitism. It is hypothesized that promotion of parasitism may also benefit the host by preventing anaphylaxis and other severe allergic reactions in the presence of copious IgE and eosinophils.

Human soluble CD23 is modified by schistosomes (a protease cleavage event), which produces a CD23 fragment that binds IgE, but not CD21. This novel CD23 fragment likely plays an important role in controlling inappropriate IgE mediated immunity in schistosomiasis and that it is the IgE-only binding characteristic of this fragment that is important. A recombinant form of the schistosome-cleaved CD23 fragment is provided herein and can be epitope tagged to facilitate analysis.

His6 (SEQ ID NO: 12) and Myc epitope-tagged fragments of CD23 that contain amino acids 156-292 were chosen since existing data indicates that this fragment will fold properly and will contain the IgE binding domain but will lack the CD21 binding domain. The NMR structure of a soluble CD23 protein that binds both IgE and CD21 shows that each of these molecules binds at a structurally distinct place on the CD23 molecule. IgE binds to the lectin-head region (including residues from (aa187 to 279), while CD21 appears to involve residues that are separated in both primary structure and tertiary structure (residues 294 and above). Thus, a fragment from 156-292 includes the lectin binding region that is important for binding to IgE but is devoid of the residues required for CD21 interaction.

In designing the recombinant fragment it was elected to add two separate types of affinity tags. The His6 (SEQ ID NO: 12) sequence serves as an affinity-tag for purification. The His-tag was chosen over other well established protein-fusion strategies (i.e. schistosome GST, Maltose Binding protein) because the His-tag adds minimally to the overall molecular weight and structure of the protein fragment. The second affinity tag, the Myc epitope serves to provide a high-affinity antibody binding region to allow biochemical (immuno-precipitation) and immunological (FACS) manipulation and identification of the fusion protein.

To achieve this, a small portion of CD23 is subcloned into the bacterial expression vector pET 28a. This vector has the advantage of having a His6 tag (SEQ ID NO: 12) designed into the start of the translated protein sequence. The CD23 156-292 fragment is placed into this vector by using two primers. The first contains a NheI cleavage site and adds the c-Myc epitope sequence EQKLISEEDL (SEQ ID NO: 212) 5' to the CD23 sequence. The second contains a stop codon and a HindIII site that are arranged so that they are 3' to the codon for amino acid 292 of CD23. The codon bias for the c-Myc sequence is altered to optimize expression in $E.\ coli$ (for example, the sequence can be: GAA CAG AAA CTG ATC TCT GAA GAA GAC CTG (SEQ ID NO: 213)). CD23 is PCR amplified from total RNA from tonsil B cells using these primers and then the cDNA fragment is ligated into pET28a (the CD23 fragment does not itself contain either an NheI or HindIII cleavage site so these will be unique to the primers). The resulting plasmid is sequenced to verify proper cloning, and the plasmid is then transformed into a protein expressing strain of $E.\ coli$ (e.g. BLR pLysS or comparable DE3+ strain). Expression of the CD23 fragment is optimized using standard procedures. The fragment can be purified on Ni-NTA agarose and is removed from the agarose column either by imidazole washes or by cleavage of the His tag from the peptide using the thrombin protease.

Example 6

Methods for Testing Efficacy of Modified sCD23 to Prevent Allergic Symptoms in Vivo B6.Cg-Fcer1a$^{tm1Knt}$ Tg(FCER1A)1Bhk/J which express the Fc portion of human IgE and the human FcεRI α-chain, which binds IgE. These mice have been shown to respond to experimental induction of anaphylaxis and are an ideal model to test the efficacy of Modified sCD23 in preventing allergic reactions.

Mice are injected intravenously with 20 μg of human IgE specific for NP (Serotec). 24 hours later, mice are injected with NP-BSA to induce cross-linking of cell bound IgE and anaphylaxis-like disease. Evans blue dye is co-injected with NP-BSA to track vessel leakage into the tissues.

Mice can be pre-treated with 1, 10, 50, 100, or 200 μg of Modified sCD23 two hours prior to the injection of IgE. 24 hours later, peripheral blood and tissue FcεR1+ cells are measured for the level of cell-bound IgE.

Once an appropriate dose of a particular peptide or polypeptide is chosen, mice are pre-treated with that concentration of Modified sCD23 two hours prior to the injection of IgE. 24 hours later, NP-BSA is injected into mice and symptoms of allergy are measured as below compared to mice that have received no IgE or no Modified sCD23.

Measurement of Allergy in Mice

Symptoms of systemic anaphylaxis appear within 15 to 30 minutes and reach a peak at 40 to 50 minutes after the first symptoms appear. A symptom scoring system is used according to previously described parameters of symptoms for determining IgE-mediated responses in mice. Briefly, 0 is assigned if no symptoms are evident, and 1 through 5 are assigned if symptoms are observed, where 1 represents mild scratching, rubbing, or both of the nose, head, or feet; 2 and 3 represent intermediate symptoms (e.g., edema around the eyes or mouth, pilar erection, and/or labored breathing); 4 represents significantly reduced motility, tremors, and/or significant respiratory distress; and 5 represents death. One hour after challenge, mice are bled for plasma histamine levels. Twenty-four hours later, mice are euthanized, and tissues collected for analysis.

Plasma histamine levels are determined by using an EIA kit from Becton Dickenson (Franklin Lakes, N.J.), as per the manufacturer's instructions.

To detect vascular leakage footpads and ears of mice are examined for signs of vascular leakage (visible blue color) 30 to 40 minutes after dye/antigen administration.

The invention claimed is:

1. A compound of the formula $X_1$—$R_0$ (SEQ ID NO: 214), wherein $R_0$ comprises SEQ ID NO: 4 and $X_1$ comprises
TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 7), or a contiguous fragment of at least 15 amino acids of SEQ ID NO: 7, and wherein the compound comprises an amino acid substitution D107E of SEQ ID NO: 4, or wherein the compound does not comprise amino acids 290-298 of SEQ ID NO: 3; or wherein the compound does not comprise amino acids 290-321 of SEQ ID NO: 3.

2. The compound of claim 1, wherein the compound is PEGylated.

3. The compound of claim 1, further comprising a pharmaceutically acceptable carrier.

4. A method for reducing a subject's immune response to an allergen, the method comprising: administering to a subject a pharmaceutical composition containing an effective amount of a compound selected from:
a compound of formula $X_1$—$R_0$ (SEQ ID NO: 214), wherein $R_0$ comprises SEQ ID NO: 4 and $X_1$ comprises
TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 7), or a contiguous fragment of at least 15 amino acids of SEQ ID NO: 7, and wherein the compound comprises an amino acid substitution D107E of SEQ ID NO: 4, or wherein the compound does not comprise amino acids 290-298 of SEQ ID NO: 3; or wherein the compound does not comprise amino acids 290-321 of SEQ ID NO: 3,
a compound of formula $R_0$—$X_2$ (SEQ ID NO: 215), wherein $R_0$ comprises SEQ ID NO: 4, and wherein the compound comprises an amino acid substitution D107E of SEQ ID NO: 4, and $X_2$ comprises SEGSAE (SEQ ID NO: 9), SEGSA (SEQ ID NO: 10), SEGS (SEQ ID NO: 11), SEG, SE, S, L, or —COOH, and
a compound of formula $X_1$—$R_0$—$X_2$ (SEQ ID NO: 216), wherein $R_0$ comprises SEQ ID NO: 4, $X_1$ comprises at least 15 contiguous amino acids of TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 7), and wherein the compound comprises an amino acid substitution D107E of SEQ ID NO: 4, or wherein the compound does not comprise amino acids 290-298 of SEQ ID NO: 3; or wherein the compound does not comprise amino acids 290-321 of SEQ ID NO: 3, and $X_2$ comprises SEGSAE (SEQ ID NO: 9), SEGSA (SEQ ID NO: 10), SEGS (SEQ ID NO: 11), SEG, SE, S, L, or —COOH; and a pharmaceutically acceptable carrier.

5. The method of claim 4, wherein the pharmaceutical composition is administered prophylactically to a subject at risk of having an immune response to an allergen.

6. The method of claim 4, wherein the pharmaceutical composition is administered to a subject following exposure to the allergen.

7. The method of claim 4, further comprising administering steroid therapy.

8. The method of claim 4, further comprising administering allergy shots to said subject.

9. The method of claim 4, wherein the allergen is a food allergen, a pollen, a plant allergen, a dust mite, animal dander, insect stings, a fungus, a spore, a mold, latex, or a drug.

10. The method of claim 4, further comprising a step of selecting a subject having an immune response to an allergen.

11. The method of claim 4, wherein the subject's immune response to an allergen is a chronic immune response to an allergen.

12. The method of claim 4, wherein the subject is being treated with an allergy or anaphylaxis treatment.

13. A method for treating an IgE-mediated disease in a subject, the method comprising administering to a subject a pharmaceutical composition containing an effective amount of a compound selected from:
a compound of formula $X_1$—$R_0$ (SEQ ID NO: 214), wherein $R_0$ comprises SEQ ID NO: 4 and $X_1$ comprises
TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 7), or a contiguous fragment of at least 15 amino acids of SEQ ID NO: 7, and wherein the compound comprises an amino acid substitution D107E of SEQ ID NO: 4, or wherein the compound does not comprise amino acids 290-298 of SEQ ID NO: 3; or wherein the compound does not comprise amino acids 290-321 of SEQ ID NO: 3 a compound of formula $R_0$—$X_2$ (SEQ ID NO: 215), wherein $R_0$ comprises SEQ ID NO: 4, and wherein the compound comprises an amino acid substitution D107E of SEQ ID NO: 4, and $X_2$ comprises SEGSAE (SEQ ID NO: 9), SEGSA (SEQ ID NO: 10), SEGS (SEQ ID NO: 11), SEG, SE, S, L, or —COOH, and a compound of the formula $X_1$—$R_0$—$X_2$ (SEQ ID NO: 216), wherein $R_0$ comprises SEQ ID NO: 4, and wherein the compound comprises an amino acid substitution D107E of SEQ ID NO: 4, $X_1$ comprises at least 15 contiguous amino acids of TT QSLKQLEERA ARNVSQVSKN LESHHGDQMA QKSQSTQISQ ELEELRAEQQ RLKSQDLELS WNLNGLQADL SSFKSQELNE RNEASDLLER LREEVTKLRM ELQVS (SEQ ID NO: 7), and $X_2$ comprises SEGSAE (SEQ ID NO: 9), SEGSA (SEQ ID NO: 10), SEGS (SEQ ID NO: 11), SEG, SE, S, L, or —COOH; and a pharmaceutically acceptable carrier.

14. The method of claim 13, wherein the IgE mediated disease is selected from the group consisting of: allergy, anaphylaxis, asthma, eczema, and rhinitis.

* * * * *

SEQUENCE LISTING

```
<160> NUMBER OF SEQ ID NOS: 216

<210> SEQ ID NO 1
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Gly Phe Val Cys Asn Thr Cys Pro Glu Lys Trp Ile Asn Phe Gln
1               5                   10                  15

Arg Lys Cys Tyr Tyr Phe Gly Lys Gly Thr Lys Gln Trp Val His Ala
            20                  25                  30

Arg Tyr Ala Cys Asp Asp Met Glu Gly Gln Leu Val Ser Ile His Ser
        35                  40                  45

Pro Glu Glu Gln Asp Phe Leu Thr Lys His Ala Ser His Thr Gly Ser
    50                  55                  60

Trp Ile Gly Leu Arg Asn Leu Asp Leu Lys Gly Glu Phe Ile Trp Val
65                  70                  75                  80

Asp Gly Ser His Val Asp Tyr Ser Asn Trp Ala Pro Gly Glu Pro Thr
                85                  90                  95

Ser Arg Ser Gln Gly Glu Asp Cys Val Met Met Arg Gly Ser Gly Arg
            100                 105                 110

Trp Asn Asp Ala Phe Cys Asp Arg Lys Leu Gly Ala Trp Val Cys Asp
        115                 120                 125

Arg Leu Ala Thr Cys Thr Pro Pro Ala
    130                 135

<210> SEQ ID NO 2
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Gly Phe Val Cys Asn Thr Cys Pro Glu Lys Trp Ile Asn Phe Gln
```

```
1               5                   10                  15
Arg Lys Cys Tyr Tyr Phe Gly Lys Gly Thr Lys Gln Trp Val His Ala
                20                  25                  30
Arg Tyr Ala Cys Asp Asp Met Glu Gly Gln Leu Val Ser Ile His Ser
                35                  40                  45
Pro Glu Glu Gln Asp Phe Leu Thr Lys His Ala Ser His Thr Gly Ser
            50                  55                  60
Trp Ile Gly Leu Arg Asn Leu Asp Leu Lys Gly Glu Phe Ile Trp Val
65                  70                  75                  80
Asp Gly Ser His Val Asp Tyr Ser Asn Trp Ala Pro Gly Glu Pro Thr
                85                  90                  95
Ser Arg Ser Gln Gly Glu Glu Cys Val Met Met Arg Gly Ser Gly Arg
                100                 105                 110
Trp Asn Asp Ala Phe Cys Asp Arg Lys Leu Gly Ala Trp Val Cys Asp
                115                 120                 125
Arg Leu Ala Thr Cys Thr Pro Pro Ala
                130                 135
```

<210> SEQ ID NO 3
<211> LENGTH: 321
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Glu Glu Gly Gln Tyr Ser Glu Ile Glu Leu Pro Arg Arg Arg
1               5                   10                  15
Cys Cys Arg Arg Gly Thr Gln Ile Val Leu Leu Gly Leu Val Thr Ala
                20                  25                  30
Ala Leu Trp Ala Gly Leu Leu Thr Leu Leu Leu Trp His Trp Asp
                35                  40                  45
Thr Thr Gln Ser Leu Lys Gln Leu Glu Glu Arg Ala Ala Arg Asn Val
    50                  55                  60
Ser Gln Val Ser Lys Asn Leu Glu Ser His His Gly Asp Gln Met Ala
65                  70                  75                  80
Gln Lys Ser Gln Ser Thr Gln Ile Ser Gln Glu Leu Glu Glu Leu Arg
                85                  90                  95
Ala Glu Gln Gln Arg Leu Lys Ser Gln Asp Leu Glu Leu Ser Trp Asn
                100                 105                 110
Leu Asn Gly Leu Gln Ala Asp Leu Ser Ser Phe Lys Ser Gln Glu Leu
            115                 120                 125
Asn Glu Arg Asn Glu Ala Ser Asp Leu Leu Glu Arg Leu Arg Glu Glu
        130                 135                 140
Val Thr Lys Leu Arg Met Glu Leu Gln Val Ser Ser Gly Phe Val Cys
145                 150                 155                 160
Asn Thr Cys Pro Glu Lys Trp Ile Asn Phe Gln Arg Lys Cys Tyr Tyr
                165                 170                 175
Phe Gly Lys Gly Thr Lys Gln Trp Val His Ala Arg Tyr Ala Cys Asp
                180                 185                 190
Asp Met Glu Gly Gln Leu Val Ser Ile His Ser Pro Glu Glu Gln Asp
        195                 200                 205
Phe Leu Thr Lys His Ala Ser His Thr Gly Ser Trp Ile Gly Leu Arg
    210                 215                 220
```

```
Asn Leu Asp Leu Lys Gly Glu Phe Ile Trp Val Asp Gly Ser His Val
225                 230                 235                 240

Asp Tyr Ser Asn Trp Ala Pro Gly Glu Pro Thr Ser Arg Ser Gln Gly
            245                 250                 255

Glu Asp Cys Val Met Met Arg Gly Ser Gly Arg Trp Asn Asp Ala Phe
        260                 265                 270

Cys Asp Arg Lys Leu Gly Ala Trp Val Cys Asp Arg Leu Ala Thr Cys
        275                 280                 285

Thr Pro Pro Ala Ser Glu Gly Ser Ala Glu Ser Met Gly Pro Asp Ser
        290                 295                 300

Arg Pro Asp Pro Asp Gly Arg Leu Pro Thr Pro Ser Ala Pro Leu His
305                 310                 315                 320

Ser

<210> SEQ ID NO 4
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ser Gly Phe Val Cys Asn Thr Cys Pro Glu Lys Trp Ile Asn Phe Gln
1               5                   10                  15

Arg Lys Cys Tyr Tyr Phe Gly Lys Gly Thr Lys Gln Trp Val His Ala
            20                  25                  30

Arg Tyr Ala Cys Asp Asp Met Glu Gly Gln Leu Val Ser Ile His Ser
        35                  40                  45

Pro Glu Glu Gln Asp Phe Leu Thr Lys His Ala Ser His Thr Gly Ser
    50                  55                  60

Trp Ile Gly Leu Arg Asn Leu Asp Leu Lys Gly Glu Phe Ile Trp Val
65                  70                  75                  80

Asp Gly Ser His Val Asp Tyr Ser Asn Trp Ala Pro Gly Glu Pro Thr
                85                  90                  95

Ser Arg Ser Gln Gly Glu Asp Cys Val Met Met Arg Gly Ser Gly Arg
            100                 105                 110

Trp Asn Asp Ala Phe Cys Asp Arg Lys Leu Gly Ala Trp Val Cys Asp
        115                 120                 125

Arg Leu Ala Thr Cys Thr Pro Pro Ala
    130                 135

<210> SEQ ID NO 5
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
```

```
            50                  55                  60
Leu Asn Gly Leu Gln Ala Asp Leu Ser Ser Phe Lys Ser Gln Glu Leu
 65                  70                  75                  80

Asn Glu Arg Asn Glu Ala Ser Asp Leu Leu Glu Arg Leu Arg Glu Glu
                 85                  90                  95

Val Thr Lys Leu Arg Met Glu Leu Gln Val Ser Ser Gly Phe Val Cys
                100                 105                 110

Asn Thr Cys Pro Glu Lys Trp Ile Asn Phe Gln Arg Lys Cys Tyr Tyr
                115                 120                 125

Phe Gly Lys Gly Thr Lys Gln Trp Val His Ala Arg Tyr Ala Cys Asp
            130                 135                 140

Asp Met Glu Gly Gln Leu Val Ser Ile His Ser Pro Glu Glu Gln Asp
145                 150                 155                 160

Phe Leu Thr Lys His Ala Ser His Thr Gly Ser Trp Ile Gly Leu Arg
                165                 170                 175

Asn Leu Asp Leu Lys Gly Glu Phe Ile Trp Val Asp Gly Ser His Val
                180                 185                 190

Asp Tyr Ser Asn Trp Ala Pro Gly Glu Pro Thr Ser Arg Ser Gln Gly
            195                 200                 205

Glu Asp Cys Val Met Met Arg Gly Ser Gly Arg Trp Asn Asp Ala Phe
210                 215                 220

Cys Asp Arg Lys Leu Gly Ala Trp Val Cys Asp Arg Leu Ala Thr Cys
225                 230                 235                 240

Thr Pro Pro Ala Ser Glu Gly Ser Ala Glu
                245                 250

<210> SEQ ID NO 6
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Thr Thr Gln Ser Leu Lys Gln Leu Glu Glu Arg Ala Ala Arg Asn Val
 1               5                  10                  15

Ser Gln Val Ser Lys Asn Leu Glu Ser His His Gly Asp Gln Met Ala
                20                  25                  30

Gln Lys Ser Gln Ser Thr Gln Ile Ser Gln Glu Leu Glu Glu Leu Arg
            35                  40                  45

Ala Glu Gln Gln Arg Leu Lys Ser Gln Asp Leu Glu Leu Ser Trp Asn
 50                  55                  60

Leu Asn Gly Leu Gln Ala Asp Leu Ser Ser Phe Lys Ser Gln Glu Leu
 65                  70                  75                  80

Asn Glu Arg Asn Glu Ala Ser Asp Leu Leu Glu Arg Leu Arg Glu Glu
                 85                  90                  95

Val Thr Lys Leu Arg Met Glu Leu Gln Val Ser Ser Gly Phe Val Cys
                100                 105                 110

Asn Thr Cys Pro Glu Lys Trp Ile Asn Phe Gln Arg Lys Cys Tyr Tyr
                115                 120                 125

Phe Gly Lys Gly Thr Lys Gln Trp Val His Ala Arg Tyr Ala Cys Asp
            130                 135                 140

Asp Met Glu Gly Gln Leu Val Ser Ile His Ser Pro Glu Glu Gln Asp
145                 150                 155                 160
```

```
Phe Leu Thr Lys His Ala Ser His Thr Gly Ser Trp Ile Gly Leu Arg
                165                 170                 175

Asn Leu Asp Leu Lys Gly Glu Phe Ile Trp Val Asp Gly Ser His Val
            180                 185                 190

Asp Tyr Ser Asn Trp Ala Pro Gly Glu Pro Thr Ser Arg Ser Gln Gly
        195                 200                 205

Glu Glu Cys Val Met Met Arg Gly Ser Gly Arg Trp Asn Asp Ala Phe
    210                 215                 220

Cys Asp Arg Lys Leu Gly Ala Trp Val Cys Asp Arg Leu Ala Thr Cys
225                 230                 235                 240

Thr Pro Pro Ala Ser Glu Gly Ser Ala Glu
                245                 250

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala Ser Asp Leu Leu Glu Arg Leu Arg Glu Glu
                85                  90                  95

Val Thr Lys Leu Arg Met Glu Leu Gln Val Ser
            100                 105

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Gln Val Ser
1

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Glu Gly Ser Ala Glu
1               5
```

```
<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Glu Gly Ser Ala
1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Glu Gly Ser
1

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6XHis tag

<400> SEQUENCE: 12

His His His His His His
1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Thr Lys Leu Arg Met Glu Leu Gln Val Ser
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Val Thr Lys Leu Arg Met Glu Leu Gln Val Ser
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

Glu Glu Val Thr Lys Leu Arg Met Glu Leu Gln Val Ser
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Glu Glu Val Thr Lys Leu Arg Met Glu Leu Gln Val Ser
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Arg Glu Glu Val Thr Lys Leu Arg Met Glu Leu Gln Val Ser
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Leu Arg Glu Glu Val Thr Lys Leu Arg Met Glu Leu Gln Val Ser
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Arg Leu Arg Glu Glu Val Thr Lys Leu Arg Met Glu Leu Gln Val
1               5                   10                  15

Ser

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Glu Arg Leu Arg Glu Glu Val Thr Lys Leu Arg Met Glu Leu Gln
1               5                   10                  15

Val Ser

```
<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Leu Glu Arg Leu Arg Glu Glu Val Thr Lys Leu Arg Met Glu Leu
1               5                   10                  15

Gln Val Ser

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Leu Leu Glu Arg Leu Arg Glu Glu Val Thr Lys Leu Arg Met Glu
1               5                   10                  15

Leu Gln Val Ser
            20

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Asp Leu Leu Glu Arg Leu Arg Glu Glu Val Thr Lys Leu Arg Met
1               5                   10                  15

Glu Leu Gln Val Ser
            20

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Ser Asp Leu Leu Glu Arg Leu Arg Glu Glu Val Thr Lys Leu Arg
1               5                   10                  15

Met Glu Leu Gln Val Ser
            20

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Ala Ser Asp Leu Leu Glu Arg Leu Arg Glu Glu Val Thr Lys Leu
1               5                   10                  15
```

```
Arg Met Glu Leu Gln Val Ser
            20

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Glu Ala Ser Asp Leu Leu Glu Arg Leu Arg Glu Glu Val Thr Lys
1               5                   10                  15

Leu Arg Met Glu Leu Gln Val Ser
            20

<210> SEQ ID NO 27
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Asn Glu Ala Ser Asp Leu Leu Glu Arg Leu Arg Glu Glu Val Thr
1               5                   10                  15

Lys Leu Arg Met Glu Leu Gln Val Ser
            20                  25

<210> SEQ ID NO 28
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Arg Asn Glu Ala Ser Asp Leu Leu Glu Arg Leu Arg Glu Glu Val
1               5                   10                  15

Thr Lys Leu Arg Met Glu Leu Gln Val Ser
            20                  25

<210> SEQ ID NO 29
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asn Glu Arg Asn Glu Ala Ser Asp Leu Leu Glu Arg Leu Arg Glu Glu
1               5                   10                  15

Val Thr Lys Leu Arg Met Glu Leu Gln Val Ser
            20                  25

<210> SEQ ID NO 30
<211> LENGTH: 28
<212> TYPE: PRT
<213> ORGANISM: Artificial Sequence
<220> FEATURE:
<223> OTHER INFORMATION: Description of Artificial Sequence: Synthetic
```

-continued

```
        peptide

<400> SEQUENCE: 30

Leu Asn Glu Arg Asn Glu Ala Ser Asp Leu Leu Glu Arg Leu Arg Glu
1               5                   10                  15

Glu Val Thr Lys Leu Arg Met Glu Leu Gln Val Ser
            20                  25

<210> SEQ ID NO 31
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Leu Asn Glu Arg Asn Glu Ala Ser Asp Leu Leu Glu Arg Leu Arg
1               5                   10                  15

Glu Glu Val Thr Lys Leu Arg Met Glu Leu Gln Val Ser
            20                  25

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Glu Leu Asn Glu Arg Asn Glu Ala Ser Asp Leu Leu Glu Arg Leu
1               5                   10                  15

Arg Glu Glu Val Thr Lys Leu Arg Met Glu Leu Gln Val Ser
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ser Gln Glu Leu Asn Glu Arg Asn Glu Ala Ser Asp Leu Leu Glu Arg
1               5                   10                  15

Leu Arg Glu Glu Val Thr Lys Leu Arg Met Glu Leu Gln Val Ser
            20                  25                  30

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Lys Ser Gln Glu Leu Asn Glu Arg Asn Glu Ala Ser Asp Leu Leu Glu
1               5                   10                  15

Arg Leu Arg Glu Glu Val Thr Lys Leu Arg Met Glu Leu Gln Val Ser
            20                  25                  30
```

```
<210> SEQ ID NO 35
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Phe Lys Ser Gln Glu Leu Asn Glu Arg Asn Glu Ala Ser Asp Leu Leu
1               5                   10                  15

Glu Arg Glu Glu Val Thr Lys Leu Arg Met Glu Leu Gln Val Ser
            20                  25                  30

<210> SEQ ID NO 36
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser Phe Lys Ser Gln Glu Leu Asn Glu Arg Asn Glu Ala Ser Asp Leu
1               5                   10                  15

Leu Glu Arg Leu Arg Glu Glu Val Thr Lys Leu Arg Met Glu Leu Gln
            20                  25                  30

Val Ser

<210> SEQ ID NO 37
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Ser Phe Lys Ser Gln Glu Leu Asn Glu Arg Asn Glu Ala Ser Asp
1               5                   10                  15

Leu Leu Glu Arg Leu Arg Glu Glu Val Thr Lys Leu Arg Met Glu Leu
            20                  25                  30

Gln Val Ser
        35

<210> SEQ ID NO 38
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Leu Ser Ser Phe Lys Ser Gln Glu Leu Asn Glu Arg Asn Glu Ala Ser
1               5                   10                  15

Asp Leu Leu Glu Arg Leu Arg Glu Glu Val Thr Lys Leu Arg Met Glu
            20                  25                  30

Leu Gln Val Ser
        35

<210> SEQ ID NO 39
<211> LENGTH: 37
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 39

```
Asp Leu Ser Ser Phe Lys Ser Gln Glu Leu Asn Glu Arg Asn Glu Ala
1               5                   10                  15

Ser Asp Leu Leu Glu Arg Leu Arg Glu Glu Val Thr Lys Leu Arg Met
            20                  25                  30

Glu Leu Gln Val Ser
        35
```

<210> SEQ ID NO 40
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Ala Asp Leu Ser Ser Phe Lys Ser Gln Glu Leu Asn Glu Arg Asn Glu
1               5                   10                  15

Ala Ser Asp Leu Leu Glu Arg Leu Arg Glu Glu Val Thr Lys Leu Arg
            20                  25                  30

Met Glu Leu Gln Val Ser
        35
```

<210> SEQ ID NO 41
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Gln Ala Asp Leu Ser Ser Phe Lys Ser Gln Glu Leu Asn Glu Arg Asn
1               5                   10                  15

Glu Ala Ser Asp Leu Leu Glu Arg Leu Arg Glu Glu Val Thr Lys Leu
            20                  25                  30

Arg Met Glu Leu Gln Val Ser
        35
```

<210> SEQ ID NO 42
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Leu Gln Ala Asp Leu Ser Ser Phe Lys Ser Gln Glu Leu Asn Glu Arg
1               5                   10                  15

Asn Glu Ala Ser Asp Leu Leu Glu Arg Leu Arg Glu Glu Val Thr Lys
            20                  25                  30

Leu Arg Met Glu Leu Gln Val Ser
        35                  40
```

<210> SEQ ID NO 43
<211> LENGTH: 41

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Leu Gln Ala Asp Leu Ser Ser Phe Lys Ser Gln Glu Leu Asn Glu
1               5                   10                  15

Arg Asn Glu Ala Ser Asp Leu Leu Glu Arg Leu Arg Glu Glu Val Thr
            20                  25                  30

Lys Leu Arg Met Glu Leu Gln Val Ser
        35                  40

<210> SEQ ID NO 44
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asn Gly Leu Gln Ala Asp Leu Ser Ser Phe Lys Ser Gln Glu Leu Asn
1               5                   10                  15

Glu Arg Asn Glu Ala Ser Asp Leu Leu Glu Arg Leu Arg Glu Glu Val
            20                  25                  30

Thr Lys Leu Arg Met Glu Leu Gln Val Ser
        35                  40

<210> SEQ ID NO 45
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Leu Asn Gly Leu Gln Ala Asp Leu Ser Ser Phe Lys Ser Gln Glu Leu
1               5                   10                  15

Asn Glu Arg Asn Glu Ala Ser Asp Leu Leu Glu Arg Leu Arg Glu Glu
            20                  25                  30

Val Thr Lys Leu Arg Met Glu Leu Gln Val Ser
        35                  40

<210> SEQ ID NO 46
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asn Leu Asn Gly Leu Gln Ala Asp Leu Ser Ser Phe Lys Ser Gln Glu
1               5                   10                  15

Leu Asn Glu Arg Asn Glu Ala Ser Asp Leu Leu Glu Arg Leu Arg Glu
            20                  25                  30

Glu Val Thr Lys Leu Arg Met Glu Leu Gln Val Ser
        35                  40

<210> SEQ ID NO 47
```

```
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Trp Asn Leu Asn Gly Leu Gln Ala Asp Leu Ser Ser Phe Lys Ser Gln
1               5                   10                  15

Glu Leu Asn Glu Arg Asn Glu Ala Ser Asp Leu Leu Glu Arg Leu Arg
            20                  25                  30

Glu Glu Val Thr Lys Leu Arg Met Glu Leu Gln Val Ser
        35                  40                  45

<210> SEQ ID NO 48
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ser Trp Asn Leu Asn Gly Leu Gln Ala Asp Leu Ser Ser Phe Lys Ser
1               5                   10                  15

Gln Glu Leu Asn Glu Arg Asn Glu Ala Ser Asp Leu Leu Glu Arg Leu
            20                  25                  30

Arg Glu Glu Val Thr Lys Leu Arg Met Glu Leu Gln Val Ser
        35                  40                  45

<210> SEQ ID NO 49
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Leu Ser Trp Asn Leu Asn Gly Leu Gln Ala Asp Leu Ser Ser Phe Lys
1               5                   10                  15

Ser Gln Glu Leu Asn Glu Arg Asn Glu Ala Ser Asp Leu Leu Glu Arg
            20                  25                  30

Leu Arg Glu Glu Val Thr Lys Leu Arg Met Glu Leu Gln Val Ser
        35                  40                  45

<210> SEQ ID NO 50
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Leu Ser Trp Asn Leu Asn Gly Leu Gln Ala Asp Leu Ser Ser Phe
1               5                   10                  15

Lys Ser Gln Glu Leu Asn Glu Arg Asn Glu Ala Ser Asp Leu Leu Glu
            20                  25                  30

Arg Leu Arg Glu Glu Val Thr Lys Leu Arg Met Glu Leu Gln Val Ser
        35                  40                  45
```

<210> SEQ ID NO 51
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Leu Glu Leu Ser Trp Asn Leu Asn Gly Leu Gln Ala Asp Leu Ser Ser
1               5                   10                  15

Phe Lys Ser Gln Glu Leu Asn Glu Arg Asn Glu Ala Ser Asp Leu Leu
                20                  25                  30

Glu Arg Leu Arg Glu Glu Val Thr Lys Leu Arg Met Glu Leu Gln Val
            35                  40                  45

Ser

<210> SEQ ID NO 52
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Leu Glu Leu Ser Trp Asn Leu Asn Gly Leu Gln Ala Asp Leu Ser
1               5                   10                  15

Ser Phe Lys Ser Gln Glu Leu Asn Glu Arg Asn Glu Ala Ser Asp Leu
                20                  25                  30

Leu Glu Arg Leu Arg Glu Glu Val Thr Lys Leu Arg Met Glu Leu Gln
            35                  40                  45

Val Ser
    50

<210> SEQ ID NO 53
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Asp Leu Glu Leu Ser Trp Asn Leu Asn Gly Leu Gln Ala Asp Leu
1               5                   10                  15

Ser Ser Phe Lys Ser Gln Glu Leu Asn Glu Arg Asn Glu Ala Ser Asp
                20                  25                  30

Leu Leu Glu Arg Leu Arg Glu Glu Val Thr Lys Leu Arg Met Glu Leu
            35                  40                  45

Gln Val Ser
    50

<210> SEQ ID NO 54
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Ser Gln Asp Leu Glu Leu Ser Trp Asn Leu Asn Gly Leu Gln Ala Asp

```
                1               5                  10                 15
Leu Ser Ser Phe Lys Ser Gln Glu Leu Asn Glu Arg Asn Glu Ala Ser
            20                  25                 30

Asp Leu Leu Glu Arg Leu Arg Glu Glu Val Thr Lys Leu Arg Met Glu
        35                  40                 45

Leu Gln Val Ser
    50
```

```
<210> SEQ ID NO 55
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Lys Ser Gln Asp Leu Glu Leu Ser Trp Asn Leu Asn Gly Leu Gln Ala
1               5                   10                  15

Asp Leu Ser Ser Phe Lys Ser Gln Glu Leu Asn Glu Arg Asn Glu Ala
            20                  25                  30

Ser Asp Leu Leu Glu Arg Leu Arg Glu Glu Val Thr Lys Leu Arg Met
        35                  40                  45

Glu Leu Gln Val Ser
    50
```

```
<210> SEQ ID NO 56
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Leu Lys Ser Gln Asp Leu Glu Leu Ser Trp Asn Leu Asn Gly Leu Gln
1               5                   10                  15

Ala Asp Leu Ser Ser Phe Lys Ser Gln Glu Leu Asn Glu Arg Asn Glu
            20                  25                  30

Ala Ser Asp Leu Leu Glu Arg Leu Arg Glu Glu Val Thr Lys Leu Arg
        35                  40                  45

Met Glu Leu Gln Val Ser
    50
```

```
<210> SEQ ID NO 57
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Arg Leu Lys Ser Gln Asp Leu Glu Leu Ser Trp Asn Leu Asn Gly Leu
1               5                   10                  15

Gln Ala Asp Leu Ser Ser Phe Lys Ser Gln Glu Leu Asn Glu Arg Asn
            20                  25                  30

Glu Ala Ser Asp Leu Leu Glu Arg Leu Arg Glu Glu Val Thr Lys Leu
        35                  40                  45

Arg Met Glu Leu Gln Val Ser
    50                  55
```

<210> SEQ ID NO 58
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Arg Leu Lys Ser Gln Asp Leu Glu Leu Ser Trp Asn Leu Asn Gly
1               5                   10                  15

Leu Gln Ala Asp Leu Ser Ser Phe Lys Ser Gln Glu Leu Asn Glu Arg
            20                  25                  30

Asn Glu Ala Ser Asp Leu Leu Glu Arg Leu Arg Glu Glu Val Thr Lys
        35                  40                  45

Leu Arg Met Glu Leu Gln Val Ser
    50                  55

<210> SEQ ID NO 59
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Gln Arg Leu Lys Ser Gln Asp Leu Glu Leu Ser Trp Asn Leu Asn
1               5                   10                  15

Gly Leu Gln Ala Asp Leu Ser Ser Phe Lys Ser Gln Glu Leu Asn Glu
            20                  25                  30

Arg Asn Glu Ala Ser Asp Leu Leu Glu Arg Leu Arg Glu Glu Val Thr
        35                  40                  45

Lys Leu Arg Met Glu Leu Gln Val Ser
    50                  55

<210> SEQ ID NO 60
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Gln Gln Arg Leu Lys Ser Gln Asp Leu Glu Leu Ser Trp Asn Leu
1               5                   10                  15

Asn Gly Leu Gln Ala Asp Leu Ser Ser Phe Lys Ser Gln Glu Leu Asn
            20                  25                  30

Glu Arg Asn Glu Ala Ser Asp Leu Leu Glu Arg Leu Arg Glu Glu Val
        35                  40                  45

Thr Lys Leu Arg Met Glu Leu Gln Val Ser
    50                  55

<210> SEQ ID NO 61
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 61

Ala Glu Gln Gln Arg Leu Lys Ser Gln Asp Leu Glu Leu Ser Trp Asn
1               5                   10                  15

Leu Asn Gly Leu Gln Ala Asp Leu Ser Ser Phe Lys Ser Gln Glu Leu
            20                  25                  30

Asn Glu Arg Asn Glu Ala Ser Asp Leu Leu Glu Arg Leu Arg Glu Glu
        35                  40                  45

Val Thr Lys Leu Arg Met Glu Leu Gln Val Ser
    50                  55

<210> SEQ ID NO 62
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Arg Ala Glu Gln Gln Arg Leu Lys Ser Gln Asp Leu Glu Leu Ser Trp
1               5                   10                  15

Asn Leu Asn Gly Leu Gln Ala Asp Leu Ser Ser Phe Lys Ser Gln Glu
            20                  25                  30

Leu Asn Glu Arg Asn Glu Ala Ser Asp Leu Leu Glu Arg Leu Arg Glu
        35                  40                  45

Glu Val Thr Lys Leu Arg Met Glu Leu Gln Val Ser
    50                  55                  60

<210> SEQ ID NO 63
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Leu Arg Ala Glu Gln Gln Arg Leu Lys Ser Gln Asp Leu Glu Leu Ser
1               5                   10                  15

Trp Asn Leu Asn Gly Leu Gln Ala Asp Leu Ser Ser Phe Lys Ser Gln
            20                  25                  30

Glu Leu Asn Glu Arg Asn Glu Ala Ser Asp Leu Leu Glu Arg Leu Arg
        35                  40                  45

Glu Glu Val Thr Lys Leu Arg Met Glu Leu Gln Val Ser
    50                  55                  60

<210> SEQ ID NO 64
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Leu Arg Ala Glu Gln Gln Arg Leu Lys Ser Gln Asp Leu Glu Leu
1               5                   10                  15

Ser Trp Asn Leu Asn Gly Leu Gln Ala Asp Leu Ser Ser Phe Lys Ser
            20                  25                  30

Gln Glu Leu Asn Glu Arg Asn Glu Ala Ser Asp Leu Leu Glu Arg Leu
        35                  40                  45
```

```
Arg Glu Glu Val Thr Lys Leu Arg Met Glu Leu Gln Val Ser
    50                  55                  60
```

<210> SEQ ID NO 65
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Glu Glu Leu Arg Ala Glu Gln Gln Arg Leu Lys Ser Gln Asp Leu Glu
1               5                   10                  15

Leu Ser Trp Asn Leu Asn Gly Leu Gln Ala Asp Leu Ser Ser Phe Lys
            20                  25                  30

Ser Gln Glu Leu Asn Glu Arg Asn Glu Ala Ser Asp Leu Leu Glu Arg
        35                  40                  45

Leu Arg Glu Glu Val Thr Lys Leu Arg Met Glu Leu Gln Val Ser
    50                  55                  60
```

<210> SEQ ID NO 66
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Leu Glu Glu Leu Arg Ala Glu Gln Gln Arg Leu Lys Ser Gln Asp Leu
1               5                   10                  15

Glu Leu Ser Trp Asn Leu Asn Gly Leu Gln Ala Asp Leu Ser Ser Phe
            20                  25                  30

Lys Ser Gln Glu Leu Asn Glu Arg Asn Glu Ala Ser Asp Leu Leu Glu
        35                  40                  45

Arg Leu Arg Glu Glu Val Thr Lys Leu Arg Met Glu Leu Gln Val Ser
    50                  55                  60
```

<210> SEQ ID NO 67
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Glu Leu Glu Glu Leu Arg Ala Glu Gln Gln Arg Leu Lys Ser Gln Asp
1               5                   10                  15

Leu Glu Leu Ser Trp Asn Leu Asn Gly Leu Gln Ala Asp Leu Ser Ser
            20                  25                  30

Phe Lys Ser Gln Glu Leu Asn Glu Arg Asn Glu Ala Ser Asp Leu Leu
        35                  40                  45

Glu Arg Leu Arg Glu Glu Val Thr Lys Leu Arg Met Glu Leu Gln Val
    50                  55                  60

Ser
65
```

<210> SEQ ID NO 68
<211> LENGTH: 66

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Glu Leu Glu Glu Leu Arg Ala Glu Gln Gln Arg Leu Lys Ser Gln
1               5                   10                  15

Asp Leu Glu Leu Ser Trp Asn Leu Asn Gly Leu Gln Ala Asp Leu Ser
            20                  25                  30

Ser Phe Lys Ser Gln Glu Leu Asn Glu Arg Asn Glu Ala Ser Asp Leu
        35                  40                  45

Leu Glu Arg Leu Arg Glu Glu Val Thr Lys Leu Arg Met Glu Leu Gln
    50                  55                  60

Val Ser
65

<210> SEQ ID NO 69
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ser Gln Glu Leu Glu Glu Leu Arg Ala Glu Gln Gln Arg Leu Lys Ser
1               5                   10                  15

Gln Asp Leu Glu Leu Ser Trp Asn Leu Asn Gly Leu Gln Ala Asp Leu
            20                  25                  30

Ser Ser Phe Lys Ser Gln Glu Leu Asn Glu Arg Asn Glu Ala Ser Asp
        35                  40                  45

Leu Leu Glu Arg Leu Arg Glu Glu Val Thr Lys Leu Arg Met Glu Leu
    50                  55                  60

Gln Val Ser
65

<210> SEQ ID NO 70
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ile Ser Gln Glu Leu Glu Glu Leu Arg Ala Glu Gln Gln Arg Leu Lys
1               5                   10                  15

Ser Gln Asp Leu Glu Leu Ser Trp Asn Leu Asn Gly Leu Gln Ala Asp
            20                  25                  30

Leu Ser Ser Phe Lys Ser Gln Glu Leu Asn Glu Arg Asn Glu Ala Ser
        35                  40                  45

Asp Leu Leu Glu Arg Leu Arg Glu Glu Val Thr Lys Leu Arg Met Glu
    50                  55                  60

Leu Gln Val Ser
65

<210> SEQ ID NO 71
<211> LENGTH: 69
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 71

Gln Ile Ser Gln Glu Leu Glu Glu Leu Arg Ala Glu Gln Gln Arg Leu
1               5                   10                  15

Lys Ser Gln Asp Leu Glu Leu Ser Trp Asn Leu Asn Gly Leu Gln Ala
            20                  25                  30

Asp Leu Ser Ser Phe Lys Ser Gln Glu Leu Asn Glu Arg Asn Glu Ala
        35                  40                  45

Ser Asp Leu Leu Glu Arg Leu Arg Glu Glu Val Thr Lys Leu Arg Met
    50                  55                  60

Glu Leu Gln Val Ser
65

<210> SEQ ID NO 72
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Thr Gln Ile Ser Gln Glu Leu Glu Glu Leu Arg Ala Glu Gln Gln Arg
1               5                   10                  15

Leu Lys Ser Gln Asp Leu Glu Leu Ser Trp Asn Leu Asn Gly Leu Gln
            20                  25                  30

Ala Asp Leu Ser Ser Phe Lys Ser Gln Glu Leu Asn Glu Arg Asn Glu
        35                  40                  45

Ala Ser Asp Leu Leu Glu Arg Leu Arg Glu Glu Val Thr Lys Leu Arg
    50                  55                  60

Met Glu Leu Gln Val Ser
65                  70

<210> SEQ ID NO 73
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ser Thr Gln Ile Ser Gln Glu Leu Glu Glu Leu Arg Ala Glu Gln Gln
1               5                   10                  15

Arg Leu Lys Ser Gln Asp Leu Glu Leu Ser Trp Asn Leu Asn Gly Leu
            20                  25                  30

Gln Ala Asp Leu Ser Ser Phe Lys Ser Gln Glu Leu Asn Glu Arg Asn
        35                  40                  45

Glu Ala Ser Asp Leu Leu Glu Arg Leu Arg Glu Glu Val Thr Lys Leu
    50                  55                  60

Arg Met Glu Leu Gln Val Ser
65                  70

<210> SEQ ID NO 74
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Ser Thr Gln Ile Ser Gln Glu Leu Glu Glu Leu Arg Ala Glu Gln
1               5                   10                  15

Gln Arg Leu Lys Ser Gln Asp Leu Glu Leu Ser Trp Asn Leu Asn Gly
            20                  25                  30

Leu Gln Ala Asp Leu Ser Ser Phe Lys Ser Gln Glu Leu Asn Glu Arg
        35                  40                  45

Asn Glu Ala Ser Asp Leu Leu Glu Arg Leu Arg Glu Glu Val Thr Lys
50                  55                  60

Leu Arg Met Glu Leu Gln Val Ser
65                  70

<210> SEQ ID NO 75
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Ser Gln Ser Thr Gln Ile Ser Gln Glu Leu Glu Glu Leu Arg Ala Glu
1               5                   10                  15

Gln Gln Arg Leu Lys Ser Gln Asp Leu Glu Leu Ser Trp Asn Leu Asn
            20                  25                  30

Gly Leu Gln Ala Asp Leu Ser Ser Phe Lys Ser Gln Glu Leu Asn Glu
        35                  40                  45

Arg Asn Glu Ala Ser Asp Leu Leu Glu Arg Leu Arg Glu Glu Val Thr
    50                  55                  60

Lys Leu Arg Met Glu Leu Gln Val Ser
65                  70

<210> SEQ ID NO 76
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Lys Ser Gln Ser Thr Gln Ile Ser Gln Glu Leu Glu Glu Leu Arg Ala
1               5                   10                  15

Glu Gln Gln Arg Leu Lys Ser Gln Asp Leu Glu Leu Ser Trp Asn Leu
            20                  25                  30

Asn Gly Leu Gln Ala Asp Leu Ser Ser Phe Lys Ser Gln Glu Leu Asn
        35                  40                  45

Glu Arg Asn Glu Ala Ser Asp Leu Leu Glu Arg Leu Arg Glu Glu Val
    50                  55                  60

Thr Lys Leu Arg Met Glu Leu Gln Val Ser
65                  70

<210> SEQ ID NO 77
<211> LENGTH: 75
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 77

Gln Lys Ser Gln Ser Thr Gln Ile Ser Gln Glu Leu Glu Glu Leu Arg
1               5                   10                  15

Ala Glu Gln Gln Arg Leu Lys Ser Gln Asp Leu Glu Leu Ser Trp Asn
            20                  25                  30

Leu Asn Gly Leu Gln Ala Asp Leu Ser Ser Phe Lys Ser Gln Glu Leu
        35                  40                  45

Asn Glu Arg Asn Glu Ala Ser Asp Leu Leu Glu Arg Leu Arg Glu Glu
    50                  55                  60

Val Thr Lys Leu Arg Met Glu Leu Gln Val Ser
65                  70                  75

<210> SEQ ID NO 78
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ala Gln Lys Ser Gln Ser Thr Gln Ile Ser Gln Glu Leu Glu Glu Leu
1               5                   10                  15

Arg Ala Glu Gln Gln Arg Leu Lys Ser Gln Asp Leu Glu Leu Ser Trp
            20                  25                  30

Asn Leu Asn Gly Leu Gln Ala Asp Leu Ser Ser Phe Lys Ser Gln Glu
        35                  40                  45

Leu Asn Glu Arg Asn Glu Ala Ser Asp Leu Leu Glu Arg Leu Arg Glu
    50                  55                  60

Glu Val Thr Lys Leu Arg Met Glu Leu Gln Val Ser
65                  70                  75

<210> SEQ ID NO 79
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Ala Gln Lys Ser Gln Ser Thr Gln Ile Ser Gln Glu Leu Glu Glu
1               5                   10                  15

Leu Arg Ala Glu Gln Gln Arg Leu Lys Ser Gln Asp Leu Glu Leu Ser
            20                  25                  30

Trp Asn Leu Asn Gly Leu Gln Ala Asp Leu Ser Ser Phe Lys Ser Gln
        35                  40                  45

Glu Leu Asn Glu Arg Asn Glu Ala Ser Asp Leu Leu Glu Arg Leu Arg
    50                  55                  60

Glu Glu Val Thr Lys Leu Arg Met Glu Leu Gln Val Ser
65                  70                  75

<210> SEQ ID NO 80
<211> LENGTH: 78
<212> TYPE: PRT
<213> ORGANISM: Artificial Sequence
<220> FEATURE:
<223> OTHER INFORMATION: Description of Artificial Sequence: Synthetic

```
                        polypeptide

<400> SEQUENCE: 80

Gln Met Ala Gln Lys Ser Gln Ser Thr Gln Ile Ser Gln Glu Leu Glu
1               5                   10                  15

Glu Leu Arg Ala Glu Gln Gln Arg Leu Lys Ser Gln Asp Leu Glu Leu
            20                  25                  30

Ser Trp Asn Leu Asn Gly Leu Gln Ala Asp Leu Ser Ser Phe Lys Ser
        35                  40                  45

Gln Glu Leu Asn Glu Arg Asn Glu Ala Ser Asp Leu Leu Glu Arg Leu
    50                  55                  60

Arg Glu Glu Val Thr Lys Leu Arg Met Glu Leu Gln Val Ser
65                  70                  75

<210> SEQ ID NO 81
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Gln Met Ala Gln Lys Ser Gln Ser Thr Gln Ile Ser Gln Glu Leu
1               5                   10                  15

Glu Glu Leu Arg Ala Glu Gln Gln Arg Leu Lys Ser Gln Asp Leu Glu
            20                  25                  30

Leu Ser Trp Asn Leu Asn Gly Leu Gln Ala Asp Leu Ser Ser Phe Lys
        35                  40                  45

Ser Gln Glu Leu Asn Glu Arg Asn Glu Ala Ser Asp Leu Leu Glu Arg
    50                  55                  60

Leu Arg Glu Glu Val Thr Lys Leu Arg Met Glu Leu Gln Val Ser
65                  70                  75

<210> SEQ ID NO 82
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gly Asp Gln Met Ala Gln Lys Ser Gln Ser Thr Gln Ile Ser Gln Glu
1               5                   10                  15

Leu Glu Glu Leu Arg Ala Glu Gln Gln Arg Leu Lys Ser Gln Asp Leu
            20                  25                  30

Glu Leu Ser Trp Asn Leu Asn Gly Leu Gln Ala Asp Leu Ser Ser Phe
        35                  40                  45

Lys Ser Gln Glu Leu Asn Glu Arg Asn Glu Ala Ser Asp Leu Leu Glu
    50                  55                  60

Arg Leu Arg Glu Glu Val Thr Lys Leu Arg Met Glu Leu Gln Val Ser
65                  70                  75                  80

<210> SEQ ID NO 83
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 83

His Gly Asp Gln Met Ala Gln Lys Ser Gln Ser Thr Gln Ile Ser Gln
1               5                   10                  15

Glu Leu Glu Glu Leu Arg Ala Glu Gln Gln Arg Leu Lys Ser Gln Asp
            20                  25                  30

Leu Glu Leu Ser Trp Asn Leu Asn Gly Leu Gln Ala Asp Leu Ser Ser
        35                  40                  45

Phe Lys Ser Gln Glu Leu Asn Glu Arg Asn Glu Ala Ser Asp Leu Leu
    50                  55                  60

Glu Arg Leu Arg Glu Glu Val Thr Lys Leu Arg Met Glu Leu Gln Val
65                  70                  75                  80

Ser

<210> SEQ ID NO 84
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

His His Gly Asp Gln Met Ala Gln Lys Ser Gln Ser Thr Gln Ile Ser
1               5                   10                  15

Gln Glu Leu Glu Glu Leu Arg Ala Glu Gln Gln Arg Leu Lys Ser Gln
            20                  25                  30

Asp Leu Glu Leu Ser Trp Asn Leu Asn Gly Leu Gln Ala Asp Leu Ser
        35                  40                  45

Ser Phe Lys Ser Gln Glu Leu Asn Glu Arg Asn Glu Ala Ser Asp Leu
    50                  55                  60

Leu Glu Arg Leu Arg Glu Glu Val Thr Lys Leu Arg Met Glu Leu Gln
65                  70                  75                  80

Val Ser

<210> SEQ ID NO 85
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Ser His His Gly Asp Gln Met Ala Gln Lys Ser Gln Ser Thr Gln Ile
1               5                   10                  15

Ser Gln Glu Leu Glu Glu Leu Arg Ala Glu Gln Gln Arg Leu Lys Ser
            20                  25                  30

Gln Asp Leu Glu Leu Ser Trp Asn Leu Asn Gly Leu Gln Ala Asp Leu
        35                  40                  45

Ser Ser Phe Lys Ser Gln Glu Leu Asn Glu Arg Asn Glu Ala Ser Asp
    50                  55                  60

Leu Leu Glu Arg Leu Arg Glu Glu Val Thr Lys Leu Arg Met Glu Leu
65                  70                  75                  80

Gln Val Ser

<210> SEQ ID NO 86
<211> LENGTH: 84

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Ser His His Gly Asp Gln Met Ala Gln Lys Ser Gln Ser Thr Gln
1               5                   10                  15

Ile Ser Gln Glu Leu Glu Glu Leu Arg Ala Glu Gln Gln Arg Leu Lys
            20                  25                  30

Ser Gln Asp Leu Glu Leu Ser Trp Asn Leu Asn Gly Leu Gln Ala Asp
        35                  40                  45

Leu Ser Ser Phe Lys Ser Gln Glu Leu Asn Glu Arg Asn Glu Ala Ser
    50                  55                  60

Asp Leu Leu Glu Arg Leu Arg Glu Glu Val Thr Lys Leu Arg Met Glu
65                  70                  75                  80

Leu Gln Val Ser

<210> SEQ ID NO 87
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Leu Glu Ser His His Gly Asp Gln Met Ala Gln Lys Ser Gln Ser Thr
1               5                   10                  15

Gln Ile Ser Gln Glu Leu Glu Glu Leu Arg Ala Glu Gln Gln Arg Leu
            20                  25                  30

Lys Ser Gln Asp Leu Glu Leu Ser Trp Asn Leu Asn Gly Leu Gln Ala
        35                  40                  45

Asp Leu Ser Ser Phe Lys Ser Gln Glu Leu Asn Glu Arg Asn Glu Ala
    50                  55                  60

Ser Asp Leu Leu Glu Arg Leu Arg Glu Glu Val Thr Lys Leu Arg Met
65                  70                  75                  80

Glu Leu Gln Val Ser
                85

<210> SEQ ID NO 88
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asn Leu Glu Ser His His Gly Asp Gln Met Ala Gln Lys Ser Gln Ser
1               5                   10                  15

Thr Gln Ile Ser Gln Glu Leu Glu Glu Leu Arg Ala Glu Gln Gln Arg
            20                  25                  30

Leu Lys Ser Gln Asp Leu Glu Leu Ser Trp Asn Leu Asn Gly Leu Gln
        35                  40                  45

Ala Asp Leu Ser Ser Phe Lys Ser Gln Glu Leu Asn Glu Arg Asn Glu
    50                  55                  60

Ala Ser Asp Leu Leu Glu Arg Leu Arg Glu Glu Val Thr Lys Leu Arg
65                  70                  75                  80

```
Met Glu Leu Gln Val Ser
            85

<210> SEQ ID NO 89
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Lys Asn Leu Glu Ser His His Gly Asp Gln Met Ala Gln Lys Ser Gln
1               5                   10                  15

Ser Thr Gln Ile Ser Gln Glu Leu Glu Glu Leu Arg Ala Glu Gln Gln
            20                  25                  30

Arg Leu Lys Ser Gln Asp Leu Glu Leu Ser Trp Asn Leu Asn Gly Leu
        35                  40                  45

Gln Ala Asp Leu Ser Ser Phe Lys Ser Gln Glu Leu Asn Glu Arg Asn
    50                  55                  60

Glu Ala Ser Asp Leu Leu Glu Arg Leu Arg Glu Glu Val Thr Lys Leu
65                  70                  75                  80

Arg Met Glu Leu Gln Val Ser
            85

<210> SEQ ID NO 90
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ser Lys Asn Leu Glu Ser His His Gly Asp Gln Met Ala Gln Lys Ser
1               5                   10                  15

Gln Ser Thr Gln Ile Ser Gln Glu Leu Glu Glu Leu Arg Ala Glu Gln
            20                  25                  30

Gln Arg Leu Lys Ser Gln Asp Leu Glu Leu Ser Trp Asn Leu Asn Gly
        35                  40                  45

Leu Gln Ala Asp Leu Ser Ser Phe Lys Ser Gln Glu Leu Asn Glu Arg
    50                  55                  60

Asn Glu Ala Ser Asp Leu Leu Glu Arg Leu Arg Glu Glu Val Thr Lys
65                  70                  75                  80

Leu Arg Met Glu Leu Gln Val Ser
            85

<210> SEQ ID NO 91
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Val Ser Lys Asn Leu Glu Ser His His Gly Asp Gln Met Ala Gln Lys
1               5                   10                  15

Ser Gln Ser Thr Gln Ile Ser Gln Glu Leu Glu Glu Leu Arg Ala Glu
            20                  25                  30
```

Gln Gln Arg Leu Lys Ser Gln Asp Leu Glu Leu Ser Trp Asn Leu Asn
            35                  40                  45

Gly Leu Gln Ala Asp Leu Ser Ser Phe Lys Ser Gln Glu Leu Asn Glu
 50                  55                  60

Arg Asn Glu Ala Ser Asp Leu Leu Glu Arg Leu Arg Glu Glu Val Thr
 65                  70                  75                  80

Lys Leu Arg Met Glu Leu Gln Val Ser
                 85

<210> SEQ ID NO 92
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Ser Lys Asn Leu Glu Ser His His Gly Asp Gln Met Ala Gln
 1               5                   10                  15

Lys Ser Gln Ser Thr Gln Ile Ser Gln Glu Leu Glu Glu Leu Arg Ala
            20                  25                  30

Glu Gln Gln Arg Leu Lys Ser Gln Asp Leu Glu Leu Ser Trp Asn Leu
            35                  40                  45

Asn Gly Leu Gln Ala Asp Leu Ser Ser Phe Lys Ser Gln Glu Leu Asn
 50                  55                  60

Glu Arg Asn Glu Ala Ser Asp Leu Leu Glu Arg Leu Arg Glu Glu Val
 65                  70                  75                  80

Thr Lys Leu Arg Met Glu Leu Gln Val Ser
                 85                  90

<210> SEQ ID NO 93
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Ser Gln Val Ser Lys Asn Leu Glu Ser His His Gly Asp Gln Met Ala
 1               5                   10                  15

Gln Lys Ser Gln Ser Thr Gln Ile Ser Gln Glu Leu Glu Glu Leu Arg
            20                  25                  30

Ala Glu Gln Gln Arg Leu Lys Ser Gln Asp Leu Glu Leu Ser Trp Asn
            35                  40                  45

Leu Asn Gly Leu Gln Ala Asp Leu Ser Ser Phe Lys Ser Gln Glu Leu
 50                  55                  60

Asn Glu Arg Asn Glu Ala Ser Asp Leu Leu Glu Arg Leu Arg Glu Glu
 65                  70                  75                  80

Val Thr Lys Leu Arg Met Glu Leu Gln Val Ser
                 85                  90

<210> SEQ ID NO 94
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 94

Val Ser Gln Val Ser Lys Asn Leu Glu Ser His His Gly Asp Gln Met
1               5                   10                  15

Ala Gln Lys Ser Gln Ser Thr Gln Ile Ser Gln Glu Leu Glu Glu Leu
            20                  25                  30

Arg Ala Glu Gln Gln Arg Leu Lys Ser Gln Asp Leu Glu Leu Ser Trp
        35                  40                  45

Asn Leu Asn Gly Leu Gln Ala Asp Leu Ser Ser Phe Lys Ser Gln Glu
    50                  55                  60

Leu Asn Glu Arg Asn Glu Ala Ser Asp Leu Leu Glu Arg Leu Arg Glu
65                  70                  75                  80

Glu Val Thr Lys Leu Arg Met Glu Leu Gln Val Ser
                85                  90

<210> SEQ ID NO 95
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Asn Val Ser Gln Val Ser Lys Asn Leu Glu Ser His His Gly Asp Gln
1               5                   10                  15

Met Ala Gln Lys Ser Gln Ser Thr Gln Ile Ser Gln Glu Leu Glu Glu
            20                  25                  30

Leu Arg Ala Glu Gln Gln Arg Leu Lys Ser Gln Asp Leu Glu Leu Ser
        35                  40                  45

Trp Asn Leu Asn Gly Leu Gln Ala Asp Leu Ser Ser Phe Lys Ser Gln
    50                  55                  60

Glu Leu Asn Glu Arg Asn Glu Ala Ser Asp Leu Leu Glu Arg Leu Arg
65                  70                  75                  80

Glu Glu Val Thr Lys Leu Arg Met Glu Leu Gln Val Ser
                85                  90

<210> SEQ ID NO 96
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Arg Asn Val Ser Gln Val Ser Lys Asn Leu Glu Ser His His Gly Asp
1               5                   10                  15

Gln Met Ala Gln Lys Ser Gln Ser Thr Gln Ile Ser Gln Glu Leu Glu
            20                  25                  30

Glu Leu Arg Ala Glu Gln Gln Arg Leu Lys Ser Gln Asp Leu Glu Leu
        35                  40                  45

Ser Trp Asn Leu Asn Gly Leu Gln Ala Asp Leu Ser Ser Phe Lys Ser
    50                  55                  60

Gln Glu Leu Asn Glu Arg Asn Glu Ala Ser Asp Leu Leu Glu Arg Leu
65                  70                  75                  80

Arg Glu Glu Val Thr Lys Leu Arg Met Glu Leu Gln Val Ser
                85                  90
```

```
<210> SEQ ID NO 97
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ala Arg Asn Val Ser Gln Val Ser Lys Asn Leu Glu Ser His His Gly
1               5                   10                  15

Asp Gln Met Ala Gln Lys Ser Gln Ser Thr Gln Ile Ser Gln Glu Leu
            20                  25                  30

Glu Glu Leu Arg Ala Glu Gln Gln Arg Leu Lys Ser Gln Asp Leu Glu
        35                  40                  45

Leu Ser Trp Asn Leu Asn Gly Leu Gln Ala Asp Leu Ser Ser Phe Lys
    50                  55                  60

Ser Gln Glu Leu Asn Glu Arg Asn Glu Ala Ser Asp Leu Leu Glu Arg
65                  70                  75                  80

Leu Arg Glu Glu Val Thr Lys Leu Arg Met Glu Leu Gln Val Ser
                85                  90                  95

<210> SEQ ID NO 98
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ala Ala Arg Asn Val Ser Gln Val Ser Lys Asn Leu Glu Ser His His
1               5                   10                  15

Gly Asp Gln Met Ala Gln Lys Ser Gln Ser Thr Gln Ile Ser Gln Glu
            20                  25                  30

Leu Glu Glu Leu Arg Ala Glu Gln Gln Arg Leu Lys Ser Gln Asp Leu
        35                  40                  45

Glu Leu Ser Trp Asn Leu Asn Gly Leu Gln Ala Asp Leu Ser Ser Phe
    50                  55                  60

Lys Ser Gln Glu Leu Asn Glu Arg Asn Glu Ala Ser Asp Leu Leu Glu
65                  70                  75                  80

Arg Leu Arg Glu Glu Val Thr Lys Leu Arg Met Glu Leu Gln Val Ser
                85                  90                  95

<210> SEQ ID NO 99
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Arg Ala Ala Arg Asn Val Ser Gln Val Ser Lys Asn Leu Glu Ser His
1               5                   10                  15

His Gly Asp Gln Met Ala Gln Lys Ser Gln Ser Thr Gln Ile Ser Gln
            20                  25                  30

Glu Leu Glu Glu Leu Arg Ala Glu Gln Gln Arg Leu Lys Ser Gln Asp
        35                  40                  45

Leu Glu Leu Ser Trp Asn Leu Asn Gly Leu Gln Ala Asp Leu Ser Ser
    50                  55                  60
```

Phe Lys Ser Gln Glu Leu Asn Glu Arg Asn Glu Ala Ser Asp Leu Leu
65                  70                  75                  80

Glu Arg Leu Arg Glu Val Thr Lys Leu Arg Met Glu Leu Gln Val
                85                  90                  95

Ser

<210> SEQ ID NO 100
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Arg Ala Ala Arg Asn Val Ser Gln Val Ser Lys Asn Leu Glu Ser
1               5                   10                  15

His His Gly Asp Gln Met Ala Gln Lys Ser Gln Ser Thr Gln Ile Ser
            20                  25                  30

Gln Glu Leu Glu Glu Leu Arg Ala Glu Gln Gln Arg Leu Lys Ser Gln
        35                  40                  45

Asp Leu Glu Leu Ser Trp Asn Leu Asn Gly Leu Gln Ala Asp Leu Ser
    50                  55                  60

Ser Phe Lys Ser Gln Leu Asn Glu Arg Asn Glu Ala Ser Asp Leu
65                  70                  75                  80

Leu Glu Arg Leu Arg Glu Val Thr Lys Leu Arg Met Glu Leu Gln
                85                  90                  95

Val Ser

<210> SEQ ID NO 101
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Glu Arg Ala Ala Arg Asn Val Ser Gln Val Ser Lys Asn Leu Glu
1               5                   10                  15

Ser His His Gly Asp Gln Met Ala Gln Lys Ser Gln Ser Thr Gln Ile
            20                  25                  30

Ser Gln Glu Leu Glu Glu Leu Arg Ala Glu Gln Gln Arg Leu Lys Ser
        35                  40                  45

Gln Asp Leu Glu Leu Ser Trp Asn Leu Asn Gly Leu Gln Ala Asp Leu
    50                  55                  60

Ser Ser Phe Lys Ser Gln Leu Asn Glu Arg Asn Glu Ala Ser Asp
65                  70                  75                  80

Leu Leu Glu Arg Leu Arg Glu Val Thr Lys Leu Arg Met Glu Leu
                85                  90                  95

Gln Val Ser

<210> SEQ ID NO 102
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Leu Glu Glu Arg Ala Ala Arg Asn Val Ser Gln Val Ser Lys Asn Leu
1               5                   10                  15

Glu Ser His His Gly Asp Gln Met Ala Gln Lys Ser Gln Ser Thr Gln
            20                  25                  30

Ile Ser Gln Glu Leu Glu Glu Leu Arg Ala Glu Gln Gln Arg Leu Lys
        35                  40                  45

Ser Gln Asp Leu Glu Leu Ser Trp Asn Leu Asn Gly Leu Gln Ala Asp
    50                  55                  60

Leu Ser Ser Phe Lys Ser Gln Glu Leu Asn Glu Arg Asn Glu Ala Ser
65              70                  75                  80

Asp Leu Glu Arg Leu Arg Glu Glu Val Thr Lys Leu Arg Met Glu
            85                  90                  95

Leu Gln Val Ser
            100

<210> SEQ ID NO 103
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Leu Glu Glu Arg Ala Ala Arg Asn Val Ser Gln Val Ser Lys Asn
1               5                   10                  15

Leu Glu Ser His His Gly Asp Gln Met Ala Gln Lys Ser Gln Ser Thr
            20                  25                  30

Gln Ile Ser Gln Glu Leu Glu Glu Leu Arg Ala Glu Gln Gln Arg Leu
        35                  40                  45

Lys Ser Gln Asp Leu Glu Leu Ser Trp Asn Leu Asn Gly Leu Gln Ala
    50                  55                  60

Asp Leu Ser Ser Phe Lys Ser Gln Glu Leu Asn Glu Arg Asn Glu Ala
65              70                  75                  80

Ser Asp Leu Leu Glu Arg Leu Arg Glu Glu Val Thr Lys Leu Arg Met
            85                  90                  95

Glu Leu Gln Val Ser
            100

<210> SEQ ID NO 104
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Lys Gln Leu Glu Glu Arg Ala Ala Arg Asn Val Ser Gln Val Ser Lys
1               5                   10                  15

Asn Leu Glu Ser His His Gly Asp Gln Met Ala Gln Lys Ser Gln Ser
            20                  25                  30

Thr Gln Ile Ser Gln Glu Leu Glu Glu Leu Arg Ala Glu Gln Gln Arg
        35                  40                  45

Leu Lys Ser Gln Asp Leu Glu Leu Ser Trp Asn Leu Asn Gly Leu Gln
    50                  55                  60

Ala Asp Leu Ser Ser Phe Lys Ser Gln Glu Leu Asn Glu Arg Asn Glu
65                  70                  75                  80

Ala Ser Asp Leu Leu Glu Arg Leu Arg Glu Glu Val Thr Lys Leu Arg
                85                  90                  95

Met Glu Leu Gln Val Ser
            100

<210> SEQ ID NO 105
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Leu Lys Gln Leu Glu Glu Arg Ala Ala Arg Asn Val Ser Gln Val Ser
1               5                   10                  15

Lys Asn Leu Glu Ser His His Gly Asp Gln Met Ala Gln Lys Ser Gln
                20                  25                  30

Ser Thr Gln Ile Ser Gln Glu Leu Glu Glu Leu Arg Ala Glu Gln Gln
            35                  40                  45

Arg Leu Lys Ser Gln Asp Leu Glu Leu Ser Trp Asn Leu Asn Gly Leu
    50                  55                  60

Gln Ala Asp Leu Ser Ser Phe Lys Ser Gln Glu Leu Asn Glu Arg Asn
65                  70                  75                  80

Glu Ala Ser Asp Leu Leu Glu Arg Leu Arg Glu Glu Val Thr Lys Leu
                85                  90                  95

Arg Met Glu Leu Gln Val Ser
            100

<210> SEQ ID NO 106
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Ser Leu Lys Gln Leu Glu Glu Arg Ala Ala Arg Asn Val Ser Gln Val
1               5                   10                  15

Ser Lys Asn Leu Glu Ser His His Gly Asp Gln Met Ala Gln Lys Ser
                20                  25                  30

Gln Ser Thr Gln Ile Ser Gln Glu Leu Glu Glu Leu Arg Ala Glu Gln
            35                  40                  45

Gln Arg Leu Lys Ser Gln Asp Leu Glu Leu Ser Trp Asn Leu Asn Gly
    50                  55                  60

Leu Gln Ala Asp Leu Ser Ser Phe Lys Ser Gln Glu Leu Asn Glu Arg
65                  70                  75                  80

Asn Glu Ala Ser Asp Leu Leu Glu Arg Leu Arg Glu Glu Val Thr Lys
                85                  90                  95

Leu Arg Met Glu Leu Gln Val Ser
            100

<210> SEQ ID NO 107
<211> LENGTH: 105
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 107

Gln Ser Leu Lys Gln Leu Glu Glu Arg Ala Ala Arg Asn Val Ser Gln
1               5                   10                  15

Val Ser Lys Asn Leu Glu Ser His His Gly Asp Gln Met Ala Gln Lys
            20                  25                  30

Ser Gln Ser Thr Gln Ile Ser Gln Glu Leu Glu Glu Leu Arg Ala Glu
        35                  40                  45

Gln Gln Arg Leu Lys Ser Gln Asp Leu Glu Leu Ser Trp Asn Leu Asn
    50                  55                  60

Gly Leu Gln Ala Asp Leu Ser Ser Phe Lys Ser Gln Glu Leu Asn Glu
65                  70                  75                  80

Arg Asn Glu Ala Ser Asp Leu Leu Glu Arg Leu Arg Glu Glu Val Thr
                85                  90                  95

Lys Leu Arg Met Glu Leu Gln Val Ser
            100                 105

<210> SEQ ID NO 108
<211> LENGTH: 106
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 108

Thr Gln Ser Leu Lys Gln Leu Glu Glu Arg Ala Ala Arg Asn Val Ser
1               5                   10                  15

Gln Val Ser Lys Asn Leu Glu Ser His His Gly Asp Gln Met Ala Gln
            20                  25                  30

Lys Ser Gln Ser Thr Gln Ile Ser Gln Glu Leu Glu Glu Leu Arg Ala
        35                  40                  45

Glu Gln Gln Arg Leu Lys Ser Gln Asp Leu Glu Leu Ser Trp Asn Leu
    50                  55                  60

Asn Gly Leu Gln Ala Asp Leu Ser Ser Phe Lys Ser Gln Glu Leu Asn
65                  70                  75                  80

Glu Arg Asn Glu Ala Ser Asp Leu Leu Glu Arg Leu Arg Glu Glu Val
                85                  90                  95

Thr Lys Leu Arg Met Glu Leu Gln Val Ser
            100                 105

<210> SEQ ID NO 109
<211> LENGTH: 106
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 109

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn

```
                        50                  55                  60
Leu Asn Gly Leu Gln Ala Asp Leu Ser Ser Phe Lys Ser Gln Glu Leu
 65                  70                  75                  80

Asn Glu Arg Asn Glu Ala Ser Asp Leu Leu Glu Arg Leu Arg Glu Glu
                 85                  90                  95

Val Thr Lys Leu Arg Met Glu Leu Gln Val
            100                 105

<210> SEQ ID NO 110
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Thr Thr Gln Ser Leu Lys Gln Leu Glu Glu Arg Ala Ala Arg Asn Val
 1               5                  10                  15

Ser Gln Val Ser Lys Asn Leu Glu Ser His His Gly Asp Gln Met Ala
                20                  25                  30

Gln Lys Ser Gln Ser Thr Gln Ile Ser Gln Glu Leu Glu Glu Leu Arg
            35                  40                  45

Ala Glu Gln Gln Arg Leu Lys Ser Gln Asp Leu Glu Leu Ser Trp Asn
 50                  55                  60

Leu Asn Gly Leu Gln Ala Asp Leu Ser Ser Phe Lys Ser Gln Glu Leu
 65                  70                  75                  80

Asn Glu Arg Asn Glu Ala Ser Asp Leu Leu Glu Arg Leu Arg Glu Glu
                 85                  90                  95

Val Thr Lys Leu Arg Met Glu Leu Gln
            100                 105

<210> SEQ ID NO 111
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Thr Thr Gln Ser Leu Lys Gln Leu Glu Glu Arg Ala Ala Arg Asn Val
 1               5                  10                  15

Ser Gln Val Ser Lys Asn Leu Glu Ser His His Gly Asp Gln Met Ala
                20                  25                  30

Gln Lys Ser Gln Ser Thr Gln Ile Ser Gln Glu Leu Glu Glu Leu Arg
            35                  40                  45

Ala Glu Gln Gln Arg Leu Lys Ser Gln Asp Leu Glu Leu Ser Trp Asn
 50                  55                  60

Leu Asn Gly Leu Gln Ala Asp Leu Ser Ser Phe Lys Ser Gln Glu Leu
 65                  70                  75                  80

Asn Glu Arg Asn Glu Ala Ser Asp Leu Leu Glu Arg Leu Arg Glu Glu
                 85                  90                  95

Val Thr Lys Leu Arg Met Glu Leu
            100

<210> SEQ ID NO 112
<211> LENGTH: 103
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 112

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala Ser Asp Leu Leu Glu Arg Leu Arg Glu Glu
                85                  90                  95

Val Thr Lys Leu Arg Met Glu
            100

<210> SEQ ID NO 113
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala Ser Asp Leu Leu Glu Arg Leu Arg Glu Glu
                85                  90                  95

Val Thr Lys Leu Arg Met
            100

<210> SEQ ID NO 114
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45
```

```
Ala Glu Gln Gln Arg Leu Lys Ser Gln Asp Leu Glu Leu Ser Trp Asn
         50                  55                  60

Leu Asn Gly Leu Gln Ala Asp Leu Ser Ser Phe Lys Ser Gln Glu Leu
 65                  70                  75                  80

Asn Glu Arg Asn Glu Ala Ser Asp Leu Leu Glu Arg Leu Arg Glu Glu
                 85                  90                  95

Val Thr Lys Leu Arg
            100

<210> SEQ ID NO 115
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Thr Thr Gln Ser Leu Lys Gln Leu Glu Glu Arg Ala Ala Arg Asn Val
 1               5                  10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
 65                  70                  75                  80

Asn Glu Arg Asn Glu Ala Ser Asp Leu Leu Glu Arg Leu Arg Glu Glu
                 85                  90                  95

Val Thr Lys Leu
            100

<210> SEQ ID NO 116
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Thr Thr Gln Ser Leu Lys Gln Leu Glu Glu Arg Ala Ala Arg Asn Val
 1               5                  10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
 65                  70                  75                  80

Asn Glu Arg Asn Glu Ala Ser Asp Leu Leu Glu Arg Leu Arg Glu Glu
                 85                  90                  95

Val Thr Lys

<210> SEQ ID NO 117
<211> LENGTH: 98
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala Ser Asp Leu Leu Glu Arg Leu Arg Glu Glu
                85                  90                  95

Val Thr

<210> SEQ ID NO 118
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala Ser Asp Leu Leu Glu Arg Leu Arg Glu Glu
                85                  90                  95

Val

<210> SEQ ID NO 119
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45
```

```
Ala Glu Gln Gln Arg Leu Lys Ser Gln Asp Leu Glu Leu Ser Trp Asn
 50                  55                  60

Leu Asn Gly Leu Gln Ala Asp Leu Ser Ser Phe Lys Ser Gln Glu Leu
 65                  70                  75                  80

Asn Glu Arg Asn Glu Ala Ser Asp Leu Leu Glu Arg Leu Arg Glu Glu
                 85                  90                  95
```

<210> SEQ ID NO 120
<211> LENGTH: 95
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 120

```
Thr Thr Gln Ser Leu Lys Gln Leu Glu Glu Arg Ala Ala Arg Asn Val
 1               5                  10                  15

Ser Gln Val Ser Lys Asn Leu Glu Ser His His Gly Asp Gln Met Ala
                 20                  25                  30

Gln Lys Ser Gln Ser Thr Gln Ile Ser Gln Glu Leu Glu Glu Leu Arg
             35                  40                  45

Ala Glu Gln Gln Arg Leu Lys Ser Gln Asp Leu Glu Leu Ser Trp Asn
 50                  55                  60

Leu Asn Gly Leu Gln Ala Asp Leu Ser Ser Phe Lys Ser Gln Glu Leu
 65                  70                  75                  80

Asn Glu Arg Asn Glu Ala Ser Asp Leu Leu Glu Arg Leu Arg Glu
                 85                  90                  95
```

<210> SEQ ID NO 121
<211> LENGTH: 94
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 121

```
Thr Thr Gln Ser Leu Lys Gln Leu Glu Glu Arg Ala Ala Arg Asn Val
 1               5                  10                  15

Ser Gln Val Ser Lys Asn Leu Glu Ser His His Gly Asp Gln Met Ala
                 20                  25                  30

Gln Lys Ser Gln Ser Thr Gln Ile Ser Gln Glu Leu Glu Glu Leu Arg
             35                  40                  45

Ala Glu Gln Gln Arg Leu Lys Ser Gln Asp Leu Glu Leu Ser Trp Asn
 50                  55                  60

Leu Asn Gly Leu Gln Ala Asp Leu Ser Ser Phe Lys Ser Gln Glu Leu
 65                  70                  75                  80

Asn Glu Arg Asn Glu Ala Ser Asp Leu Leu Glu Arg Leu Arg
                 85                  90
```

<210> SEQ ID NO 122
<211> LENGTH: 93
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 122

```
Thr Thr Gln Ser Leu Lys Gln Leu Glu Glu Arg Ala Ala Arg Asn Val
```

```
                1               5                  10                  15
Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala Ser Asp Leu Leu Glu Arg Leu
                85                  90
```

<210> SEQ ID NO 123
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

```
Thr Thr Gln Ser Leu Lys Gln Leu Glu Glu Arg Ala Ala Arg Asn Val
1               5                  10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala Ser Asp Leu Leu Glu Arg
                85                  90
```

<210> SEQ ID NO 124
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

```
Thr Thr Gln Ser Leu Lys Gln Leu Glu Glu Arg Ala Ala Arg Asn Val
1               5                  10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala Ser Asp Leu Leu Glu
                85                  90
```

<210> SEQ ID NO 125
<211> LENGTH: 90
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 125

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala Ser Asp Leu Leu
                85                  90

<210> SEQ ID NO 126
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala Ser Asp Leu
                85

<210> SEQ ID NO 127
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala Ser Asp
                85

<210> SEQ ID NO 128
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala Ser
                85

<210> SEQ ID NO 129
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala
                85

<210> SEQ ID NO 130
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
            35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu
            85

<210> SEQ ID NO 131
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
            35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn

<210> SEQ ID NO 132
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
            35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg

<210> SEQ ID NO 133
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

```
Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu

<210> SEQ ID NO 134
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn

<210> SEQ ID NO 135
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

<210> SEQ ID NO 136
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 136

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu
65                  70                  75

<210> SEQ ID NO 137
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln
65                  70                  75

<210> SEQ ID NO 138
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser
65                  70                  75

<210> SEQ ID NO 139
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 139

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys
65                  70                  75

<210> SEQ ID NO 140
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe
65                  70                  75

<210> SEQ ID NO 141
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser
65                  70

<210> SEQ ID NO 142
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142
```

```
Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser
65                  70
```

<210> SEQ ID NO 143
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

```
Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu
65                  70
```

<210> SEQ ID NO 144
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

```
Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp
65                  70
```

<210> SEQ ID NO 145
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala
65                  70

<210> SEQ ID NO 146
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln
65

<210> SEQ ID NO 147
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu
65

<210> SEQ ID NO 148
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Thr Thr Gln Ser Leu Lys Gln Leu Glu Glu Arg Ala Ala Arg Asn Val

```
                1               5                   10                  15
Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly
65

<210> SEQ ID NO 149
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn
65

<210> SEQ ID NO 150
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu
65

<210> SEQ ID NO 151
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Thr Thr Gln Ser Leu Lys Gln Leu Glu Glu Arg Ala Ala Arg Asn Val
1               5                   10                  15
```

```
Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

<210> SEQ ID NO 152
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp
    50                  55                  60

<210> SEQ ID NO 153
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser
    50                  55                  60

<210> SEQ ID NO 154
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu
    50                  55                  60
```

<210> SEQ ID NO 155
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 155

```
Thr Thr Gln Ser Leu Lys Gln Leu Glu Glu Arg Ala Ala Arg Asn Val
1               5                  10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu
    50                  55                  60
```

<210> SEQ ID NO 156
<211> LENGTH: 59
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 156

```
Thr Thr Gln Ser Leu Lys Gln Leu Glu Glu Arg Ala Ala Arg Asn Val
1               5                  10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu
    50                  55
```

<210> SEQ ID NO 157
<211> LENGTH: 58
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 157

```
Thr Thr Gln Ser Leu Lys Gln Leu Glu Glu Arg Ala Ala Arg Asn Val
1               5                  10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp
    50                  55
```

<210> SEQ ID NO 158
<211> LENGTH: 57
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln
    50                  55

<210> SEQ ID NO 159
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser
    50                  55

<210> SEQ ID NO 160
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys
    50                  55

<210> SEQ ID NO 161
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu
    50

<210> SEQ ID NO 162
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg
    50

<210> SEQ ID NO 163
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln
    50

<210> SEQ ID NO 164
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln
    50

<210> SEQ ID NO 165
<211> LENGTH: 50
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 165

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu
    50

<210> SEQ ID NO 166
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala

<210> SEQ ID NO 167
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

<210> SEQ ID NO 168
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu
        35                  40                  45

```
<210> SEQ ID NO 169
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu
        35                  40                  45

<210> SEQ ID NO 170
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu
        35                  40                  45

<210> SEQ ID NO 171
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu
        35                  40

<210> SEQ ID NO 172
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu
        35                  40
```

<210> SEQ ID NO 173
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln
        35                  40

<210> SEQ ID NO 174
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser
        35                  40

<210> SEQ ID NO 175
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile
        35                  40

<210> SEQ ID NO 176
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln
        35

```
<210> SEQ ID NO 177
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr
        35

<210> SEQ ID NO 178
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser
        35

<210> SEQ ID NO 179
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln
        35

<210> SEQ ID NO 180
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser
```

-continued

```
<210> SEQ ID NO 181
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys

<210> SEQ ID NO 182
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln

<210> SEQ ID NO 183
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

<210> SEQ ID NO 184
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln

<210> SEQ ID NO 185
<211> LENGTH: 31
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met
            20                  25                  30

<210> SEQ ID NO 186
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln

<210> SEQ ID NO 187
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met
            20                  25                  30

<210> SEQ ID NO 188
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln
            20                  25                  30

<210> SEQ ID NO 189
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Thr Thr Gln Ser Leu Lys Gln Leu Glu Glu Arg Ala Ala Arg Asn Val

```
                1               5                   10                  15
Ser Gln Val Ser Lys Asn Leu Glu Ser His His Gly Asp
            20                  25

<210> SEQ ID NO 190
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln

<210> SEQ ID NO 191
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly
            20                  25

<210> SEQ ID NO 192
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln

<210> SEQ ID NO 193
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Thr Thr Gln Ser Leu Lys Gln Leu Glu Glu Arg Ala Ala Arg Asn Val
1               5                   10                  15

Ser Gln Val Ser Lys Asn Leu Glu Ser His His
            20                  25

<210> SEQ ID NO 194
```

```
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Thr Thr Gln Ser Leu Lys Gln Leu Glu Glu Arg Ala Ala Arg Asn Val
1               5                   10                  15

Ser Gln Val Ser Lys Asn Leu Glu Ser His
            20                  25

<210> SEQ ID NO 195
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Thr Thr Gln Ser Leu Lys Gln Leu Glu Glu Arg Ala Ala Arg Asn Val
1               5                   10                  15

Ser Gln Val Ser Lys Asn Leu Glu Ser
            20                  25

<210> SEQ ID NO 196
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Thr Thr Gln Ser Leu Lys Gln Leu Glu Glu Arg Ala Ala Arg Asn Val
1               5                   10                  15

Ser Gln Val Ser Lys Asn Leu Glu
            20

<210> SEQ ID NO 197
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Thr Thr Gln Ser Leu Lys Gln Leu Glu Glu Arg Ala Ala Arg Asn Val
1               5                   10                  15

Ser Gln Val Ser Lys Asn Leu
            20

<210> SEQ ID NO 198
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Thr Thr Gln Ser Leu Lys Gln Leu Glu Glu Arg Ala Ala Arg Asn Val
1               5                   10                  15
```

```
Ser Gln Val Ser Lys Asn
            20

<210> SEQ ID NO 199
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Thr Thr Gln Ser Leu Lys Gln Leu Glu Glu Arg Ala Ala Arg Asn Val
1               5                  10                  15

Ser Gln Val Ser Lys
            20

<210> SEQ ID NO 200
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Thr Thr Gln Ser Leu Lys Gln Leu Glu Glu Arg Ala Ala Arg Asn Val
1               5                  10                  15

Ser Gln Val Ser
            20

<210> SEQ ID NO 201
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Thr Thr Gln Ser Leu Lys Gln Leu Glu Glu Arg Ala Ala Arg Asn Val
1               5                  10                  15

Ser Gln Val

<210> SEQ ID NO 202
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Thr Thr Gln Ser Leu Lys Gln Leu Glu Glu Arg Ala Ala Arg Asn Val
1               5                  10                  15

Ser Gln

<210> SEQ ID NO 203
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 203

Thr Thr Gln Ser Leu Lys Gln Leu Glu Glu Arg Ala Ala Arg Asn Val
1               5                  10                  15

Ser

<210> SEQ ID NO 204
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Thr Thr Gln Ser Leu Lys Gln Leu Glu Glu Arg Ala Ala Arg Asn Val
1               5                  10                  15

<210> SEQ ID NO 205
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Thr Thr Gln Ser Leu Lys Gln Leu Glu Glu Arg Ala Ala Arg Asn
1               5                  10                  15

<210> SEQ ID NO 206
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Thr Thr Gln Ser Leu Lys Gln Leu Glu Glu Arg Ala Ala Arg
1               5                  10

<210> SEQ ID NO 207
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Thr Thr Gln Ser Leu Lys Gln Leu Glu Glu Arg Ala Ala
1               5                  10

<210> SEQ ID NO 208
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Thr Thr Gln Ser Leu Lys Gln Leu Glu Glu Arg Ala
1               5                  10

<210> SEQ ID NO 209
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Thr Thr Gln Ser Leu Lys Gln Leu Glu Glu Arg
1               5                   10

<210> SEQ ID NO 210
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Glu Gly Ser Ala Glu
1               5

<210> SEQ ID NO 211
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Ser Ala Glu
1

<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Glu Gln Lys Leu Ile Ser Glu Glu Asp Leu
1               5                   10

<210> SEQ ID NO 213
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
gaacagaaac tgatctctga agaagacctg                                          30

<210> SEQ ID NO 214
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments
```

<400> SEQUENCE: 214

```
Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Leu Glu Glu Leu Arg
        35                  40                  45

Ala Glu Gln Gln Arg Leu Lys Ser Gln Asp Leu Glu Leu Ser Trp Asn
50                  55                  60

Leu Asn Gly Leu Gln Ala Asp Leu Ser Ser Phe Lys Ser Gln Glu Leu
65                  70                  75                  80

Asn Glu Arg Asn Glu Ala Ser Asp Leu Leu Glu Arg Leu Arg Glu Glu
                85                  90                  95

Val Thr Lys Leu Arg Met Glu Leu Gln Val Ser Ser Gly Phe Val Cys
            100                 105                 110

Asn Thr Cys Pro Glu Lys Trp Ile Asn Phe Gln Arg Lys Cys Tyr Tyr
        115                 120                 125

Phe Gly Lys Gly Thr Lys Gln Trp Val His Ala Arg Tyr Ala Cys Asp
    130                 135                 140

Asp Met Glu Gly Gln Leu Val Ser Ile His Ser Pro Glu Glu Gln Asp
145                 150                 155                 160

Phe Leu Thr Lys His Ala Ser His Thr Gly Ser Trp Ile Gly Leu Arg
                165                 170                 175

Asn Leu Asp Leu Lys Gly Glu Phe Ile Trp Val Asp Gly Ser His Val
            180                 185                 190

Asp Tyr Ser Asn Trp Ala Pro Gly Glu Pro Thr Ser Arg Ser Gln Gly
        195                 200                 205

Glu Asp Cys Val Met Met Arg Gly Ser Gly Arg Trp Asn Asp Ala Phe
    210                 215                 220

Cys Asp Arg Lys Leu Gly Ala Trp Val Cys Asp Arg Leu Ala Thr Cys
225                 230                 235                 240

Thr Pro Pro Ala
```

<210> SEQ ID NO 215
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (138)..(138)
<223> OTHER INFORMATION: Ser, Leu or absent
<220> FEATURE:
<221> NAME/KEY: MOD_RES
<222> LOCATION: (139)..(143)
<223> OTHER INFORMATION: May or may not be present
<220> FEATURE:
<221> NAME/KEY: misc_feature
<222> LOCATION: (138)..(143)
<223> OTHER INFORMATION: This region encompasses "Ser Glu Gly Ser Ala
      Glu," "Ser Glu Gly Ser Ala," "Ser Glu Gly Ser," "Ser Glu Gly,"
      "Ser Glu," "Ser," or "Leu" or is absent in its entirety
<220> FEATURE:
<223> OTHER INFORMATION: see specification as filed for detailed
      description of substitutions and preferred embodiments

<400> SEQUENCE: 215

```
Ser Gly Phe Val Cys Asn Thr Cys Pro Glu Lys Trp Ile Asn Phe Gln
1               5                   10                  15
```

```
Arg Lys Cys Tyr Tyr Phe Gly Lys Gly Thr Lys Gln Trp Val His Ala
            20                  25                  30

Arg Tyr Ala Cys Asp Asp Met Glu Gly Gln Leu Val Ser Ile His Ser
        35                  40                  45

Pro Glu Glu Gln Asp Phe Leu Thr Lys His Ala Ser His Thr Gly Ser
    50                  55                  60

Trp Ile Gly Leu Arg Asn Leu Asp Leu Lys Gly Glu Phe Ile Trp Val
65                  70                  75                  80

Asp Gly Ser His Val Asp Tyr Ser Asn Trp Ala Pro Gly Glu Pro Thr
                85                  90                  95

Ser Arg Ser Gln Gly Glu Asp Cys Val Met Met Arg Gly Ser Gly Arg
            100                 105                 110

Trp Asn Asp Ala Phe Cys Asp Arg Lys Leu Gly Ala Trp Val Cys Asp
        115                 120                 125

Arg Leu Ala Thr Cys Thr Pro Pro Ala Xaa Glu Gly Ser Ala Glu
    130                 135                 140

<210> SEQ ID NO 216
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (245)..(245)
<223> OTHER INFORMATION: Ser, Leu or absent
<220> FEATURE:
<221> NAME/KEY: MOD_RES
<222> LOCATION: (246)..(250)
<223> OTHER INFORMATION: May or may not be present
<220> FEATURE:
<221> NAME/KEY: misc_feature
<222> LOCATION: (245)..(250)
<223> OTHER INFORMATION: This region encompasses "Ser Glu Gly Ser Ala
      Glu," "Ser Glu Gly Ser Ala," "Ser Glu Gly Ser," "Ser Glu Gly,"
      "Ser Glu," "Ser," or "Leu" or is absent in its entirety
<220> FEATURE:
<223> OTHER INFORMATION: see specification as filed for detailed
      description of substitutions and preferred embodiments

<400> SEQUENCE: 216

Thr Thr Gln Ser Leu Lys Gln Leu Glu Glu Arg Ala Ala Arg Asn Val
1               5                   10                  15

Ser Gln Val Ser Lys Asn Leu Glu Ser His His Gly Asp Gln Met Ala
            20                  25                  30

Gln Lys Ser Gln Ser Thr Gln Ile Ser Gln Glu Leu Glu Glu Leu Arg
        35                  40                  45

Ala Glu Gln Gln Arg Leu Lys Ser Gln Asp Leu Glu Leu Ser Trp Asn
    50                  55                  60

Leu Asn Gly Leu Gln Ala Asp Leu Ser Ser Phe Lys Ser Gln Glu Leu
65                  70                  75                  80

Asn Glu Arg Asn Glu Ala Ser Asp Leu Leu Glu Arg Leu Arg Glu Glu
                85                  90                  95

Val Thr Lys Leu Arg Met Glu Leu Gln Val Ser Ser Gly Phe Val Cys
            100                 105                 110

Asn Thr Cys Pro Glu Lys Trp Ile Asn Phe Gln Arg Lys Cys Tyr Tyr
        115                 120                 125

Phe Gly Lys Gly Thr Lys Gln Trp Val His Ala Arg Tyr Ala Cys Asp
    130                 135                 140
```

```
Asp Met Glu Gly Gln Leu Val Ser Ile His Ser Pro Glu Glu Gln Asp
145                 150                 155                 160

Phe Leu Thr Lys His Ala Ser His Thr Gly Ser Trp Ile Gly Leu Arg
                165                 170                 175

Asn Leu Asp Leu Lys Gly Glu Phe Ile Trp Val Asp Gly Ser His Val
            180                 185                 190

Asp Tyr Ser Asn Trp Ala Pro Gly Glu Pro Thr Ser Arg Ser Gln Gly
        195                 200                 205

Glu Asp Cys Val Met Met Arg Gly Ser Gly Arg Trp Asn Asp Ala Phe
    210                 215                 220

Cys Asp Arg Lys Leu Gly Ala Trp Val Cys Asp Arg Leu Ala Thr Cys
225                 230                 235                 240

Thr Pro Pro Ala Xaa Glu Gly Ser Ala Glu
                245                 250
```